United States Patent
Muzerelle et al.

(10) Patent No.: US 9,585,891 B2
(45) Date of Patent: Mar. 7, 2017

(54) ALPHA HYDROXY AMIDES

(71) Applicant: MERCK PATENT GMBH, Darmstadt (DE)

(72) Inventors: Mathilde Muzerelle, Gaillard (FR); Dominique Swinnen, Braine l'Alleud (BE); Jeyaprakashnarayanan Seenisamy, Bangalore (IN)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/430,953

(22) PCT Filed: Sep. 10, 2013

(86) PCT No.: PCT/EP2013/002716
§ 371 (c)(1),
(2) Date: Mar. 25, 2015

(87) PCT Pub. No.: WO2014/048547
PCT Pub. Date: Apr. 3, 2014

(65) Prior Publication Data
US 2015/0250792 A1  Sep. 10, 2015

(30) Foreign Application Priority Data

Sep. 25, 2012 (EP) .................... 12185835

(51) Int. Cl.
| | | |
|---|---|---|
| C07C 237/06 | (2006.01) |
| C07C 235/06 | (2006.01) |
| C07D 265/32 | (2006.01) |
| C07D 307/16 | (2006.01) |
| C07D 295/26 | (2006.01) |
| C07D 333/24 | (2006.01) |
| A61K 31/5375 | (2006.01) |
| A61K 31/16 | (2006.01) |
| A61K 31/165 | (2006.01) |
| A61K 31/381 | (2006.01) |
| A61K 31/4453 | (2006.01) |
| C07C 255/54 | (2006.01) |
| C07C 275/28 | (2006.01) |
| C07D 333/20 | (2006.01) |
| C07C 311/04 | (2006.01) |
| C07C 311/13 | (2006.01) |
| C07C 311/21 | (2006.01) |
| C07D 401/12 | (2006.01) |
| C07C 317/22 | (2006.01) |

(Continued)

(52) U.S. Cl.
CPC .......... *A61K 31/5375* (2013.01); *A61K 31/16* (2013.01); *A61K 31/165* (2013.01); *A61K 31/341* (2013.01); *A61K 31/381* (2013.01); *A61K 31/4453* (2013.01); *C07C 235/06* (2013.01); *C07C 235/12* (2013.01); *C07C 235/80* (2013.01); *C07C 237/06* (2013.01); *C07C 237/22* (2013.01); *C07C 255/54* (2013.01); *C07C 275/28* (2013.01); *C07C 311/04* (2013.01); *C07C 311/13* (2013.01); *C07C 311/21* (2013.01); *C07C 317/22* (2013.01); *C07C 317/32* (2013.01); *C07D 211/26* (2013.01); *C07D 211/58* (2013.01); *C07D 211/96* (2013.01); *C07D 213/68* (2013.01); *C07D 265/32* (2013.01); *C07D 295/088* (2013.01); *C07D 295/135* (2013.01); *C07D 295/185* (2013.01); *C07D 295/26* (2013.01); *C07D 307/14* (2013.01); *C07D 307/16* (2013.01); *C07D 333/20* (2013.01); *C07D 333/24* (2013.01); *C07D 401/12* (2013.01); *C07D 405/12* (2013.01); *C07C 2101/02* (2013.01); *C07C 2101/14* (2013.01)

(58) Field of Classification Search
CPC combination set(s) only.
See application file for complete search history.

(56) References Cited

U.S. PATENT DOCUMENTS

| | | | |
|---|---|---|---|
| 2,692,895 A | 10/1954 | Opfermann et al. | |
| 7,727,738 B2 * | 6/2010 | Burkart .................. | C12P 13/02 435/18 |

(Continued)

FOREIGN PATENT DOCUMENTS

| | | | |
|---|---|---|---|
| WO | WO 2011/152720 | 12/2011 | |
| WO | WO 2012064632 A1 * | 5/2012 | ........... A61K 31/416 |

OTHER PUBLICATIONS

Lutz et al. J. Org. Chem. 1946, 12, 96-107.*
Meier et al. "Synthesis and Evaluation of Bioorthogonal Pantetheine Analogues for in Vivo Protein Modification" J. Am. Chem. Soc. 2006, 128, 12174-12184.*
Lutz, R. et al. "Antimalarials. Amides Related to Phenylpantothenone" *Journal of Organic Chemistry*, Jan. 1, 1947, pp. 96-107, vol. 12, No. 1.

Primary Examiner — Michael Barker
Assistant Examiner — Amanda L Aguirre
(74) *Attorney, Agent, or Firm* — Saliwanchik, Lloyd & Eisenschenk

(57) ABSTRACT

The present invention relates to alpha hydroxy amides including compounds of formula I:

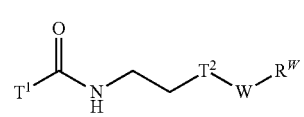

(I)

and related compounds and their use in the prophylaxis and treatment of inflammatory disorders and diseases, wherein $T^1$, $T^2$, W and $R^W$ have the meanings given in claim 1.

13 Claims, No Drawings

(51) Int. Cl.

| | |
|---|---|
| *C07C 317/32* | (2006.01) |
| *C07D 405/12* | (2006.01) |
| *C07C 235/12* | (2006.01) |
| *C07C 235/80* | (2006.01) |
| *C07C 237/22* | (2006.01) |
| *C07D 211/26* | (2006.01) |
| *C07D 295/088* | (2006.01) |
| *C07D 211/58* | (2006.01) |
| *C07D 295/135* | (2006.01) |
| *C07D 295/185* | (2006.01) |
| *C07D 211/96* | (2006.01) |
| *C07D 213/68* | (2006.01) |
| *C07D 307/14* | (2006.01) |
| *A61K 31/341* | (2006.01) |

(56) References Cited

U.S. PATENT DOCUMENTS

| | | | |
|---|---|---|---|
| 8,119,364 B2 * | 2/2012 | Burkart | C12P 13/02 |
| | | | 435/18 |
| 2007/0128683 A1 | 6/2007 | Burkart et al. | |
| 2013/0345270 A1 * | 12/2013 | Kridel | A61K 31/416 |
| | | | 514/379 |

* cited by examiner

ALPHA HYDROXY AMIDES

CROSS-REFERENCE TO RELATED APPLICATION

This application is the U.S. national stage application of International Patent Application No. PCT/EP2013/002716, filed Sep. 10, 2013.

The present invention relates to alpha hydroxy amides including compounds of formula I and related compounds and their use in the prophylaxis and treatment of inflammatory disorders and diseases.

Specifically, the invention relates to the compounds of formula (I):

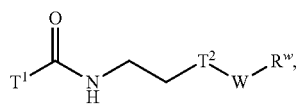

(I)

wherein:
$T^1$ denotes one of the following groups:

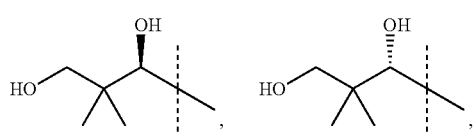

$T^2$-W denotes one of the following groups:

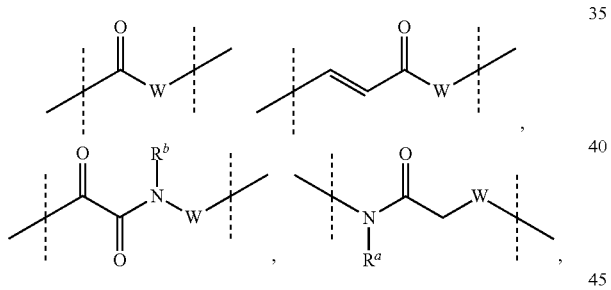

W denotes a single bond, or a group selected from —CHIR$^c$— and —CH=CH—,
$R^W$ denotes a group selected from H, Hal, linear or branched alkyl, Ar, Het, Cyc, —(CH$_2$)$_n$Ar, —(CH$_2$)$_n$Het, —(CH$_2$)$_n$Cyc, —(CH$_2$)$_n$OAr, —(CH$_2$)$_n$OHet, —(CH$_2$)$_n$OCyc, A,
$R^b$ denotes H or a linear or branched alkyl, or, alternatively, $R^b$ and $R^w$, together with the nitrogen atom to which they are linked, form a Het group, preferably a saturated Het group, such as pyrrolidinyl, piperidinyl or morpholinyl,
$R^c$ denotes H, Ar, or alkyl,
$R^a$ denotes H or a group selected from the following groups:

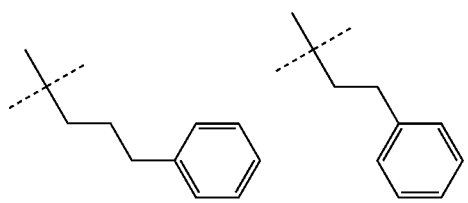

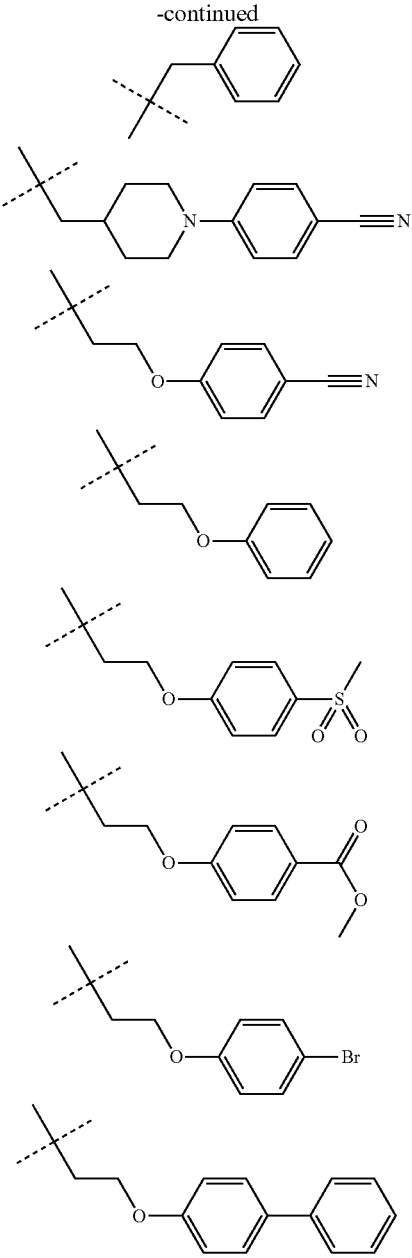

Ar denotes one of the following groups:

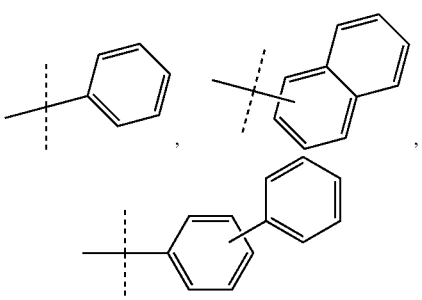

optionally substituted with from 1 to 5 groups independently selected from Hal, CN, —CF$_3$, —OCF$_3$, O-alkyl, SO$_2$-alkyl, COOR$^b$, —CO-alkyl, O-phenyl, SO$_2$-phenyl, SO$_2$—Het, O-Het, Het, —(CH$_2$)$_n$—Het, SO$_2$—CF$_3$, O—(CH$_2$)$_n$—Het, O—(CH$_2$)$_n$-alkyl, A, Het denotes a monocyclic 5-8-membered ring being saturated, unsaturated or aromatic, containing 1 to 3 heteroatoms independently selected from N, O and S, and/or a CO group, and optionally substituted with from 1 to 5 groups independently selected from Hal, CN, —CF$_3$, —OCF$_3$, O-alkyl, SO$_2$-alkyl, COOR$^b$, —CO-alkyl, O-phenyl, SO$_2$-phenyl, SO$_2$—CF$_3$, O—(CH$_2$)$_n$-alkyl, SO$_2$Ar, Ar, A, Cyc denotes a monocyclic saturated carbocyclic ring having 3-8 carbon atoms and being optionally substituted with from 1 to 5 groups independently selected from Hal, CN, —CF$_3$, —OCF$_3$, O-alkyl, SO$_2$-alkyl, COOR$^b$, —CO-alkyl, O-phenyl, SO$_2$-phenyl, SO$_2$—Het, O-Het, Het, —(CH$_2$)$_n$—Het, SO$_2$—CF$_3$, O—(CH$_2$)$_n$-Het, O—(CH$_2$)$_n$-alkyl, A, A is a branched or linear alkyl having 1 to 12 C atoms, wherein one or more, such as 1 to 7, H atoms may be replaced by Ar, Het, Hal, OR$^b$, COOR$^b$, CN or N(R$^b$)$_2$ and wherein one or more, preferably 1 to 5, CH$_2$-groups may be replaced by O, CO, NR$^b$, S, SO, SO$_2$, phenylene, such as 1,4-phenylene, —CH═CH— or —C≡C— and/or by one of the following groups:

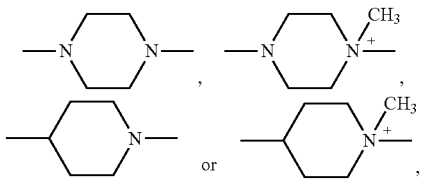

having Hal or mesylate as a counter ion,
Hal denotes F, Cl, Br, I,
and
n is 1, 2 or 3,
and pharmaceutically usable derivatives, solvates, salts and stereoisomers thereof, including mixtures thereof in all ratios.

Preferably, the compounds of formula I show activity as vanin inhibitors.

BACKGROUND OF THE INVENTION

The term "vanin inhibitor" is preferably defined herein as a compound which, in vitro and/or in vivo: (i) inhibits the activity and/or expression of Vanin-1; and/or (ii) blocks processing of pantetheine into cysteamine and pantothenic acid; and/or (iii) blocks intracellular synthesis of cysteamine and/or of cystamine, the oxidized form of cysteamine. Inhibition and blocking may be total or partial.

Vanin-1 and Vanin-3 are preferentially expressed by epithelial and myeloid cells, respectively (Martin, 2001). In human and *drosophila*, this enzyme is encoded by 3 genes (VNN-1, VNN-2, VNN-3). In mouse and human, Vanin-1 and VNN1, respectively, are GPI-anchored to cell membranes and are highly expressed at the brush border of various epithelial cells, including intestinal enterocytes, kidney tubular cells, hepatocytes, pancreatic acinar cells, and thymic medullary epithelial cells (Galland, 1998; Aurrand-Lions, 1996; Pitari, 2000; Martin, 2001). In *drosophila*, 4 genes homologous to the mammalian Vanin sequences are identified and preliminary studies show that *drosophila* has a pantetheinase activity (Granjeaud et al., 1999).

Vanin-1 deficient mice develop normally but have no detectable free cytsteamine/cystamine in kidney and liver, in spite of the presence of Vanin-3 (Pitari, 2000).

Inactivation of the Vanin-1 gene prevents acute and chronic inflammation since in both cases intestinal injury was moderate in Vanin-1 deficient mice, as compared to controls. The protection was associated with reduced expression of inflammatory molecules, myeloid cell recruitment and mucosal damage in the intestine. Furthermore, glutathione synthesis and storage were increased in liver and intestine (US 2004/0247524). These events were further shown to be associated with the lack of free cysteamine/cystamine, which is undetectable in Vanin-1 deficient mice, since cystamine given orally reversed the inflammatory phenotype. This reverting effect was correlated with inhibition of glutathione synthesis in vivo. Thus, the compounds of formula I, which show pronounced activity as vanin inhibitors, are useful for the treatment of inflammatory disorders.

As used herein, "inflammatory disorder" denotes a condition of sustained or chronic inflammation that occurs when tissues are injured by viruses, bacteria, trauma, chemicals, heat, cold or any other harmful stimulus. Preferably, an inflammatory disorder according to the invention is a gastrointestinal inflammatory disorder that may be selected from the group consisting of an inflammatory bowel disease (IBD) such as Irritable Bowel Syndrome (IBS), ulcerative colitis and Crohn's disease, an ulcer resulting from administration of a non-steroidal anti-inflammatory drug, such as a peptic ulcer (i.e., a sore that forms in the lining of the stomach or the duodenum), and an inflammatory disorder associated with an infection with the *Schistosoma mansoni* parasite.

The term "treating" or "treatment" is meant the prophylactic or curative treatment of a disorder, i.e., reversing, alleviating, inhibiting the progress of, or preventing the disorder or condition to which such term applies, or one or more symptoms of such disorder or condition. The treatment may be associated with another pre-existing treatment in order to improve the efficacy of said pre-existing treatment.

Preferred embodiments of the present invention and preferred definitions used therein are described in the following:

Alkyl denotes a carbon chain having 1 to 12 carbon atoms, preferably 1 to 8 carbon atoms and most preferably 1 to 6 carbon atoms. Alkyl very preferably denotes methyl, furthermore ethyl, propyl, isopropyl, butyl, isobutyl, sec-butyl or tert-butyl, furthermore also pentyl, 1, 2 or 3 methylbutyl, 1,1-, 1,2- or 2,2-dimethylpropyl, 1-ethylpropyl, hexyl, 1, 2, 3 or 4 methylpentyl, 1,1-, 1,2-, 1,3-, 2,2-, 2,3- or 3,3-dimethylbutyl, 1 or 2 ethylbutyl, 1 ethyl-1-methylpropyl, 1 ethyl-2-methylpropyl, or 1,1,2- or 1,2,2-trimethylpropyl The group O-alkyl preferably denotes methoxy and ethoxy.

Ar preferably denotes phenyl or biphenyl, which may be unsubstituted or monosubstituted, disubstituted or trisubstituted by a substituent selected from a group mentioned under the definition of Ar.

Het preferably denotes a monocyclic or bicyclic, saturated, unsaturated or aromatic heterocyclic ring having 1 to 3 N, O or S atoms which may be unsubstituted or monosubstituted, disubstituted or trisubstituted by a substituent selected from a group mentioned under the definition of Het.

Het is more preferably a 6- to 14-membered ring system and denotes, notwithstanding further substitutions, for example, 2 or 3 furyl, 2 or 3 thienyl, 1, 2 or 3 pyrrolyl, 1, 2, 4 or 5 imidazolyl, 1, 3, 4 or 5 pyrazolyl, 2, 4 or 5 oxazolyl, 3, 4 or 5 isoxazolyl, 2, 4 or 5 thiazolyl, 3, 4 or 5 isothiazolyl, 2, 3 or 4-pyridyl, 2, 4, 5 or 6 pyrimidinyl, furthermore preferably 1,2,3-triazol-1, 4- or 5-yl, 1,2,4-triazol-1, 3- or 5 yl, 1 or 5 tetrazolyl, 1,2,3-oxadiazol-4- or 5-yl, 1,2,4-oxadiazol-3- or 5-yl, 1,3,4-thiadiazol-2- or 5-yl, 1,2,4-thiadiazol-3- or 5-yl, 1,2,3-thiadiazol-4- or 5 yl, 3 or 4 pyridazinyl, pyrazinyl, 1, 2, 3, 4, 5, 6 or 7 indolyl, indazolyl, 4 or 5 isoindolyl, 1, 2, 4 or 5-benzimidazolyl, 1, 3, 4, 5, 6 or 7 benzopyrazolyl, 2, 4, 5, 6 or 7-benzoxazolyl, 3, 4, 5, 6 or 7 benzisoxazolyl, 2, 4, 5, 6 or 7 benzothiazolyl, 2, 4, 5, 6 or 7 benzisothiazolyl, 4, 5, 6 or 7 benz-2,1,3-oxadiazolyl, 2, 3, 4, 5, 6, 7 or 8 quinolyl, 1, 3, 4, 5, 6, 7 or 8 isoquinolyl, 3, 4, 5, 6, 7 or 8 cinnolinyl, 2, 4, 5, 6, 7 or 8 quinazolinyl, 5 or 6 quinoxalinyl, 2, 3, 5, 6, 7 or 8 2H-benzo-1,4-oxazinyl, furthermore preferably 1,3-benzodioxol-5-yl, 1,4-benzodioxane-6-yl, 2,1,3-benzothiadiazol-4- or 5-yl or 2,1,3-benzoxadiazol-5-yl.

The heterocyclic radicals may also be partially or fully hydrogenated.

Het can thus also denote, for example, 2,3-dihydro-2, 3, 4- or 5-furyl, 2,5-dihydro-2, 3, 4- or 5 furyl, tetrahydro-2- or 3-furyl, 1,3-dioxolan-4-yl, tetrahydro-2- or 3-thienyl, 2,3-dihydro-1, 2, 3, 4- or 5-pyrrolyl, 2,5-dihydro-1, 2, 3, 4- or 5-pyrrolyl, 1, 2 or 3 pyrrolidinyl, tetrahydro-1, 2- or 4-imidazolyl, 2,3-dihydro-1, 2, 3, 4- or 5-pyrazolyl, tetrahydro-1, 3- or 4-pyrazolyl, 1,4-dihydro-1, 2, 3- or 4-pyridyl, 1,2,3,4-tetrahydro-1, 2, 3, 4, 5- or 6-pyridyl, 1, 2, 3 or 4 piperidinyl, 2, 3 or 4 morpholinyl, tetrahydro-2, 3- or 4-pyranyl, 1,4-dioxaneyl, 1,3-dioxane-2, 4- or 5-yl, hexahydro-1, 3- or 4-pyridazinyl, hexahydro-1, 2, 4- or 5-pyrimidinyl, 1, 2 or 3 piperazinyl, 1,2,3,4-tetrahydro-1, 2, 3, 4, 5, 6, 7- or 8-quinolyl, 1,2,3,4-tetrahydro-1, 2, 3, 4, 5, 6, 7- or 8-isoquinolyl, 2, 3, 5, 6, 7 or 8 3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6 yl, 2,3-(2-oxomethylenedioxy) phenyl or 3,4-dihydro-2H-1,5-benzodioxepin-6- or 7-yl, furthermore preferably 2,3-dihydrobenzofuranyl or 2,3-dihydro-2-oxofuranyl.

Cyc preferably denotes cycloalkyl such as cyclopropyl, cyclobutyl, cyclopentyl, cyclohexyl or cycloheptyl.

Above and below, all radicals and indices, such as $T^1$, $T^2$, W, $R^w$, $R^a$, $R^b$, $R^c$, Ar, Het, Hal and n, have the meaning indicated under formula (I), unless expressly stated otherwise.

Generally, compounds of formula I are the more preferred, the more preferred substituents they carry.

W preferably denotes a single bond $CH_2$ or —CH=CH—.

$R^w$ preferably denotes H, alkyl, $(CH_2)_2Ar$, such as phenyl, and in cases where $T^2$-W is

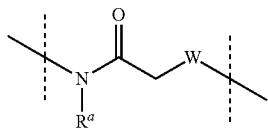

also Hal, more preferably Cl and F.
$R^a$ is preferably H, benzyl, $(CH_2)_2$phenyl, $(CH_2)_3$phenyl or $(CH_2)_2$Ophenyl.
$R^b$ is preferably H.
$R^c$ is preferably H.
N is preferably 1.

Compounds of Formula (I) wherein $R^w$ denotes H, Hal, or a linear or branched alkyl are preferred.

Compounds of Formula (I) wherein $R^w$ denotes one of the following groups are also preferred:

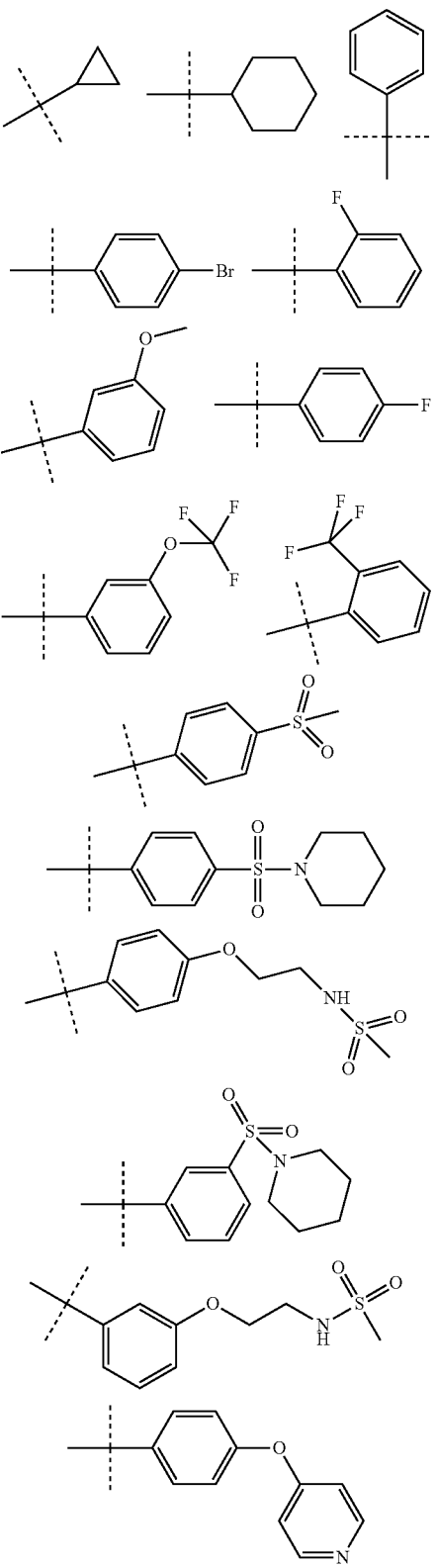

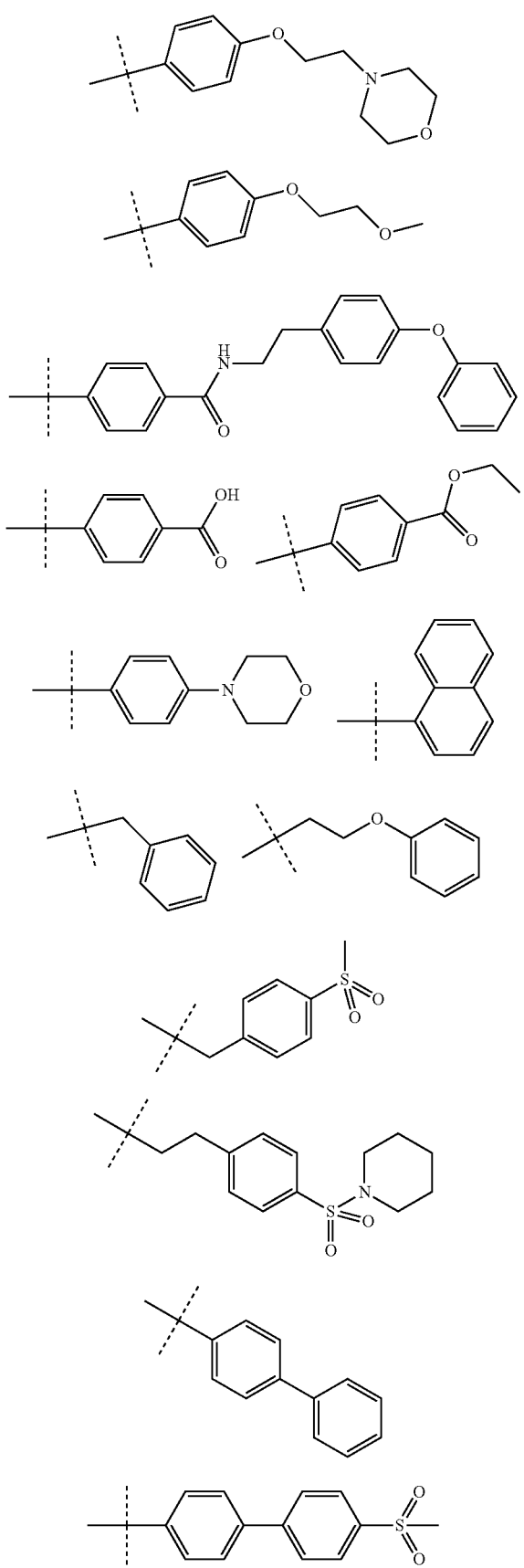
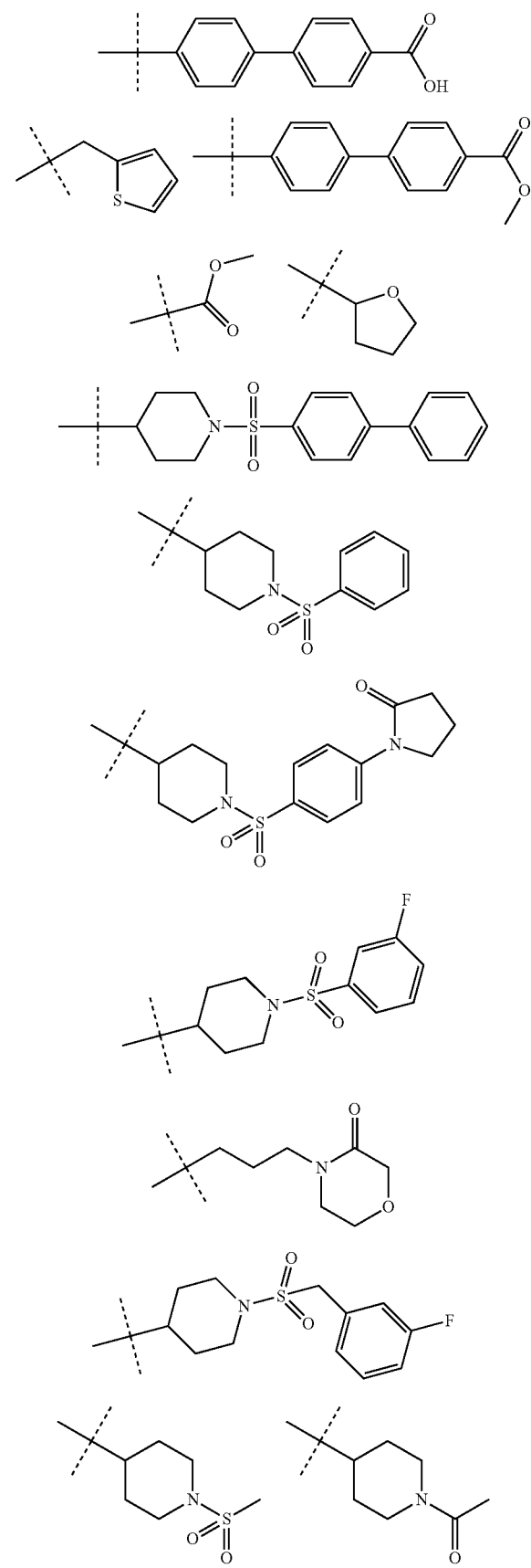

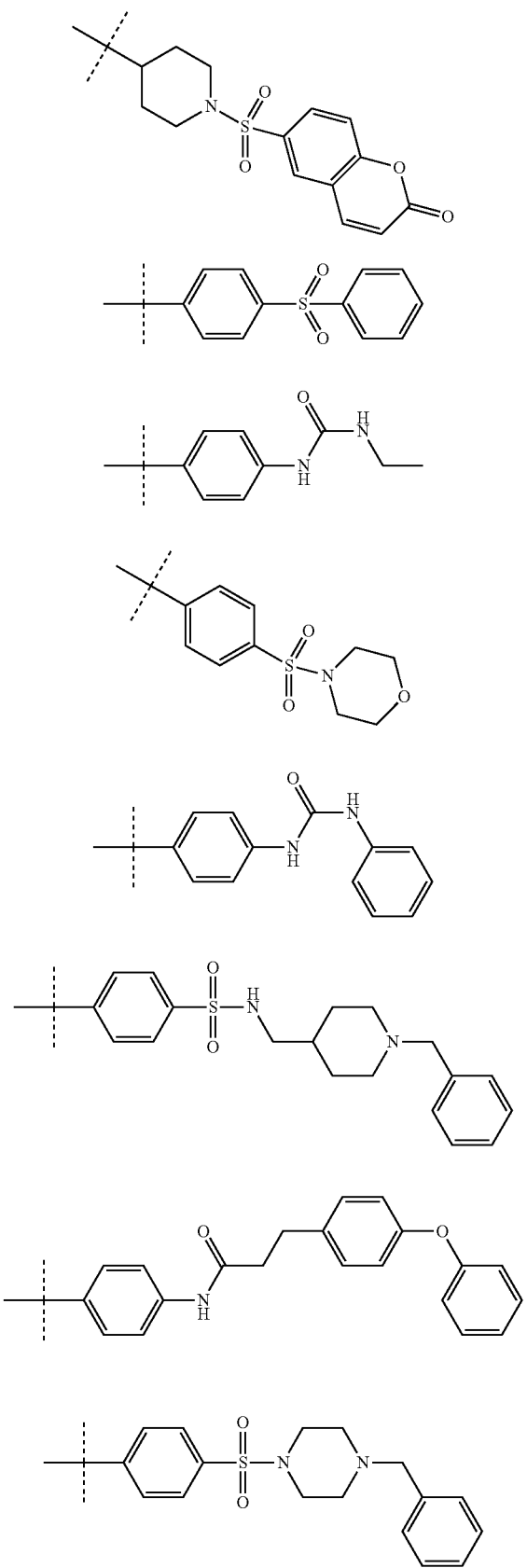

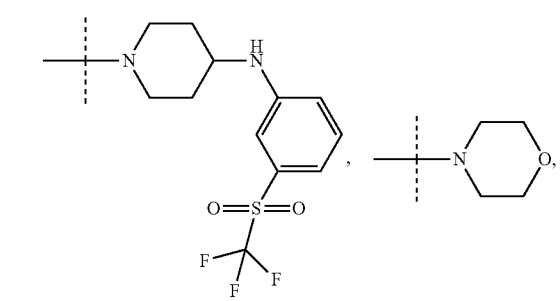

wherein ammonium ions have Hal or mesylate as a counter ion.

Moreover, compounds of formula I are preferred, wherein $R^b$ and $R^w$, together with the nitrogen atom to which they are linked, form one of the following groups:

Very preferred embodiments of the present invention are compounds 1 to 84, which are identified below together with their respective activities:

| Ex | CHEMISTRY | IC50 VNN1 (μM) | IC50 cell (μM) |
|---|---|---|---|
| 1 | | 5.37 | |
| 2 | | 20.50 | |
| 3 | | 9.25 | 1.27 |
| 4 | | 2.01 | 1.19 |
| 5 | | 3.31 | 3.20 |
| 6 | | 5.79 | 0.67 |
| 7 | | 0.83 | 1.49 |
| 8 | | 1.68 | 3.54 |

-continued

| Ex | CHEMISTRY | IC50 VNN1 (μM) | IC50 cell (μM) |
|---|---|---|---|
| 9 | | 0.04 | 0.03 |
| 10 | | 0.03 | 0.025 |
| 11 | | 0.03 | 0.073 |
| 12 | | 0.09 | |
| 13 | | 0.46 | |
| 14 | | 0.05 | 0.09 |
| 15 | | 0.05 | 0.14 |

-continued

| Ex | CHEMISTRY | IC50 VNN1 (μM) | IC50 cell (μM) |
|---|---|---|---|
| 16 | | 8.32 | |
| 17 | | 0.03 | 0.02 |
| 18 | | 3.35 | |
| 19 | | 0.03 | 0.05 |
| 20 | | 3.03 | |
| 21 | | 11.50 | |
| 22 | | 0.06 | 0.03 |

-continued

| Ex | CHEMISTRY | IC50 VNN1 (μM) | IC50 cell (μM) |
|---|---|---|---|
| 23 | | 0.07 | 0.05 |
| 24 | | 0.01 | <0.01 |
| 25 | | 2.32 | |
| 26 | | 0.38 | 0.26 |
| 27 | | 9.73 | |
| 28 | | 0.02 | 0.10 |
| 29 | | 0.70 | |

-continued

| Ex | CHEMISTRY | IC50 VNN1 (μM) | IC50 cell (μM) |
|---|---|---|---|
| 30 | | 0.03 | |
| 31 | | <0.01 | 0.01 |
| 32 | | <0.01 | <0.01 |
| 33 | | <0.01 | <0.01 |
| 34 | | 0.02 | |
| 35 | | 0.07 | |

-continued
| Ex | CHEMISTRY | IC50 VNN1 (μM) | IC50 cell (μM) |
|---|---|---|---|
| 36 | 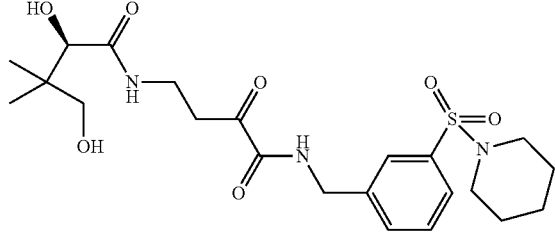 [SMILES: CC(C)(CO)[C@@H](O)C(=O)NCCC(=O)C(=O)NCc1cccc(S(=O)(=O)N2CCCCC2)c1] | 0.17 | |
| 37 | 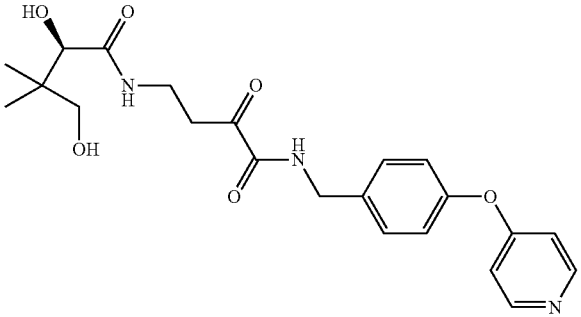 [SMILES: CC(C)(CO)[C@@H](O)C(=O)NCCC(=O)C(=O)NCc1ccc(Oc2ccncc2)cc1] | 0.01 | |
| 38 | 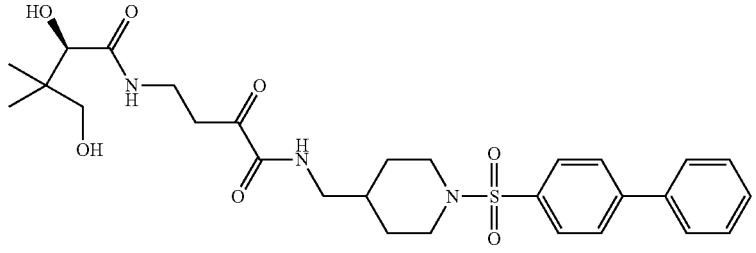 [SMILES: CC(C)(CO)[C@@H](O)C(=O)NCCC(=O)C(=O)NCC1CCN(S(=O)(=O)c2ccc(-c3ccccc3)cc2)CC1] | <0.01 | |
| 39 | 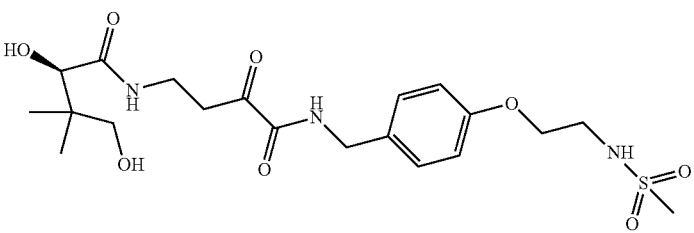 [SMILES: CC(C)(CO)[C@@H](O)C(=O)NCCC(=O)C(=O)NCc1ccc(OCCNS(C)(=O)=O)cc1] | 0.02 | <0.01 |
| 40 | 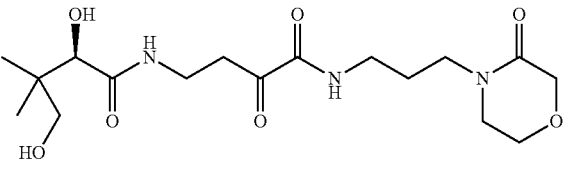 [SMILES: CC(C)(CO)[C@@H](O)C(=O)NCCC(=O)C(=O)NCCCN1CCOCC1=O] | 0.40 | |
| 41 | 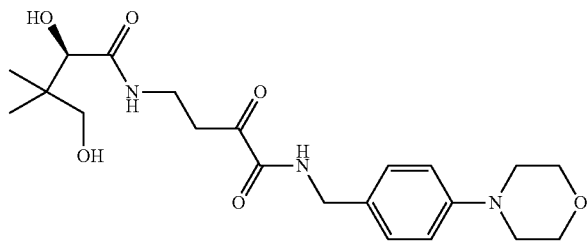 [SMILES: CC(C)(CO)[C@@H](O)C(=O)NCCC(=O)C(=O)NCc1ccc(N2CCOCC2)cc1] | 0.01 | |

-continued

| Ex | CHEMISTRY | IC50 VNN1 (μM) | IC50 cell (μM) |
|----|-----------|----------------|----------------|
| 42 | | | 0.34 |
| 43 | | | 12.60 |
| 44 | | | 0.05 |
| 45 | | | 0.02 |
| 46 | | | <0.01 |
| 47 | | | 0.02 |

| Ex | CHEMISTRY | IC50 VNN1 (μM) | IC50 cell (μM) |
|---|---|---|---|
| 48 | | 0.11 | |
| 49 | | 23.00 | |
| 50 | | 0.03 | |
| 51 | | 0.02 | |
| 52 | | 0.05 | |
| 53 | | 0.01 | |

-continued
| Ex | CHEMISTRY | IC50 VNN1 (μM) | IC50 cell (μM) |
|---|---|---|---|
| 54 | 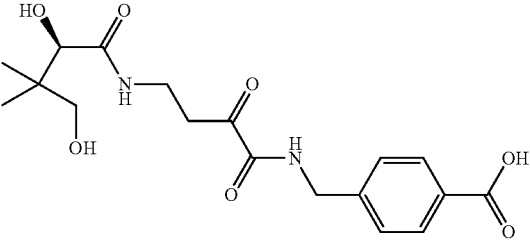 [SMILES: CC(C)(CO)[C@@H](O)C(=O)NCCC(=O)C(=O)NCc1ccc(C(=O)O)cc1] | 0.09 | |
| 55 | 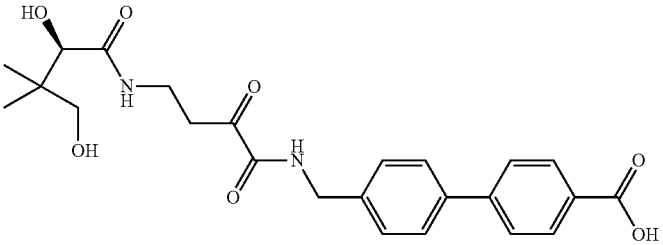 [SMILES: CC(C)(CO)[C@@H](O)C(=O)NCCC(=O)C(=O)NCc1ccc(-c2ccc(C(=O)O)cc2)cc1] | <0.01 | |
| 56 | 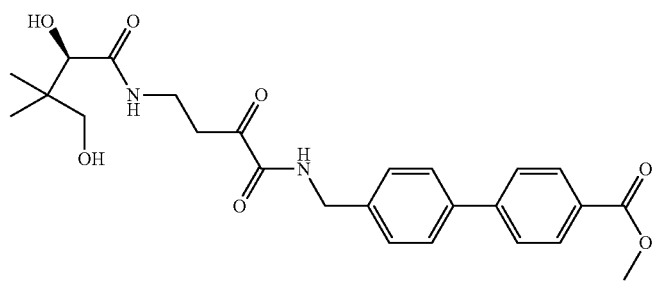 [SMILES: COC(=O)c1ccc(-c2ccc(CNC(=O)C(=O)CCNC(=O)[C@H](O)C(C)(C)CO)cc2)cc1] | 0.01 | |
| 57 | 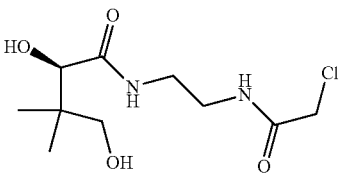 [SMILES: CC(C)(CO)[C@@H](O)C(=O)NCCNC(=O)CCl] | 2.54 | 1.11 |
| 58 | 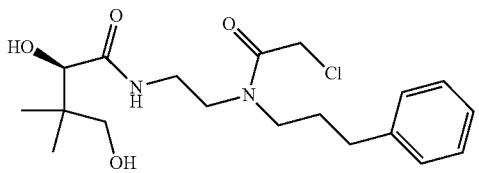 [SMILES: CC(C)(CO)[C@@H](O)C(=O)NCCN(CCCc1ccccc1)C(=O)CCl] | 2.48 | 0.22 |
| 59 | 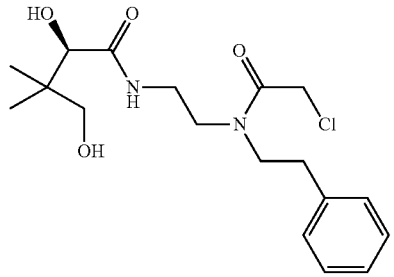 [SMILES: CC(C)(CO)[C@@H](O)C(=O)NCCN(CCc1ccccc1)C(=O)CCl] | 4.04 | 1.20 |

-continued

| Ex | CHEMISTRY | IC50 VNN1 (μM) | IC50 cell (μM) |
|---|---|---|---|
| 60 | | 3.57 | 0.60 |
| 61 | | 3.28 | 0.22 |
| 62 | | 1.36 | 0.21 |
| 63 | | 3.55 | |
| 64 | | 3.44 | |
| 65 | | 3.99 | |

-continued

| Ex | CHEMISTRY | IC50 VNN1 (μM) | IC50 cell (μM) |
|----|-----------|----------------|----------------|
| 66 | | | 2.87 |
| 67 | | | |
| 68 | | | |
| 69 | | | |
| 70 | | | |

| Ex | CHEMISTRY | IC50 VNN1 (μM) | IC50 cell (μM) |
|---|---|---|---|
| 71 | 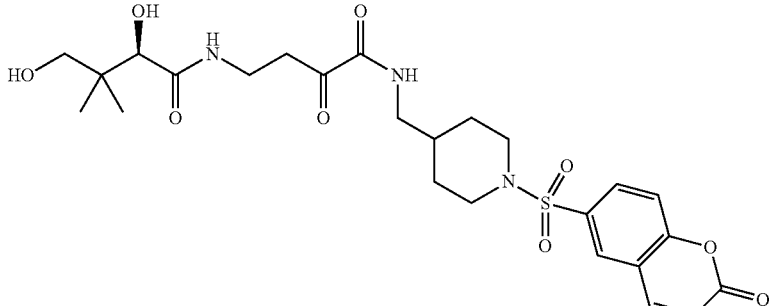 | | |
| 72 | 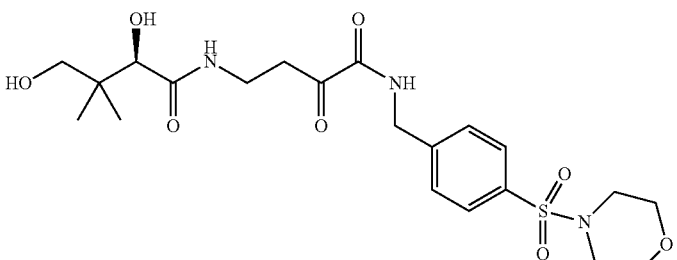 | | |
| 73 | 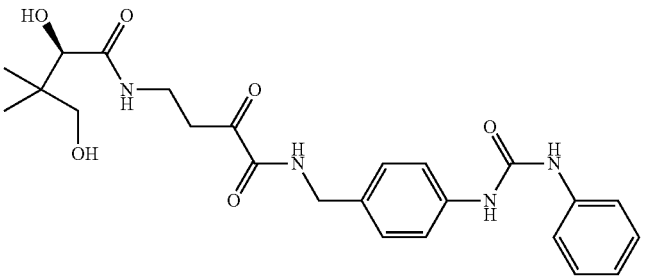 [SMILES: CC(C)(CO)[C@@H](O)C(=O)NCCC(=O)C(=O)NCc1ccc(NC(=O)Nc2ccccc2)cc1] | | |
| 74 | 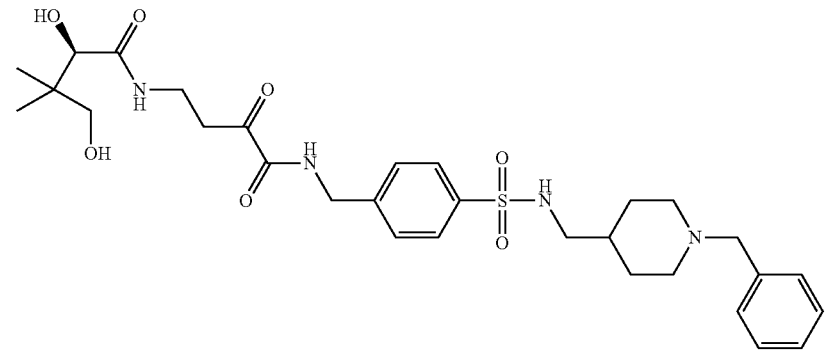 | | |
| 75 | 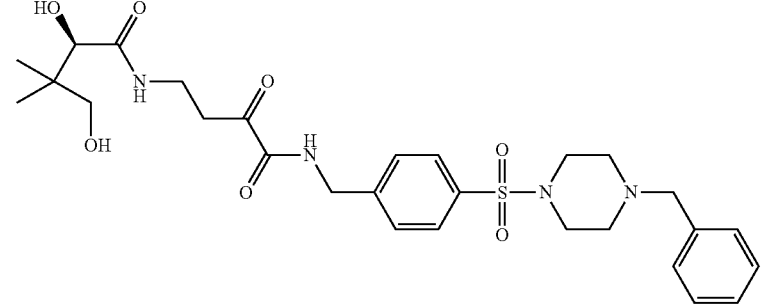 [SMILES: CC(C)(CO)[C@@H](O)C(=O)NCCC(=O)C(=O)NCc1ccc(S(=O)(=O)N2CCN(Cc3ccccc3)CC2)cc1] | | |

| Ex | CHEMISTRY | IC50 VNN1 (μM) | IC50 cell (μM) |
|---|---|---|---|
| 76 | | | |
| 77 | | | |
| 78 | | | |
| 79 | | | |
| 80 | | | |

| Ex | CHEMISTRY | IC50 VNN1 (µM) | IC50 cell (µM) |
|---|---|---|---|
| 81 | 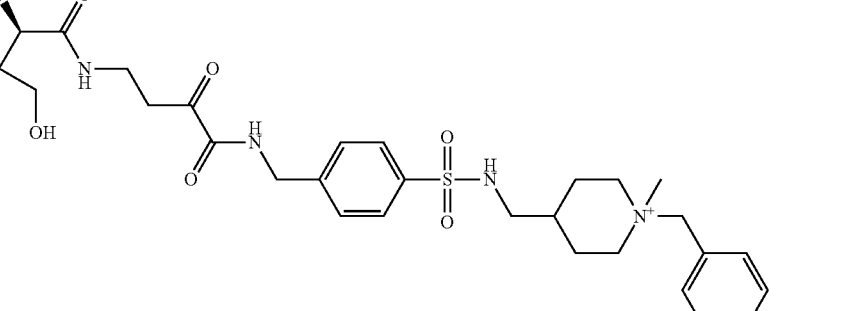 | | |
| 82 | 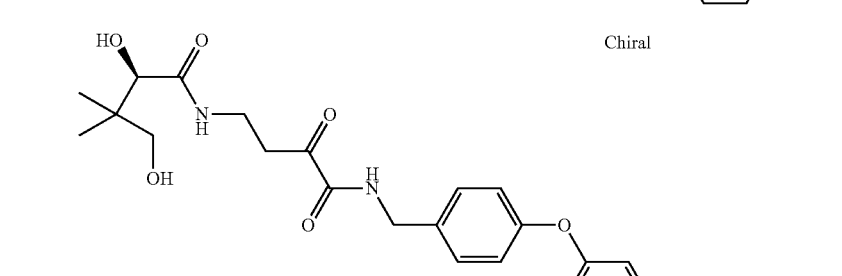 Chiral | | |
| 83 | 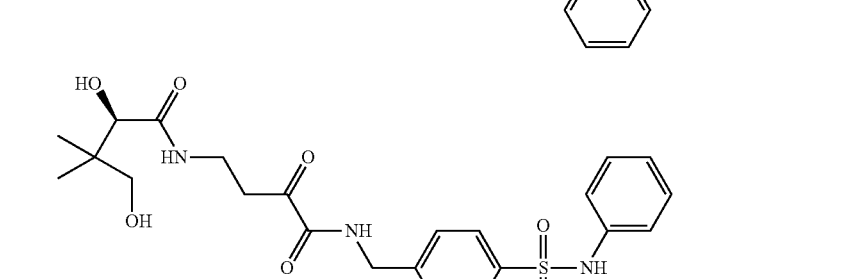 | | |
| 84 | 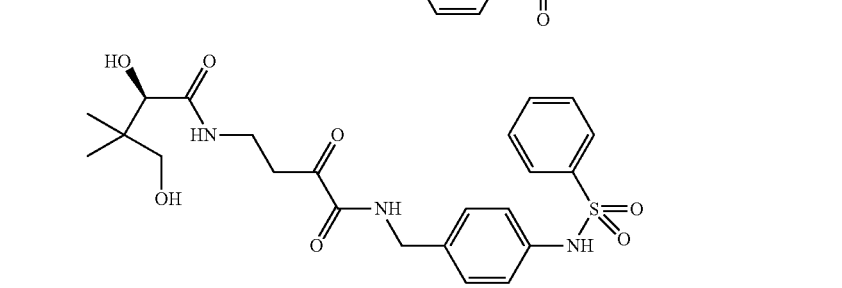 | | | wherein ammonium ions have Hal or mesylate as a counter ion.

Synthesis of Compounds of the Invention:

The following general methods and procedures described hereinafter in the examples may be used to prepare compounds of formula (I) and related formulae.

The compounds according to formula (I) may be prepared from readily available starting materials using the following general methods and procedures. If such starting materials are not commercially available they may be prepared by standard synthetic techniques. It will be appreciated that where typical or preferred experimental conditions (i.e., reaction temperatures, time, stoichiometry of reagents, solvents, etc.) are given, other experimental conditions can also be used unless otherwise stated. Generally, the compounds according to the general formula (I) may be obtained by several processes using both solution-phase and/or solid-phase chemistry protocols. Examples of synthetic pathways for the preparation of compounds according to the general formula (I) are described herebelow. Optimum reaction conditions may vary with particular reactants or solvents used, but such conditions can be determined by the person skilled in the art, using routine optimization procedures.

Below, all substituents, such as $T^1$, $T^2$, W, $R^w$, $R^b$, $R^c$, $R^a$ or n, have the meaning indicated under the formula (I) unless expressly stated otherwise.

Depending on the nature of $T^1$, $T^2$, W, $R^w$, $R^b$, $R^c$, $R^a$ or n, different synthetic strategies may be selected for the synthesis of compounds of formula (I). In general, the synthesis pathways for any individual compound of formula (I) will depend on the specific substituents of each molecule and upon the availability of intermediates; again, such factors being appreciated by those skilled in the art. For all the protection and deprotection methods, see Philip J. Kocienski, in "*Protecting Groups*", Georg Thieme Verlag, Stuttgart, Germany, 1994, and Theodora W. Greene and Peter G. M. Wuts in "*Protective Groups in Organic Synthesis*", Wiley Interscience, 31$^{rd}$ Edition, 1999.

Structures below are drawn for compounds of (R) stereochemistry starting from D-pantolactone of formula (VI). The same reactions and procedure can be followed to obtain (S) derivatives, starting from L-pantolactone.

As a representative example, the compounds according to formula (I) may be prepared following the synthetic pathways described in the general scheme 1. According to a preferred synthetic pathway, compounds of formula (Ia) may be prepared from the corresponding derivatives of formula (IIa) by an oxidation step followed by the cleavage of the acetonide protecting group where, preferably, W represents a single bond or a group —CH=CH— and $R^w$ an alkyl group. Preferred conditions consist of the treatment of compounds of formula (IIa) with an oxidant such as, but not limited to, Dess-Martin periodinane in a solvent such as dry DCM at room temperature for few hours, such as 2 h, followed by treatment with preferably an 80% acetic acid solution in water at room temperature for several hours, such as 3 h. Compounds of formula (IIa) may be prepared from the corresponding derivatives of formula (IIb), wherein W and $R^w$ are as above defined, but preferably representing an alkyl group and W representing a single bond or a group —CH=CH—, by reaction of magnesium bromide derivatives of formula (III) with compounds of formula (IIb) in a solvent such as dry THF at 0° C. for 1 h followed by 1 h at RT. Starting from the alcohol (IIc), compounds of formula (IIb) can be obtained using usual conditions for the oxidation of primary alcohol into aldehyde using Dess-Martin oxidation or Swern oxidation conditions. Preferred conditions consist of the treatment of compounds of formula (IIc) with Dess-Martin periodinane in a solvent such as DCM at 0° C. for few hours, such as 6 h. The corresponding alcohol derivatives can be obtained after protection of compounds of formula (IVa) into an acetonide group by treatment of compounds of formula (IVa) with acetone in the presence of an acid such as, but not limited to, para-toluene sulfonic acid and molecular sieves at room temperature for several days, such as 3 days. Compounds (IVa) may be prepared by the opening of a pantolactone of formula (VI) with amines of formula (Va). Preferred conditions consist of the treatment of compounds of formula (VI) with amines in the presence of a base such as triethylamine, in a suitable solvent such as dry EtOH at a temperature between 100° C. and 160° C.

Compounds of formula (Ib), where $R^w$ is as described above, may be prepared from compounds of formula (IId) following conditions described above to convert compounds of formula (Ia) from compounds of formula (IIa) consisting of the oxidation of the secondary alcohol into a ketone followed by the acetonide deprotection. Compounds of formula (IId) can be obtained from compounds of formula (IIb) by treatment with classic reagents to run Horner-Wadsworth-Emmons reactions such as phosphonate derivatives of formula (VII). Preferred conditions consist of the treatment of phosphonate of formula (VII) with NaH in a suitable solvent such as dry THF at 0° C. for few minutes, such as 15 minutes, followed by the addition of compounds of formula (IIb) at 0° C. for 1 h, then at RT for another hour.

Scheme 1

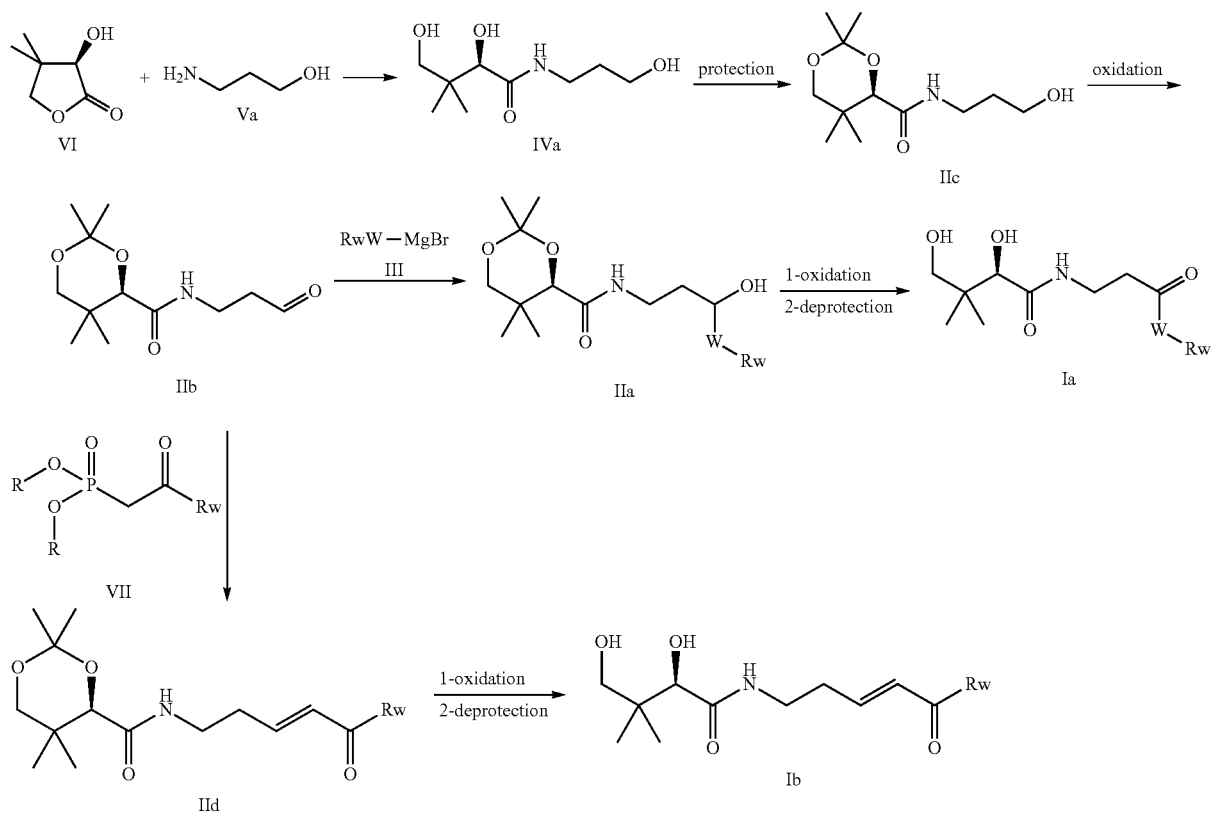

When T² denotes a —CO—CH=CH— group such as represented in Scheme 2, where R^w is as defined above, compounds of general formula (Ic) may be prepared from compounds of formula (IIe) following conditions described above to convert compounds of formula (Ia) from compounds of formula (IIa) consisting of the oxidation of the secondary alcohol into a ketone followed by the acetonide deprotection. Compounds of formula (IIe) can be obtained from compounds of formula (IIf) by treatment with an allyl derivative of formula (VIII) where R^w is as above defined in the presence of a Grubbs catalyst. Preferred conditions consist of the treatment compounds of formula (IIf) with allyl derivatives of formula (VIII) in the presence of second generation Grubbs catalyst in a suitable solvent such as dry DCM at reflux overnight, such as 16 h.

Scheme 2

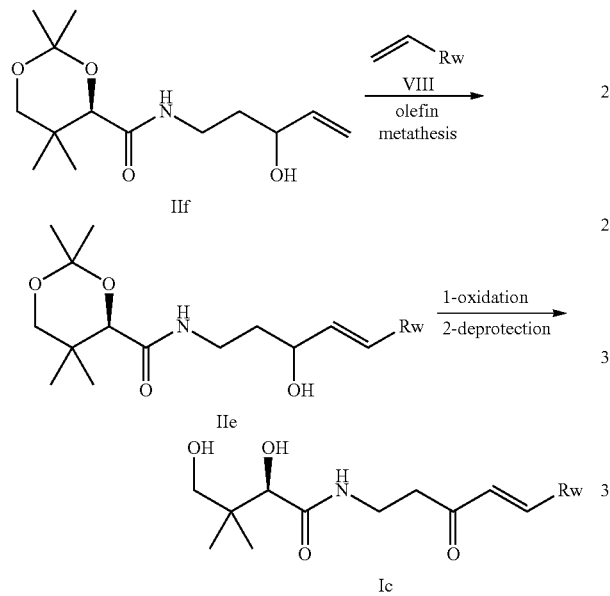

When T² denotes a —CO—CO—NH— group such as represented in Scheme 3, where W represents a single bond and R^w is as defined above, compounds of general formula (Id) may be prepared from compounds of formula (IIg) following conditions described above to convert compounds of formula (Ia) from compounds of formula (IIa) consisting of the oxidation of the secondary alcohol into a ketone followed by the acetonide deprotection. Compounds of formula (IIg) can be obtained from compounds of formula (IIb) by treatment with isocyanide derivatives of formula (IX) where R^w is as defined above. Preferred conditions consist of the treatment compounds of formula (II b) with chloroacetic acid and an isocyanide derivative of formula (IX) in a suitable solvent such as DCM at a temperature such as room temperature. The intermediate is then treated with a base such as $K_2CO_3$ in a MeOH:$H_2O$ mixture for several hours, such as 5 h, at a temperature such as RT.

Scheme 3

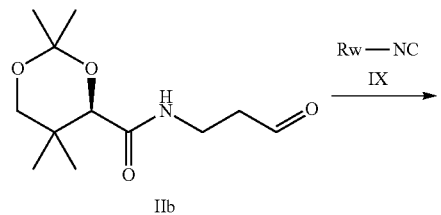

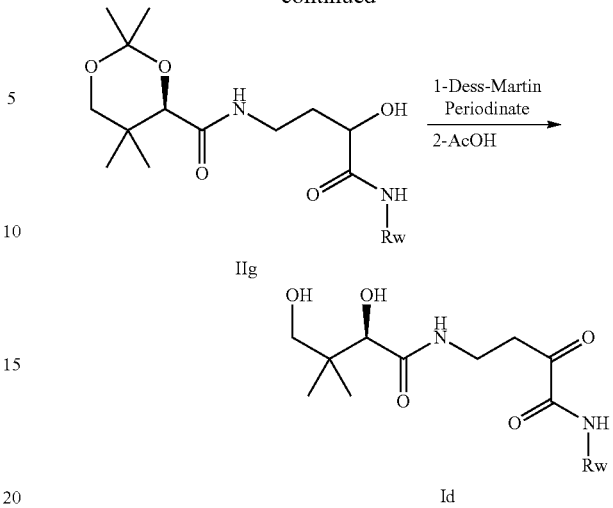

Isocyanide of formula (IX) where R^w is as defined above can be obtained from compounds of formula (X) by treatment with ethylformate followed by the dehydration of the formamide intermediate as shown in Scheme 4. Preferred conditions consist of the treatment of amines of formula (X) with ethylformate at room temperature for a few hours, such as 12 h. The intermediate is then dehydrated by addition of triphosgene in the presence of a base such as triethylamine in a suitable solvent such as DCM at a temperature such as 0° C. followed by an additional 30 min at RT.

Scheme 4

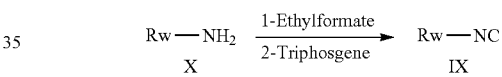

As an alternative example, the compounds according to formula (Id) may be prepared following the synthetic pathway described in Scheme 5. According to a preferred synthetic pathway, compounds of formula (Id) may be prepared from the corresponding derivatives of formula (XIa), by an oxidation step followed by the cleavage of the acetal protecting group where W and R^w are as defined above. Preferred conditions consist of the treatment of compounds of formula (XIa) with an oxidant such as, but not limited to, Dess-Martin periodinane in a solvent such as dry DCM at room temperature for a few hours, such as 2 h, followed by treatment with preferably an 80% acetic acid solution in water at room temperature for several hours, such as 3 h. Compounds of formula (XIa) may be prepared from the corresponding acid derivatives of formula (XIb) by coupling with amine derivatives of formula (XII) wherein W and R^w are as defined above with W preferably representing a single bond. Starting from the acid (XIb), compounds of formula (XIa) can be obtained using usual conditions for the formation of an amide starting from a carboxylic acid and an amine by using coupling agents such as DCC, DIC, EDC, and HATU or via the formation of an acid chloride or an activated ester. Preferred conditions consist of the treatment of compounds of formula (XIb) with HATU in the presence of a base such as, but not limited to, N-methyl morpholine in a solvent such as DMF at a temperature such as 100° C. The corresponding carboxylic acid of formula (XIb) can be obtained by hydrolysis of the corresponding esters of formula (XIc) using reagents such as, but not limited to, LiOH, NaOH or KOH in solvents such water, alcohol, THF, dioxane, or a mixture thereof.

Compounds of formula (XIIIa) may be obtained either from commercial sources or following the procedure described in the journal Organic Letters, 2004, 6(26), 4801-4803.

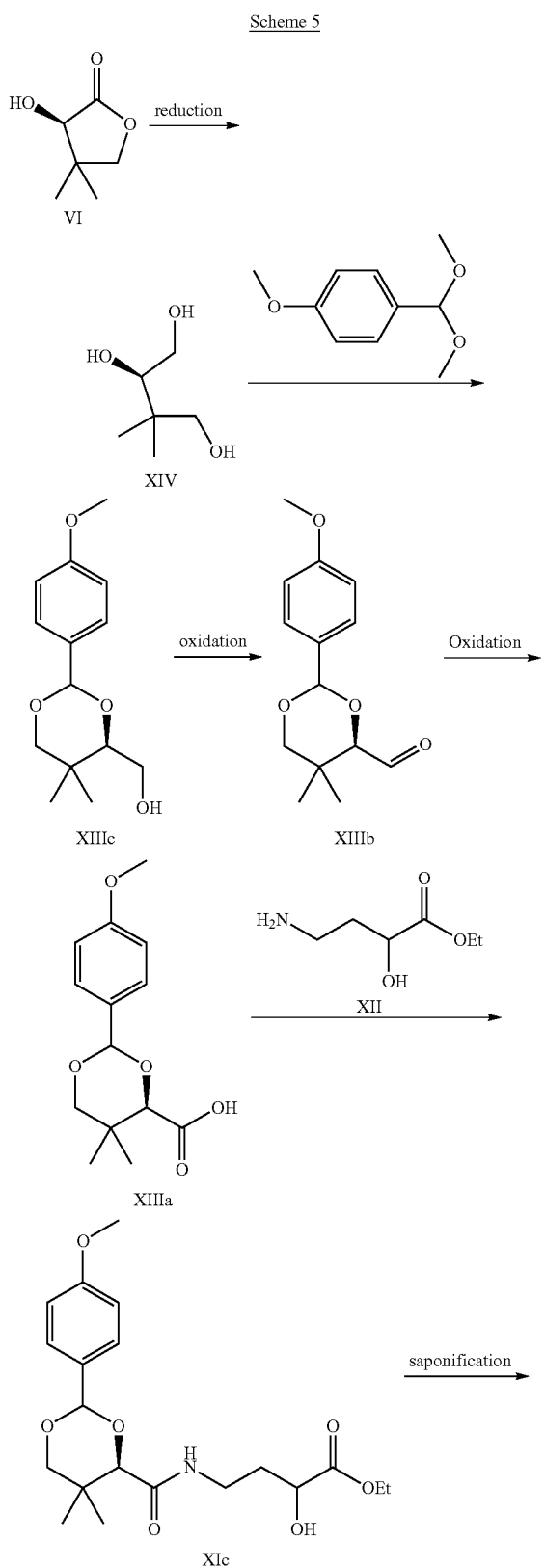

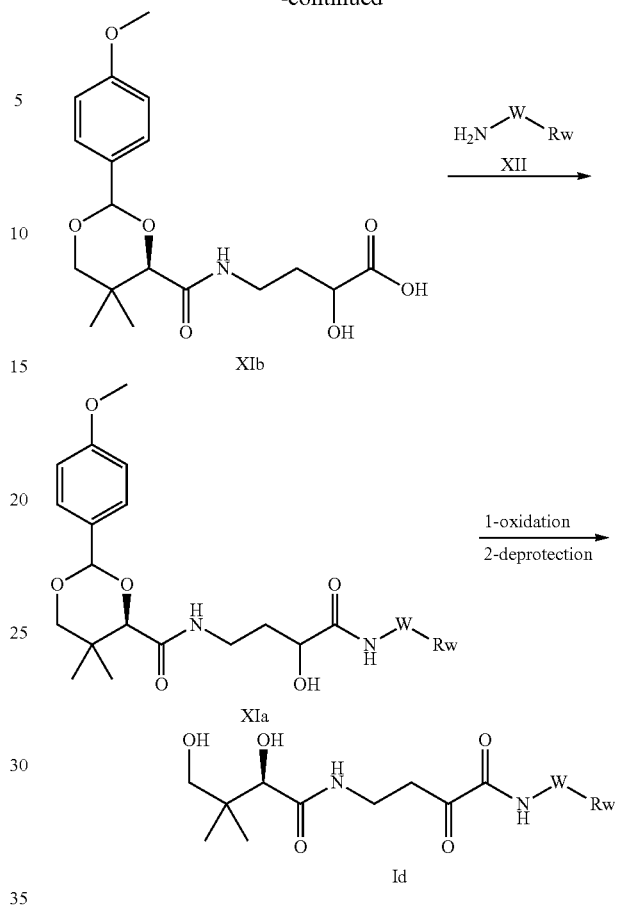

Compounds of formula (Ie) where $T^2$ is N(Ra)—CO—CH$_2$— and Ra is as defined above can be obtained from compounds of formula (If) by treatment with chloroacetyl chloride followed by treatment with a base such as NaOH as shown in Scheme 6. Preferred conditions consist of the treatment of amines of formula (If) with chloroacetyl chloride in the presence of a base such as triethylamine in a suitable solvent such as dry DCM at a temperature such as 0° C. for an hour. The compound is then treated with a base such as a 10% aqueous solution of NaOH in a suitable solvent such as a THF:H$_2$O mixture. Compounds of formula (If) where Ra is as defined above may be prepared from compounds of formula (Vb) following conditions described above to synthesize compounds of formula (IVa) from compounds of formula (VI) and amines of formula (Va) consisting of the opening of a pantolactone by an amine. Compounds of formula (Vb) can be obtained by treatment of compounds of formula (XV) with a sulfonyl chloride such as methane sulfonyl chloride followed by the reaction with ethylene diamine. Preferred conditions consist of the treatment of alcohol derivatives (XV) with methane sulfonyl chloride in the presence of a base such as, but not limited to, triethylamine in a suitable solvent such as dry DCM at a temperature such as 0° C. Methanesulfonic acid derivatives are then treated with ethylene diamine in a suitable solvent such as MeOH at a temperature such as RT for few hours, such as 16 h.

Scheme 6

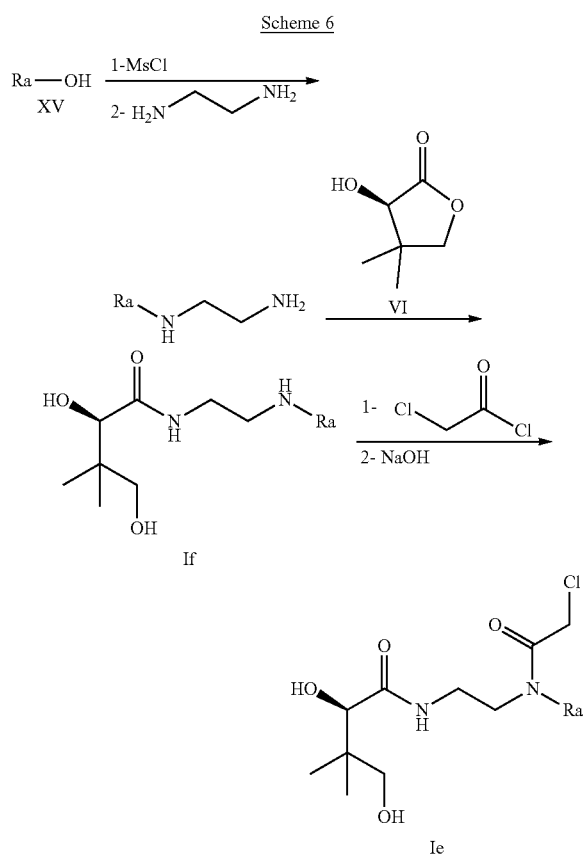

Experimental Part:

The compounds of invention have been named according to the standards used in the program AutoNom (v1.0.1.1).

The compounds according to formula (I) can be prepared from readily available starting materials by several synthetic approaches, using both solution-phase and solid-phase chemistry protocols or mixed solution- and solid-phase protocols. Examples of synthetic pathways are described below in the examples.

EXAMPLES

The commercially available starting materials used in the following experimental description were purchased from Sigma-Aldrich, ACROS or ABCR unless otherwise reported.

$^1$H NMR analyses were carried out using Bruker NMR, 400 MHz FT-NMR. Residual signal of deuterated solvent was used as internal reference. Chemical shifts (δ) are reported in ppm in relative to the residual solvent signal (δ=2.50 for $^1$H NMR in DMSO-$d_6$, and 7.26 in CDCl$_3$), together with multiplicity, coupling constants and number of hydrogen atoms. Multiplicity is abbreviated as follows: s (singlet), d (doublet), t (triplet), q (quartet), br (broad), m (multiplet).

The MS data provided in the examples described below were obtained as followed: Mass spectrum: LC/MS Waters ZMD (ESI).
Method A:
  Method: A—0.1% TFA in H$_2$O, B—0.1% TFA in ACN: Flow—2.0 mL/min.
  Column: XBridge C8 (50×4.6 mm, 3.5 μm), positive mode.

HPLC analyses were obtained as followed with UV detection (maxplot).
Method A:
  Method: A—0.1% TFA in H$_2$O, B—0.1% TFA in ACN: Flow—2.0 mL/min.
  Column: XBridge C8 (50×4.6 mm, 3.5 μm).

The microwave chemistry was performed on an Emrys™ Optimiser or Initiator™ Sixty single mode microwave reactor from Biotage.

Abbreviations:
The following abbreviations refer respectively to the definitions below: aq (aqueous), h (hour), g (gram), L (liter), mg (milligram), MHz (Megahertz), μM (micromolar), min. (minute), mm (millimeter), mmol (millimole), mM (millimolar), eq (equivalent), mL (milliliter), μL (microliter), AcOH (Acetic acid), ACN (acetonitrile), AMC (7-amino-4-methylcoumarin), DCM (dichloromethane), DIEA (diisopropylethyl-amine), DMF (dimethylformamide), DMSO (dimethylsulfoxide), DMSO-$d_6$ (deuterated dimethylsulfoxide), ESI (Electro-spray ionization), EtOAc (ethyl acetate), Et$_2$O (diethyl ether), Et$_3$N (triethylamine), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), LC (Liquid Chromatography), MeOH (methanol), MS (mass spectrometry), MTBE (Methyl tert-butyl ether), MW (microwave), NMR (Nuclear Magnetic Resonance), PTSA (para toluene sulfonic acid), RT (room temperature), Rt (retention time), TEA (triethylamine), THF (tetrahydrofuran), TLC (Thin Layer Chromatography), UV (Ultraviolet), vol (Volume).

General Procedures:
General Procedure A: Acetonide Deprotection

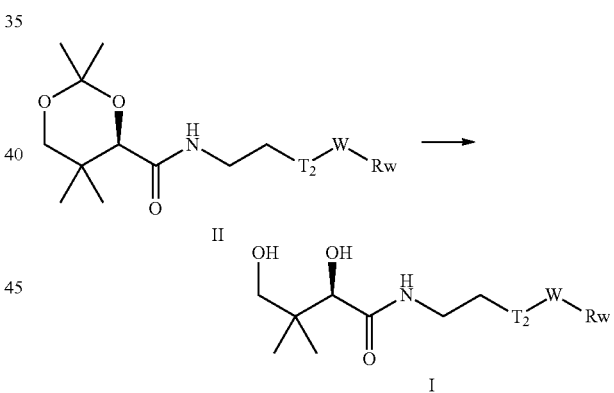

A compound of Formula (II) (1 eq) was dissolved in 80% AcOH in water (5 mL) and stirred for 3 h at RT. After completion of the reaction, the solvent was removed under reduced pressure and the crude product was purified by silica gel column chromatography to get the title compound.

General Procedure B: Oxidation and Deprotection

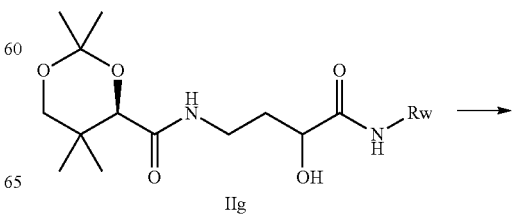

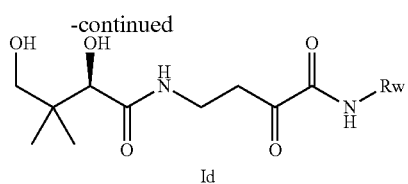

To a solution of compound of Formula (IIg) (1 eq) in dry DCM was added Dess-Martin periodinane (1.5 eq) and stirred at RT for 2 h. After completion of the reaction, the solid was filtered and the filtrate was concentrated under vacuum. The colorless oil was dissolved in 80% AcOH in water (5 mL) and stirred for 3 h at RT. After this time, the solvent was removed under reduced pressure and the crude product was purified by silica gel column chromatography.

General Procedure C: Isocyanides Synthesis

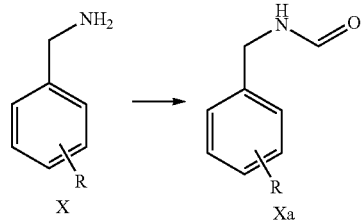

Step 1:

A solution of compound of Formula (X) (1 eq) and ethyl formate (2 eq) was stirred at RT for 12 h. After completion of the reaction, the mixture was concentrated under reduced pressure and taken as such to the next step.

Step 2:

To a solution of the compound of Formula (Xa) (1 eq), NEt$_3$ (3 eq) in DCM (50 vol) cooled at 0° C. was added dropwise a solution of triphosgene (0.5 eq) in DCM (15 vol). The reaction mixture was stirred at RT for 30 min. After this time, the reaction mixture was quenched with ice and extracted with DCM. The organic layer was washed with brine and then dried over anhydrous Na$_2$SO$_4$ and taken as such to the next step.

General Procedure D: Alpha-Hydroxy Amide Synthesis

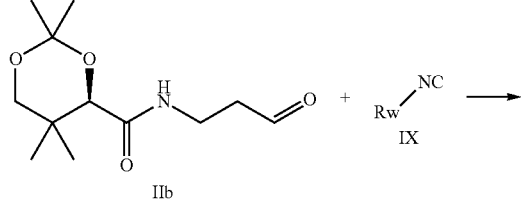

To a stirred solution of compound of Formulae (IIb) (1 eq) in DCM (20 vol) were added chloroacetic acid (1.1 eq) and isocyanide derivative (IX) (1.1 eq) at 0° C. The reaction mixture was stirred at RT for 12 h after which the solvent was removed under vacuum. The solid residue was dissolved in MeOH:H$_2$O (1:1) (20 vol) followed by addition of K$_2$CO$_3$ (2.5 eq) and stirring at RT for 5 h. After completion of the reaction, the solvent was removed under vacuum and the residue was extracted with EtOAc. The organic layer was washed with water followed by brine and the combined organic layers were dried over Na$_2$SO$_4$ and concentrated under vacuum. The crude product was purified by silica gel column chromatography to afford the title compound.

General Procedure E: Acid-Amine Coupling

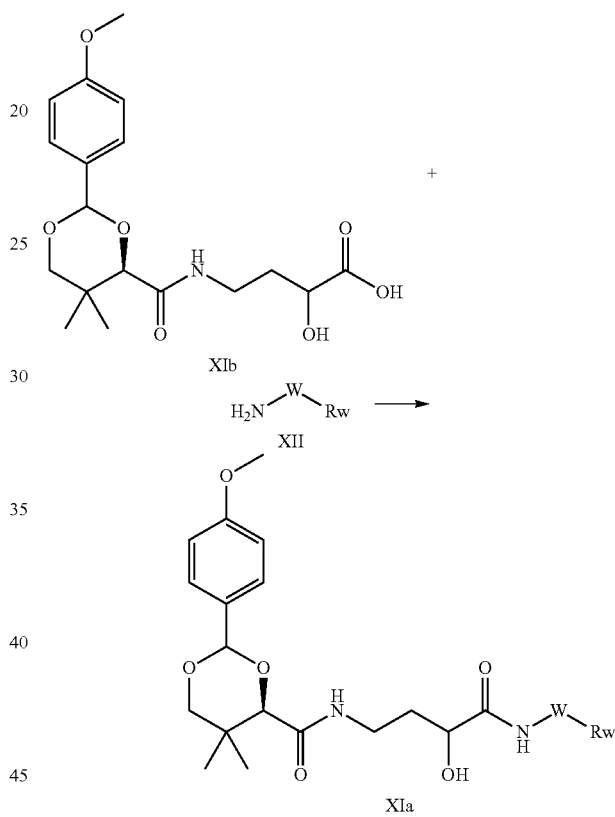

To a solution of compound of Formulae (XIb) (1 eq) in DMF (15 vol) were added amine of Formula (XII) (1 eq), N-methyl morpholine (3 eq) and HATU (1.1 eq) and heated at 100° C. under microwave radiation for 1 h. After this time, the reaction mixture was diluted with water and extracted with EtOAc. The combined organic layers were washed with brine, dried over Na$_2$SO$_4$ and concentrated under reduced pressure to get the crude product which was purified by silica gel column chromatography to afford the title compound.

General Procedure F: Synthesis of Ethylene Diamine Derivatives

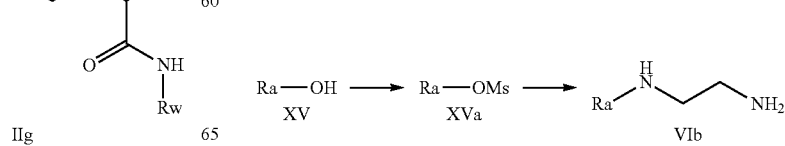

Step 1:

To a solution of the compound of Formula (XV) (1 eq) in dry DCM (50 vol) at 0° C. was added Et₃N (1.2 eq) followed by methane sulfonyl chloride (1.1 eq) and stirred for 1 h at 0° C. After completion of the reaction, it was diluted with water and extracted with DCM. The combined organic layer was washed with brine, dried over Na₂SO₄ and concentrated under reduced pressure to get the title compound which was taken as such to the next step.

Step 2:

To a solution of the compound of Formula (XVa) (1 eq) in MeOH (5 vol) was added ethylene diamine (3.6 vol) and stirred at room temperature for 16 h. After completion of the reaction, the solvents were removed under reduced pressure to get the crude compound which was purified by silica gel column chromatography to get the title compound.

General Procedure G: Pantolactone Opening

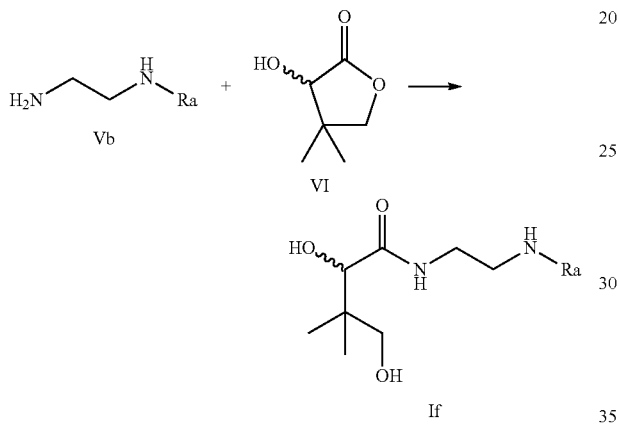

A microwave vial was charged with compound of Formula (Vb) (1 eq), D or L-pantolactone (1.5 eq) and EtOH (20 vol) and heated at 120° C. under microwave radiation for 2 h. After completion of the reaction the solvent was removed under reduced pressure and purified by silica gel column chromatography to get the title compound.

General Procedure H: Chloroamide Synthesis

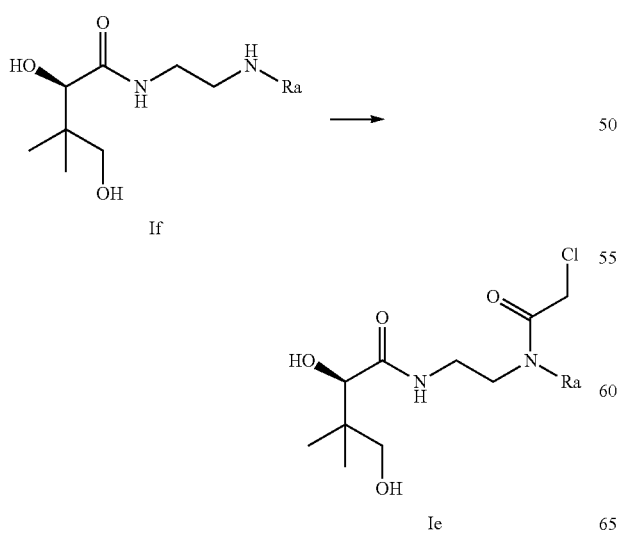

To a solution of the compound of Formula (If) (1 eq) in dry DCM (25 vol) at 0° C. was added Et₃N (3.5 eq) followed by chloroacetyl chloride (3.5 eq) and stirred for 1 h at the same temperature. After completion of the reaction, it was diluted with water and extracted with DCM. The combined organic layer was washed with brine, dried over Na₂SO₄ and concentrated under reduced pressure. The solid residue was dissolved in THF:H₂O (20 vol) and 10% NaOH (5 eq) was added dropwise at 0° C. and slowly brought to RT. After completion of the reaction, the solvent was removed under vacuum and extracted with EtOAc. The combined organic layer was washed with brine, dried over Na₂SO₄, concentrated under reduced pressure and purified by silica gel column chromatography to get the title compound.

Preparation of Intermediates

Intermediate A1: (R)-2,2,5,5-Tetramethyl-[1,3]dioxane-4-carboxylic acid (3-oxo-propyl)-amide Step 1: (R)-2,4-Dihydroxy-N-(3-hydroxy-propyl)-3,3-dimethyl-butyramide

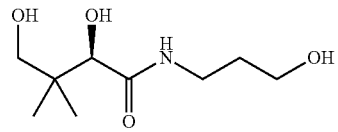

To a solution of D-pantolactone (0.5 g, 1 eq) in dry EtOH (5 mL) in a microwave vial were added 3-amino-propan-1-ol (0.53 mL, 1.5 eq) and Et₃N (0.54 mL, 1 eq) and irradiated with MW radiation at 160° C. for 3 h. After this time, the reaction mixture was concentrated and purified by silica gel column chromatography to afford the product as a white solid (800 mg, 95%).

¹H NMR (400 MHz, DMSO d₆): δ 7.70 (t, J=4.0 Hz, 1H), 5.32 (d, J=4.0 Hz, 1H), 4.48-4.42 (m, 2H), 3.68 (d, J=8.0 Hz, 1H), 3.40 (dd, J=4.0, 8.0 Hz, 2H), 3.31-3.26 (m, 1H), 3.19-3.07 (m, 3H), 2.56-2.52 (m, 2H), 0.78 (s, 3H), 0.76 (s, 3H).

Step 2: (R)-2,2,5,5-Tetramethyl-[1,3]dioxane-4-carboxylic acid (3-hydroxy-propyl)-amide

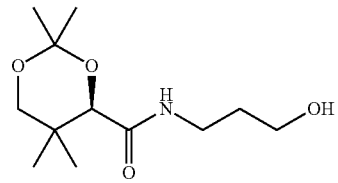 [SMILES: CC1(C)OCC(C)(C)[C@H](C(=O)NCCCO)O1]

To a solution of (R)-2,4-dihydroxy-N-(3-hydroxy-propyl)-3,3-dimethyl-butyramide (1 eq) in dry acetone (20 vol) were added 4 Å molecular sieves (200 wt %) followed by a slow addition of PTSA (0.05 eq) at 0° C. after which it was stirred at RT for 3 days. After completion of the reaction, the solvent was removed under vacuum and the crude product was purified by flash silica gel column chromatography (CHCl₃/MeOH) to afford the title compound which was taken forward for the next step.

LCMS (Method A, ELSD): 246.2 (M+H)

Step 3: (R)-2,2,5,5-Tetramethyl-[1,3]dioxane-4-carboxylic acid (3-oxo-propyl)-amide

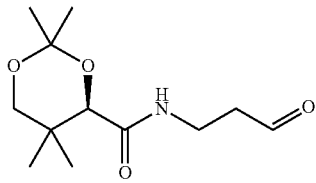 [SMILES: CC1(C)OCC(C)(C)[C@H](C(=O)NCCC=O)O1]

To a solution of (R)-2,2,5,5-tetramethyl-[1,3] dioxane-4-carboxylic acid (3-hydroxy-propyl)-amide (1 eq) in DCM (250 mL, 10 vol) was added Dess-Martin periodinane (1.5 eq) at 0° C. and the reaction mixture was stirred at RT for 6 h. After this time, the solvent was removed under vacuum and the solid residue was washed with MTBE and filtered. The filtrate was partitioned between EtOAc and a saturated aqueous solution of NaHCO$_3$. The organic layer was dried over Na$_2$SO$_4$ and concentrated. The crude product was purified by silica gel column chromatography (petroleum ether: EtOAc) to afford the title compound as a white solid (1.5 g, 55%).

LCMS (Method A): 244.2 (M+H). $^1$H NMR (400 MHz, DMSO-d$_6$): δ 9.63 (t, J=1.7 Hz, 1H), 7.53 (t, J=5.7 Hz, 1H), 4.01 (s, 1H), 3.63-3.44 (m, 1H), 3.42-3.36 (m, 1H), 3.33-3.27 (m, 1H), 3.17 (d, J=4.4 Hz, 1H), 2.58-2.48 (m, 2H), 1.40-1.42 (m, 6H), 0.90-0.94 (m, 6H).

Intermediate A2: (R)-2,2,5,5-Tetramethyl-[1,3]dioxane-4-carboxylic acid (3-hydroxy-butyl)-amide

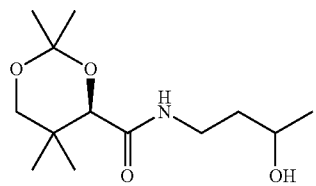 [SMILES: CC(O)CCNC(=O)[C@@H]1OC(C)(C)OCC1(C)C]

To a solution of (R)-2,2,5,5-tetramethyl-[1,3]dioxane-4-carboxylic acid (3-oxo-propyl)-amide (244 mg, 1 mmol) in dry THF (10 mL) at 0° C. was added MeMgBr (1.2 mL, 1.0 M solution in THF) and stirred at the same temperature for 1 h after which it was allowed to return to RT and stirred for another hour. After this time, it was quenched with a saturated aqueous solution of NH$_4$Cl and concentrated under reduced pressure. The aqueous layer was extracted with EtOAc and the combined organic layer was washed with brine, dried over anhydrous Na$_2$SO$_4$, concentrated under vacuum and purified by silica gel column chromatography to give the title compound as a colorless gum (130 mg, 50%).

LCMS (Method A): 260.2 (M+H).

Intermediate A3: (R)-2,2,5,5-Tetramethyl-[1,3]dioxane-4-carboxylic acid (3-hydroxy-pentyl)-amide

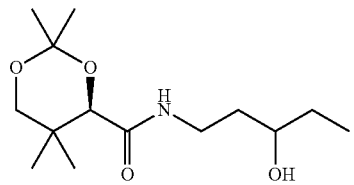 [SMILES: CCC(O)CCNC(=O)[C@@H]1OC(C)(C)OCC1(C)C]

(R)-2,2,5,5-Tetramethyl-[1,3]dioxane-4-carboxylic acid (3-hydroxy-pentyl)-amide was prepared following the procedure described for intermediate A2 from (R)-2,2,5,5-tetramethyl-[1,3]dioxane-4-carboxylic acid (3-oxo-propyl)-amide (242 mg, 1 mmol) and EtMgBr (1.2 mL, 1 M solution in THF) as a colorless liquid (120 mg, 45%).

LCMS (Method A, ELSD): 274.3 (M+H).

Intermediate A4: (R)-2,2,5,5-Tetramethyl-[1,3]dioxane-4-carboxylic acid (3-hydroxy-pent-4-enyl)-amide

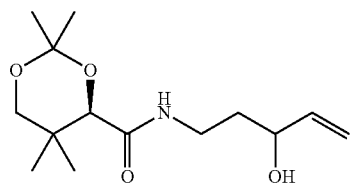 [SMILES: C=CC(O)CCNC(=O)[C@@H]1OC(C)(C)OCC1(C)C]

(R)-2,2,5,5-Tetramethyl-[1,3]dioxane-4-carboxylic acid (3-hydroxy-pent-4-enyl)-amide was prepared following the procedure described for intermediate A2 from (R)-2,2,5,5-tetramethyl-[1,3]dioxane-4-carboxylic acid (3-oxo-propyl)-amide (244 mg, 1 mmol) and vinyl magnesium bromide (1.2 mL, 1 M solution in THF) as a colorless liquid (142 mg, 52%).

LCMS (Method A, ELSD): 272.3 (M+H).

Intermediate A5: (S)-2,2,5,5-Tetramethyl-[1,3]dioxane-4-carboxylic acid (3-oxo-propyl)-amide

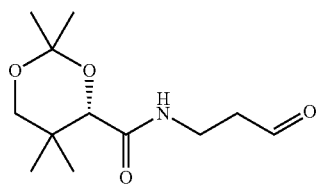 [SMILES: CC1(C)OCC(C)(C)[C@@H](C(=O)NCCC=O)O1]

(S)-2,2,5,5-Tetramethyl-[1,3]dioxane-4-carboxylic acid (3-oxo-propyl)-amide was synthesized following the same procedure as intermediate A1 starting from L-pantolactone (0.5 g, 1 eq) to afford the title compound as a white solid (0.67 g, 72%).

LCMS (Method A): 244.2 (M+H). $^1$H NMR (400 MHz, DMSO-d$_6$): δ 9.63 (t, J=1.7 Hz, 1H), 7.53 (t, J=5.7 Hz, 1H), 4.01 (s, 1H), 3.63-3.44 (m, 1H), 3.42-3.36 (m, 1H), 3.33-

3.27 (m, 1H), 3.17 (d, J=4.4 Hz, 1H), 2.58-2.48 (m, 2H), 1.40-1.42 (m, 6H), 0.90-0.94 (m, 6H).

Intermediate B1:
1-Isocyanomethyl-3-trifluoromethoxy-benzene

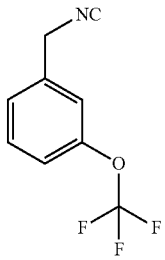

1-Isocyanomethyl-3-trifluoromethoxy-benzene was prepared following the general procedure C from 3-trifluoromethoxy-benzylamine (382 mg, 2 mmol) as a pale yellow liquid.
LCMS (Method A, ELSD): 202.2 (M+H).

Intermediate B2:
1-Isocyanomethyl-4-methanesulfonyl-benzene

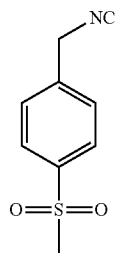

1-Isocyanomethyl-4-methanesulfonyl-benzene was prepared following the general procedure C from 4-methyl sulfonyl benzylamine (2 mmol) as a pale yellow liquid.
LCMS (Method A, ELSD): 196.2 (M+H).

Intermediate C1: (R)-2,2,5,5-Tetramethyl-[1,3]dioxane-4-carboxylic acid (3-cyclopropyl carbamoyl-3-hydroxy-propyl)-amide

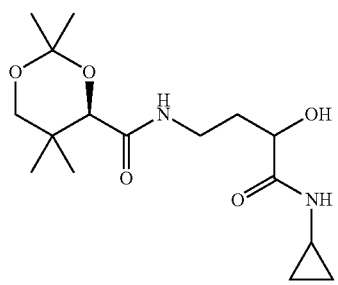 [SMILES: CC1(C)OCC(C)(C)[C@H](C(=O)NCCC(O)C(=O)NC2CC2)O1]

(R)-2,2,5,5-Tetramethyl-[1,3]dioxane-4-carboxylic acid (3-cyclopropyl carbamoyl-3-hydroxy-propyl)-amide was prepared following the general procedure D from (R)-2,2,5,5-tetramethyl-[1,3]dioxane-4-carboxylic acid (3-oxo-propyl)-amide (243 mg, 1 mmol) and cyclopropyl isocyanide (74 mg, 1.1 mmol) as a colorless liquid (267 mg, 81%).
LCMS (Method A): 329.2 (M+H).

Intermediate C2: (R)-2,2,5,5-Tetramethyl-[1,3]dioxane-4-carboxylic acid (3-benzylcarbamoyl-3-hydroxy-propyl)-amide

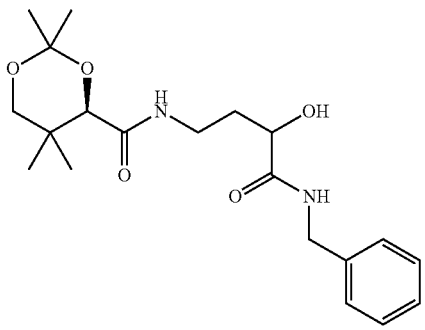 [SMILES: CC1(C)OCC(C)(C)[C@H](C(=O)NCCC(O)C(=O)NCc2ccccc2)O1]

(R)-2,2,5,5-Tetramethyl-[1,3]dioxane-4-carboxylic acid (3-benzylcarbamoyl-3-hydroxy-propyl)-amide was prepared following the general procedure D from (R)-2,2,5,5-tetramethyl-[1,3]dioxane-4-carboxylic acid (3-oxo-propyl)-amide (243 mg, 1 mmol) and benzylisocyanide (129 mg, 1.1 mmol) as a colorless liquid (242 mg, 64%).
LCMS (Method A, ELSD): 379.2 (M+H).

Intermediate C3: (R)-2,2,5,5-Tetramethyl-[1,3]dioxane-4-carboxylic acid [3-(2-fluoro-benzylcarbamoyl)-3-hydroxy-propyl]-amide

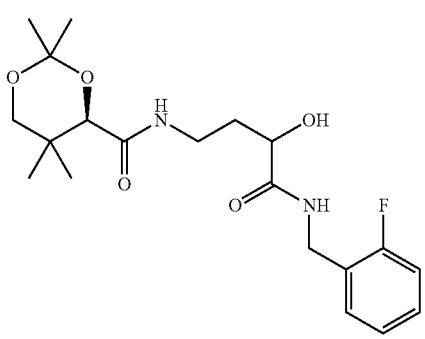 [SMILES: CC1(C)OCC(C)(C)[C@H](C(=O)NCCC(O)C(=O)NCc2ccccc2F)O1]

(R)-2,2,5,5-Tetramethyl-[1,3]dioxane-4-carboxylic acid [3-(2-fluoro-benzylcarbamoyl)-3-hydroxy-propyl]-amide was prepared following the procedure D from (R)-2,2,5,5-tetramethyl-[1,3]dioxane-4-carboxylic acid (3-oxo-propyl)-amide (243 mg, 1 mmol) and 2-fluorobenzylisocyanide (148 mg, 1.1 mmol) as a colorless liquid (253 mg, 63%).
LCMS (Method A, ELSD): 397.2 (M+H).

Intermediate C4: (R)-2,2,5,5-Tetramethyl-[1,3]dioxane-4-carboxylic acid [3-(cyclohexylmethyl-carbamoyl)-3-hydroxy-propyl]-amide

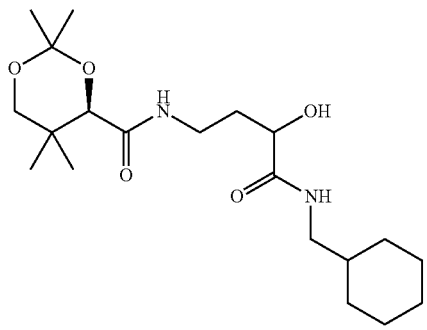 [SMILES: CC1(C)OCC(C)(C)[C@H](C(=O)NCCC(O)C(=O)NCC2CCCCC2)O1]

(R)-2,2,5,5-Tetramethyl-[1,3]dioxane-4-carboxylic acid [3-(cyclohexylmethyl-carbamoyl)-3-hydroxy-propyl]-amide was prepared following the procedure D from (R)-2,2,5,5-tetramethyl-[1,3]dioxane-4-carboxylic acid (3-oxo-propyl)-amide (243 mg, 1 mmol) and isocyanomethyl-cyclohexane (135 mg, 1.1 mmol) as a colorless liquid (278 mg, 72%).

LCMS (Method A, ELSD): 385.2 (M+H).

Intermediate C5: (R)-2,2,5,5-Tetramethyl-[1,3]dioxane-4-carboxylic acid (3-hydroxy-3-phenethylcarbamoyl-propyl)-amide

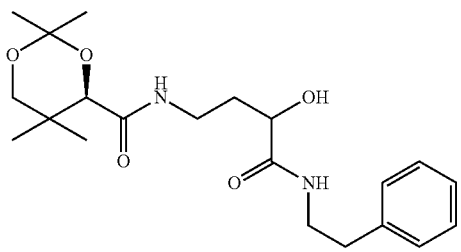 [SMILES: CC1(C)OCC(C)(C)[C@H](C(=O)NCCC(O)C(=O)NCCc2ccccc2)O1]

(R)-2,2,5,5-Tetramethyl-[1,3]dioxane-4-carboxylic acid (3-hydroxy-3-phenethylcarbamoyl-propyl)-amide was prepared following the procedure D from (R)-2,2,5,5-tetramethyl-[1,3]dioxane-4-carboxylic acid (3-oxo-propyl)-amide (243 mg, 1 mmol) and phenylethyl isocyanide (144 mg, 1.1 mmol) as a colorless liquid (267 mg, 68%).

LCMS (Method A, ELSD): 393.3 (M+H).

Intermediate C6: (S)-2,2,5,5-Tetramethyl-[1,3]dioxane-4-carboxylic acid (3-benzylcarbamoyl-3-hydroxy-propyl)-amide

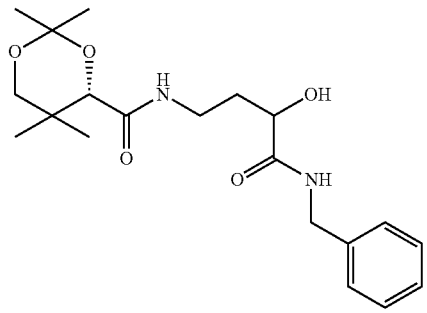 [SMILES: CC1(C)OCC(C)(C)[C@@H](C(=O)NCCC(O)C(=O)NCc2ccccc2)O1]

(S)-2,2,5,5-Tetramethyl-[1,3]dioxane-4-carboxylic acid (3-benzylcarbamoyl-3-hydroxy-propyl)-amide was prepared following the procedure D from (S)-2,2,5,5-tetramethyl-[1,3]dioxane-4-carboxylic acid (3-oxo-propyl)-amide (243 mg, 1 mmol) and benzyl isocyanide (129 mg, 1.1 mmol) as a colorless liquid (242 mg, 64%).

LCMS (Method A, ELSD): 379.2 (M+H).

Intermediate C7: (R)-2,2,5,5-Tetramethyl-[1,3]dioxane-4-carboxylic acid [3-hydroxy-3-(2-thiophen-2-yl-ethylcarbamoyl)-propyl]-amide

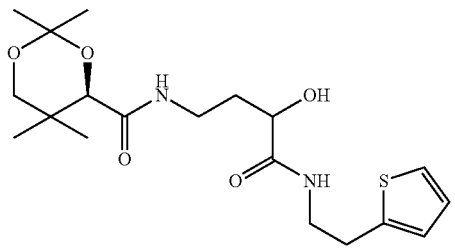 [SMILES: CC1(C)OCC(C)(C)[C@H](C(=O)NCCC(O)C(=O)NCCc2cccs2)O1]

(R)-2,2,5,5-Tetramethyl-[1,3]dioxane-4-carboxylic acid [3-hydroxy-3-(2-thiophen-2-yl-ethylcarbamoyl)-propyl]-amide was prepared following the procedure D from (R)-2,2,5,5-tetramethyl-[1,3]dioxane-4-carboxylic acid (3-oxo-propyl)-amide (243 mg, 1 mmol) and 2-(thien-2-yl)ethyl isocyanide (150 mg, 1.1 mmol) as a colorless liquid (191 mg, 48%).

LCMS (Method A): 399.2 (M+H).

Intermediate C8: (R)-2,2,5,5-Tetramethyl-[1,3]dioxane-4-carboxylic acid [3-hydroxy-3-(3-trifluoro methoxy-benzylcarbamoyl)-propyl]-amide

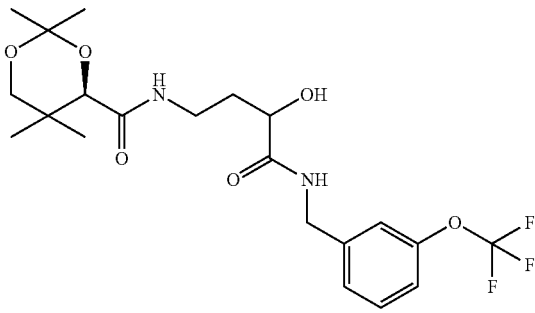 [SMILES: CC1(C)OCC(C)(C)[C@H](C(=O)NCCC(O)C(=O)NCc2cccc(OC(F)(F)F)c2)O1]

(R)-2,2,5,5-Tetramethyl-[1,3]dioxane-4-carboxylic acid [3-hydroxy-3-(3-trifluoro methoxy-benzylcarbamoyl)-propyl]-amide was prepared following the procedure D from (R)-2,2,5,5-tetramethyl-[1,3]dioxane-4-carboxylic acid (3-oxo-propyl)-amide (243 mg, 1 mmol) and 1-isocyano methyl-3-trifluoro methoxy-benzene (220 mg, 1.1 mmol) as a colorless liquid (311 mg, 67%).

LCMS (Method A, ELSD): 463.3 (M+H).

Intermediate C9: (R)-2,2,5,5-Tetramethyl-[1,3]dioxane-4-carboxylic acid (3-hydroxy-3-phenyl carbamoyl-propyl)-amide

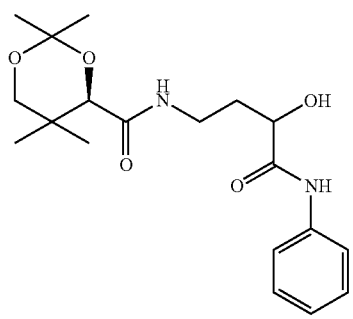 [SMILES: CC1(C)OCC(C)(C)[C@H](C(=O)NCCC(O)C(=O)Nc2ccccc2)O1]

(R)-2,2,5,5-Tetramethyl-[1,3]dioxane-4-carboxylic acid (3-hydroxy-3-phenyl carbamoyl-propyl)-amide was prepared following the procedure D from (R)-2,2,5,5-tetramethyl-[1,3]dioxane-4-carboxylic acid (3-oxo-propyl)-amide (243 mg, 1 mmol) and phenylisocyanate (113 mg, 1.1 mmol) as a colorless liquid (212 mg, 58%).

LCMS (Method A): 365.3 (M+H).

Intermediate C10: (R)-2,2,5,5-Tetramethyl-[1,3]dioxane-4-carboxylic acid [3-(4-fluoro-benzylcarbamoyl)-3-hydroxy-propyl]-amide

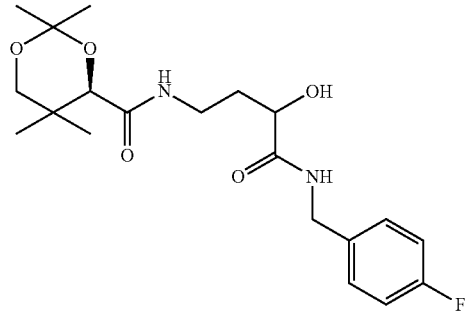 [SMILES: CC1(C)OCC(C)(C)[C@H](C(=O)NCCC(O)C(=O)NCc2ccc(F)cc2)O1]

(R)-2,2,5,5-Tetramethyl-[1,3]dioxane-4-carboxylic acid [3-(4-fluoro-benzylcarbamoyl)-3-hydroxy-propyl]-amide was prepared following the procedure D from (R)-2,2,5,5-tetramethyl-[1,3]dioxane-4-carboxylic acid (3-oxo-propyl)-amide (243 mg, 1 mmol) and 4-fluoro benzylisocyanide (148 mg, 1.1 mmol) as a colorless liquid (254 mg, 64%).

LCMS (Method A, ELSD): 397.2 (M+H).

Intermediate C11: (R)-2,2,5,5-Tetramethyl-[1,3]dioxane-4-carboxylic acid (3-cyclohexylcarbamoyl-3-hydroxy-propyl)-amide

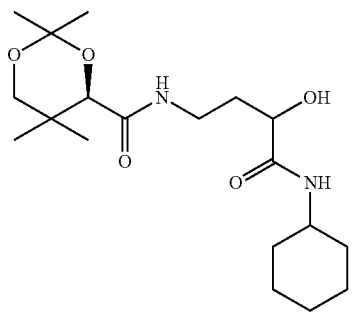 [SMILES: CC1(C)OCC(C)(C)[C@H](C(=O)NCCC(O)C(=O)NC2CCCCC2)O1]

(R)-2,2,5,5-Tetramethyl-[1,3]dioxane-4-carboxylic acid (3-cyclohexylcarbamoyl-3-hydroxy-propyl)-amide was prepared following the procedure D from (R)-2,2,5,5-tetramethyl-[1,3]dioxane-4-carboxylic acid (3-oxo-propyl)-amide (243 mg, 1 mmol) and cyclohexyl isocyanide (119 mg, 1.1 mmol) as a colorless liquid (215 mg, 54%).

LCMS (Method A, ELSD): 397.2 (M+H).

Intermediate C12: (R)-2,2,5,5-Tetramethyl-[1,3]dioxane-4-carboxylic acid {3-hydroxy-3-[(naphthalen-1-ylmethyl)-carbamoyl]-propyl}-amide

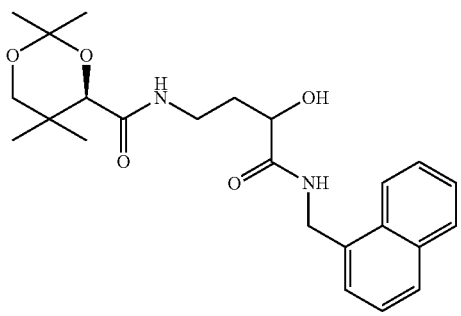 [SMILES: CC1(C)OCC(C)(C)[C@H](C(=O)NCCC(O)C(=O)NCc2cccc3ccccc23)O1]

(R)-2,2,5,5-Tetramethyl-[1,3]dioxane-4-carboxylic acid {3-hydroxy-3-[(naphthalen-1-ylmethyl)-carbamoyl]-propyl}-amide was prepared following the procedure D from (R)-2,2,5,5-tetramethyl-[1,3] dioxane-4-carboxylic acid (3-oxo-propyl)-amide (243 mg, 1 mmol) and 1-naphthalenemethylisocyanide (184 mg, 1.1 mmol) as a colorless liquid (295 mg, 68%).

LCMS (Method A, ELSD): 429.2 (M+H).

Intermediate C13: (R)-2,2,5,5-Tetramethyl-[1,3]dioxane-4-carboxylic acid [3-hydroxy-3-(1-phenyl-ethylcarbamoyl)-propyl]-amide

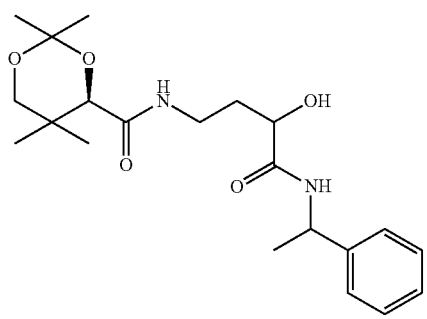 [SMILES: CC(NC(=O)C(O)CCNC(=O)[C@@H]1OC(C)(C)OCC1(C)C)c1ccccc1]

(R)-2,2,5,5-Tetramethyl-[1,3]dioxane-4-carboxylic acid [3-hydroxy-3-(1-phenyl-ethylcarbamoyl)-propyl]amide was prepared following the procedure D from (R)-2,2,5,5-tetramethyl-[1,3] dioxane-4-carboxylic acid (3-oxo-propyl)-amide (243 mg, 1 mmol) and alpha methyl benzylisocyanide (144 mg, 1.1 mmol) as a colorless liquid (224 mg, 57%).

LCMS (Method A, ELSD): 393.2 (M+H).

Intermediate C14: (R)-2,2,5,5-Tetramethyl-[1,3]dioxane-4-carboxylic acid [3-(benzhydryl-carbamoyl)-3-hydroxy-propyl]-amide

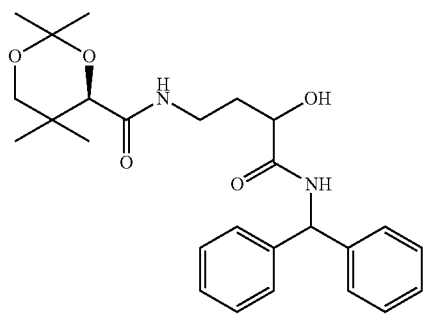 [SMILES: CC1(C)OCC(C)(C)[C@H](C(=O)NCCC(O)C(=O)NC(c2ccccc2)c2ccccc2)O1]

(R)-2,2,5,5-Tetramethyl-[1,3]dioxane-4-carboxylic acid [3-(benzhydryl-carbamoyl)-3-hydroxy-propyl]-amide was prepared following the procedure D from (R)-2,2,5,5-tetramethyl-[1,3] dioxane-4-carboxylic acid (3-oxo-propyl)-amide (243 mg, 1 mmol) and diphenylmethylisocyanide (212 mg, 1.1 mmol) as a colorless liquid (308 mg, 68%).

LCMS (Method A, ELSD): 454.2 (M+H).

Intermediate C15: (R)-2,2,5,5-Tetramethyl-[1,3]dioxane-4-carboxylic acid [3-hydroxy-3-(3-methoxy-benzylcarbamoyl)-propyl]-amide

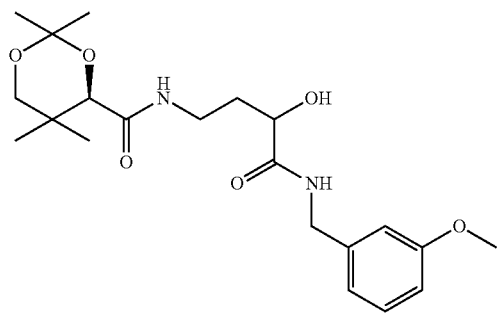 [SMILES: COc1cccc(CNC(=O)C(O)CCNC(=O)[C@@H]2OC(C)(C)OCC2(C)C)c1]

(R)-2,2,5,5-Tetramethyl-[1,3]dioxane-4-carboxylic acid [3-hydroxy-3-(3-methoxy-benzylcarbamoyl)-propyl]-amide was prepared following the procedure D from (R)-2,2,5,5-tetramethyl-[1,3] dioxane-4-carboxylic acid (3-oxo-propyl)-amide (243 mg, 1 mmol) and 3-methoxybenzylisocyanide (161 mg, 1.1 mmol) as a colorless liquid (196 mg, 48%).

LCMS (Method A, ELSD): 408.2 (M+H).

Intermediate C16: (R)-2,2,5,5-Tetramethyl-[1,3]dioxane-4-carboxylic acid [3-hydroxy-3-(2-trifluoromethyl-benzylcarbamoyl)-propyl]-amide

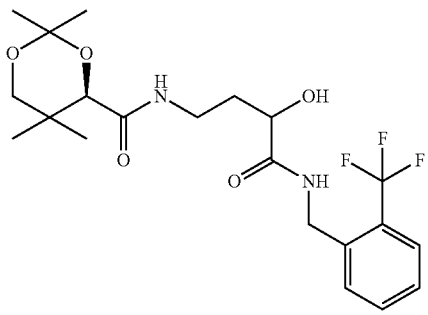 [SMILES: CC1(C)OCC(C)(C)[C@H](C(=O)NCCC(O)C(=O)NCc2ccccc2C(F)(F)F)O1]

(R)-2,2,5,5-Tetramethyl-[1,3]dioxane-4-carboxylic acid [3-hydroxy-3-(2-trifluoromethyl-benzylcarbamoyl)-propyl]-amide was prepared following the procedure D from (R)-2,2,5,5-tetramethyl-[1,3] dioxane-4-carboxylic acid (3-oxo-propyl)-amide (243 mg, 1 mmol) and 2-trifluoromethyl benzylisocyanide (203 mg, 1.1 mmol) as a colorless liquid (219 mg, 48%).

LCMS (Method A, ELSD): 447.2 (M+H).

Intermediate C17: (R)-2,2,5,5-Tetramethyl-[1,3]dioxane-4-carboxylic acid [3-hydroxy-3-(4-methane sulfonyl-benzyl carbamoyl)-propyl]-amide

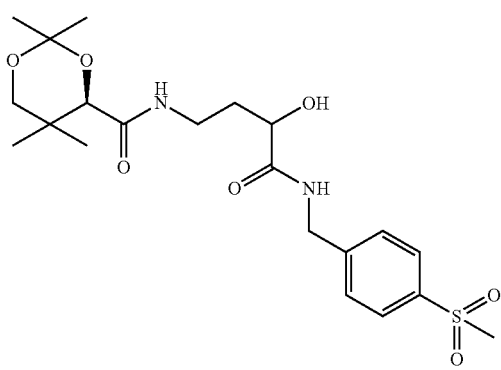 [SMILES: CC1(C)OCC(C)(C)[C@H](C(=O)NCCC(O)C(=O)NCc2ccc(S(C)(=O)=O)cc2)O1]

(R)-2,2,5,5-Tetramethyl-[1,3]dioxane-4-carboxylic acid [3-hydroxy-3-(4-methane sulfonyl-benzyl carbamoyl)-propyl]-amide was prepared following the procedure D from (R)-2,2,5,5-tetramethyl-[1,3] dioxane-4-carboxylic acid (3-oxo-propyl)-amide (243 mg, 1 mmol) and 1-isocyano methyl-4-methanesulfonyl-benzene (214 mg, 1.1 mmol) as a colorless liquid (206 mg, 45%).

LCMS (Method A): 457.2 (M+H).

Intermediate C18: {2-Hydroxy-4-[((R)-2,2,5,5-tetramethyl-[1,3]dioxane-4-carbonyl)-amino] butyryl amino}-acetic acid methyl ester

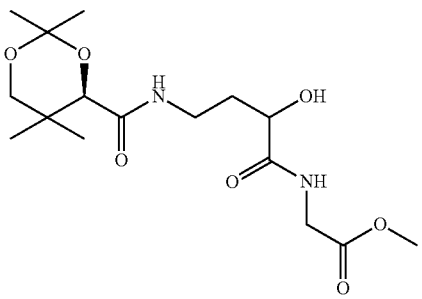 [SMILES: COC(=O)CNC(=O)C(O)CCNC(=O)[C@@H]1OC(C)(C)OCC1(C)C]

{2-Hydroxy-4-[((R)-2,2,5,5-tetramethyl-[1,3]dioxane-4-carbonyl)-amino]-butyryl amino}-acetic acid methyl ester was prepared following the procedure D from (R)-2,2,5,5-tetramethyl-[1,3] dioxane-4-carboxylic acid (3-oxo-propyl)-amide (243 mg, 1 mmol) and isocyano-acetic acid methyl ester (110 mg, 1 mmol) as a colorless liquid (185 mg, 51%).

LCMS (Method A): 361.3 (M+H).

Intermediate D1: 2-Hydroxy-4-{[(R)-2-(4-methoxy-phenyl)-5,5-dimethyl-[1,3]dioxane-4-carbonyl]-amino}-butyric acid

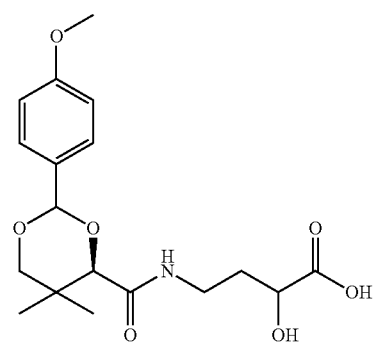

Step 1: 2-Hydroxy-4-{[(R)-2-(4-methoxy-phenyl)-5,5-dimethyl-[1,3]dioxane-4-carbonyl]-amino}-butyric acid ethyl ester To a solution of (R)-2-(4-Methoxy-phenyl)-5,5-dimethyl-[1,3]dioxane-4-carboxylic acid (12 g, 45.1 mmol) obtained following the procedure described in Journal Organic Letters, 2004, 6(26), 4801-4803 and diisopropylethylamine (78.6 mL, 0.375 mol) in dry DCM (200 mL) at 0° C. were added HOBt (21.9 g, 0.162 mol) and EDC.HCl (25.8 g, 0.135 mol) followed by ethyl 4-amino-2-hydroxybutanoate-.HCl (9 g, 49.6 mmol). The reaction mixture was stirred at 0° C. for 2 h and another 1 h at RT. After completion, it was extracted with DCM dried over Na$_2$SO$_4$, concentrated under reduced pressure and purified by silica gel column chromatography (DCM: MeOH, 8:1) to afford a colorless liquid (12 g, 67%).

LCMS (Method A, ELSD): 396.3 (M+H). $^1$H NMR (400 MHz, DMSO-d$_6$): δ 7.52 (t, J=5.9 Hz, 1H), 7.41 (d, J=6.6 Hz, 2H), 6.91 (d, J=4.8 Hz, 2H), 5.50 (s, 1H), 5.46 (d, J=5.6 Hz, 1H), 4.09-4.01 (m, 4H), 3.81 (s, 3H), 3.66-3.59 (m, 2H), 3.27-3.12 (m, 2H), 1.81-1.69 (m, 1H), 1.63-1.60 (m, 1H), 1.21 (t, J=7.1 Hz, 3H), 1.04 (s, 3H), 0.91 (s, 3H).

Step 2: 2-Hydroxy-4-{[(R)-2-(4-methoxy-phenyl)-5,5-dimethyl-[1, 3]dioxane-4-carbonyl]-amino}-butyric acid To a solution of 2-hydroxy-4-{[(R)-2-(4-methoxy-phenyl)-5,5-dimethyl-[1,3]dioxane-4-carbonyl]-amino}-butyric acid ethyl ester (10 g, 25.3 mmol) in THF:H$_2$O (1:1, 80 mL) was added LiOH.H$_2$O (3 g, 75.9 mmol) and it was stirred at 0° C. for 2 h and at RT for 1 h. After completion of the reaction, the solvent was removed under vacuum and the residue was diluted with water and EtOAc. The aqueous layer was then acidified to pH=6 and extracted with EtOAc. The combined organic layer was dried over Na$_2$SO$_4$ and concentrated under reduced pressure to get the title compound as a colorless gum (9 g, 99%).

LCMS (Method A): 368.3 (M+H). $^1$H NMR (400 MHz, DMSO-d$_6$): δ 7.51 (t, J=4.0 Hz, 1H), 7.44 (d, J=6.9 Hz, 2H), 6.92 (d, J=6.8 Hz, 2H), 5.51 (s, 1H), 4.07 (s, 1H), 3.95-3.94 (m, 1H), 3.75 (s, 3H), 3.65-3.61 (m, 2H), 3.33-3.13 (m, 2H), 1.90-1.82 (m, 1H), 1.61-1.53 (m, 1H), 1.01 (s, 3H), 0.94 (s, 3H).

Intermediate E1: (R)-2-(4-Methoxy-phenyl)-5,5-dimethyl-[1,3]dioxane-4-carboxylic acid {3-hydroxy-3-3-2-methanesulfonylamino-ethoxy)-benzyl-carbamoyl]-propyl}-amide

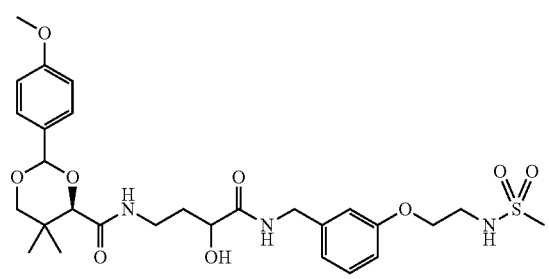

(R)-2-(4-Methoxy-phenyl)-5,5-dimethyl-[1,3]dioxane-4-carboxylic acid {3-hydroxy-3-3-2-methanesulfonylamino-ethoxy)-benzylcarbamoyl]-propyl}-amide was synthesized following the general procedure E from 2-hydroxy-4-{[(R)- 2-(4-methoxy-phenyl)-5,5-dimethyl-[1,3]dioxane-4-carbonyl]-amino}-butyric acid (367 mg, 1 mmol) and N-[2-(3-aminomethyl-phenoxy)-ethyl]-methane sulfonamide (243 mg, 1 mmol) as a colorless liquid (225 mg, 38%).

LCMS (Method A): 594.3 (M+H).

Intermediate E2: (R)-2-(4-Methoxy-phenyl)-5,5-dimethyl-[1,3]dioxane-4-carboxylic acid [3-(benzyl-ethyl-carbamoyl)-3-hydroxy-propyl]-amide

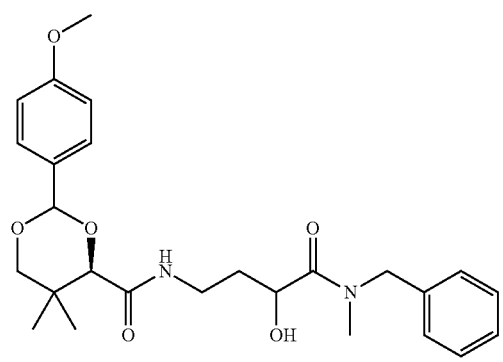

(R)-2-(4-Methoxy-phenyl)-5,5-dimethyl-[1,3]dioxane-4-carboxylic acid [3-(benzyl-ethyl-carbamoyl)-3-hydroxy-propyl]-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and benzyl-methyl-amine (120 mg, 1 mmol) as a pale yellow liquid (198 mg, 42%).

LCMS (Method A): 470.2 (M+H).

Intermediate E3: (R)-2-(4-Methoxy-phenyl)-5,5-dimethyl-[1,3]dioxane-4-carboxylic acid {3-[(biphenyl-4-lmethyl)-carbamoyl]-3-hydroxy-propyl}-amide

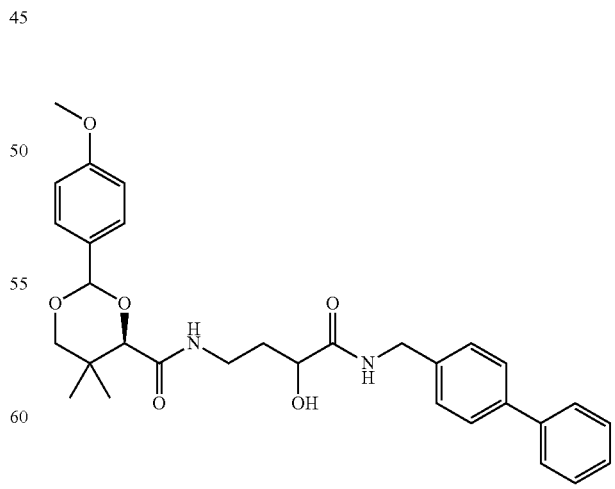

(R)-2-(4-Methoxy-phenyl)-5,5-dimethyl-[1,3]dioxane-4-carboxylic acid {3-[(biphenyl-4-Imethyl)-carbamoyl]-3-hydroxy-propyl}-amide was synthesized following the general procedure E from (2-hydroxy-4-{[(R)-2-(4-methoxy-phenyl)-5,5-dimethyl-[1,3]dioxane-4-carbonyl]-amino}-butyric acid (367 mg, 1 mmol) and biphenyl-4-yl-methylamine (182 mg, 1 mmol) as a pale yellow liquid (290 mg, 54%).

LCMS (Method A): 553.3 (M+H).

Intermediate E4: (R)-2-(4-Methoxy-phenyl)-5,5-dimethyl-[1,3]dioxane-4-carboxylic acid {3-hydroxy-3-(tetrahydro-furan-2-ylmethyl)-carbamoyl]-propyl}-amide

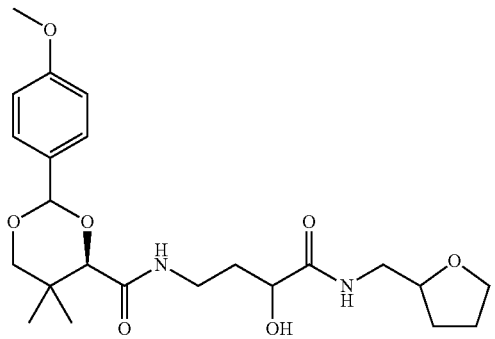

(R)-2-(4-Methoxy-phenyl)-5,5-dimethyl-[1,3]dioxane-4-carboxylic acid {3-hydroxy-3-(tetrahydro-furan-2-ylmethyl)-carbamoyl]-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and (tetrahydro-furan-2-yl)-methylamine (100 mg, 1 mmol) as a pale yellow liquid (215 mg, 48%).

LCMS (Method A): 451.2 (M+H). $^1$H NMR (400 MHz, DMSO-d$_6$): δ 7.7 (t, J=5.2 Hz, 1H), 7.5 (t, J=4.9 Hz, 1H), 7.4 (d, J=1.9 Hz, 2H), 6.9 (d, J=6.8 Hz, 2H), 5.7 (t, J=5.4 Hz, 1H), 5.5 (s, 1H), 4.1 (s, 1H), 3.8 (t, J=4.0 Hz, 2H), 3.8 (s, 3H), 3.73-3.58 (m, 4H), 3.15-3.10 (m, 4H), 1.90-1.77 (m, 4H), 1.60-1.42 (m, 2H), 1.0 (s, 3H), 0.9 (s, 3H).

Intermediate E5: (R)-2-(4-Methoxy-phenyl)-5,5-dimethyl-[1,3]dioxane-4-carboxylic acid {3-hydroxy-3-2-4-methanesulfonyl-phenyl)-ethylcarbamoyl]-propyl}-amide

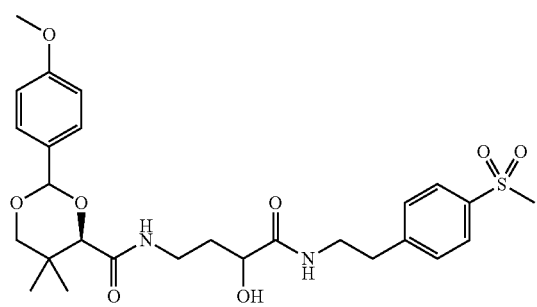

(R)-2-(4-Methoxy-phenyl)-5,5-dimethyl-[1,3]dioxane-4-carboxylic acid {3-hydroxy-3-2-4-methanesulfonyl-phenyl)-ethylcarbamoyl]-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 2-(4-methanesulfonyl-phenyl)-ethylamine (198 mg, 1 mmol) as a pale yellow liquid (310 mg, 57%).

LCMS (Method A): 549.3 (M+H).

Intermediate E6: (R)-2-(4-Methoxy-phenyl)-5,5-dimethyl-[1,3]dioxane-4-carboxylic acid [3-(4-bromo-benzylcarbamoyl)-3-hydroxy-propyl]-amide

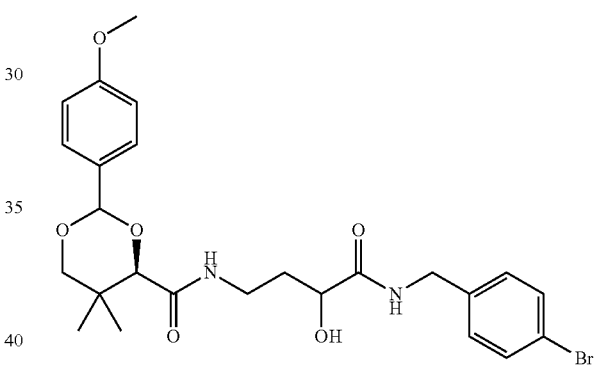

(R)-2-(4-Methoxy-phenyl)-5,5-dimethyl-[1,3]dioxane-4-carboxylic acid [3-(4-bromo-benzylcarbamoyl)-3-hydroxy-propyl]-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 4-bromo-benzylamine (185 mg, 1 mmol) as a pale yellow gummy liquid (285 mg, 62%).

LCMS (Method A): 536.0 (M+H). $^1$H NMR (400 MHz, DMSO-d$_6$): δ 8.4 (t, J=6.0 Hz, 1H), 7.52-7.47 (m, 3H), 7.2 (d, J=11.4 Hz, 2H), 5.7 (t, J=4.0 Hz, 1H), 4.2 (t, J=9.6 Hz, 2H), 4.0 (t, J=7.2 Hz, 1H), 3.9 (d, J=1.6 Hz, 1H), 3.6 (d, J=11.6 Hz, 1H), 3.19-3.16 (m, 4H), 1.91-1.79 (m, 1H), 1.65-1.52 (m, 1H), 1.4 (s, 6H), 1.0 (s, 3H), 0.8 (s, 3H).

Intermediate E7: (R)-2-(4-Methoxy-phenyl)-5,5-dimethyl-[1,3]dioxane-4-carboxylic acid (3-hydroxy-3-4-2-(4-phenoxy-phenyl)-ethylcarbamoyl]-benzylcarbamoyl}-propyl)-amide

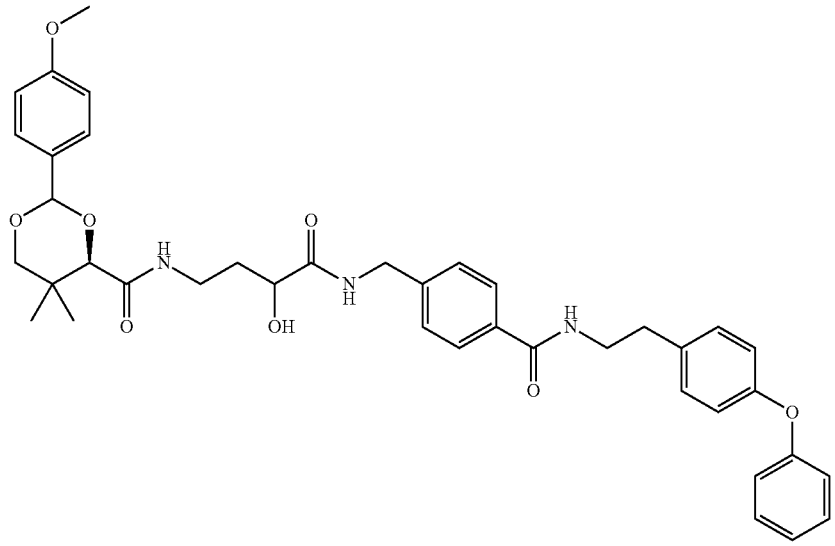

(R)-2-(4-Methoxy-phenyl)-5,5-dimethyl-[1,3]dioxane-4-carboxylic acid (3-hydroxy-3-4-2-(4-phenoxy-phenyl)-ethylcarbamoyl]-benzylcarbamoyl}-propyl)-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 2-(4-phenoxy-phenyl)-ethylamine (12 mg, 1 mmol) as a pale yellow liquid (375 mg, 67%).

LCMS (Method A): 563.3 (M+H).

Intermediate E8: (R)-2-(4-Methoxy-phenyl)-5,5-dimethyl-[1,3]dioxane-4-carboxylic acid {3-hydroxy-3-4-piperidine-1-sulfonyl)-benzylcarbamoyl}-propyl)-amide

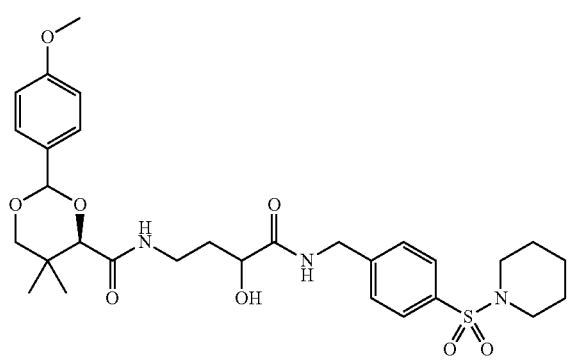

(R)-2-(4-Methoxy-phenyl)-5,5-dimethyl-[1,3]dioxane-4-carboxylic acid {3-hydroxy-3-4-piperidine-1-sulfonyl)-benzylcarbamoyl]-propyl)-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 4-(piperidine-1-sulfonyl)-benzylamine (253 mg, 1 mmol) as a pale yellow liquid (320 mg, 53%).

LCMS (Method A): 604.2 (M+H).

Intermediate E9: (R)-2-(4-Methoxy-phenyl)-5,5-dimethyl-[1,3]dioxane-4-carboxylic acid {3-[(1-benzenesulfonyl-piperidin-4-ylmethyl-carbamoyl]-3-hydroxy-propyl}-amide

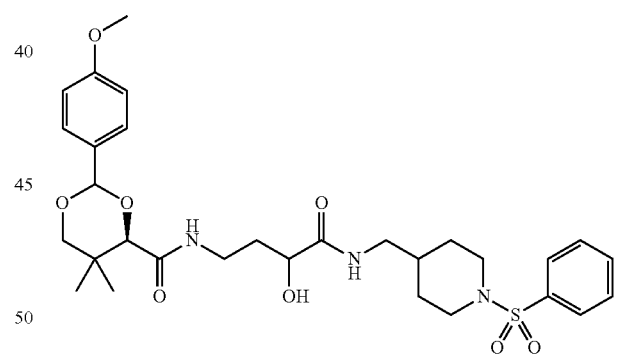

(R)-2-(4-Methoxy-phenyl)-5,5-dimethyl-[1,3]dioxane-4-carboxylic acid {3-[(1-benzenesulfonyl-piperidin-4-ylmethyl)-carbamoyl]-3-hydroxy-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (300 mg, 1 mmol) and (4-benzenesulfonyl-piperidinyl)-methylamine (243 mg, 1 mmol) as a pale yellow liquid (280 mg, 53%).

LCMS (Method A): 604.2 (M+H).

Intermediate E10: (R)-2-(4-Methoxy-phenyl)-5,5-dimethyl-[1,3]dioxane-4-carboxylic acid (3-hydroxy-3-3-3-(piperidine-1-sulfonyl)-phenyl]-propyl-carbamoyl}-propyl)-amide

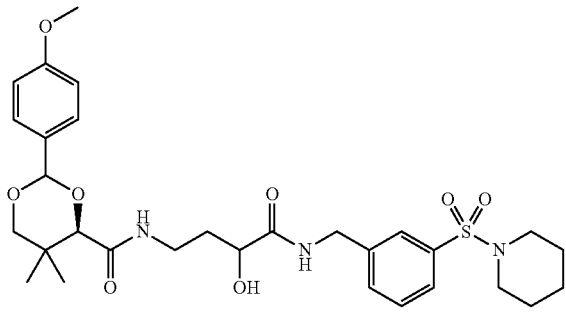

(R)-2-(4-Methoxy-phenyl)-5,5-dimethyl-[1,3]dioxane-4-carboxylic acid (3-hydroxy-3-3-3-(piperidine-1-sulfonyl)-phenyl]-propylcarbamoyl}-propyl)-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 3-[3-(piperidine-1-sulfonyl)-phenyl]-propylamine (281 mg, 1 mmol) as a pale yellow liquid (285 mg, 45%).

LCMS (Method A): 632.2 (M+H).

Intermediate E11: (R)-2-(4-Methoxy-phenyl)-5,5-dimethyl-[1,3]dioxane-4-carboxylic acid {3-hydroxy-3-3-piperidine-1-sulfonyl)-benzylcarbamoyl}-propyl)-amide

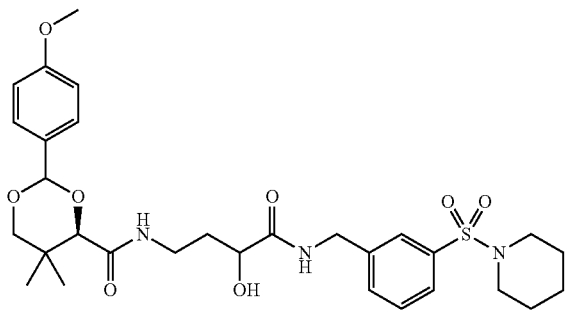

(R)-2-(4-Methoxy-phenyl)-5,5-dimethyl-[1,3]dioxane-4-carboxylic acid {3-hydroxy-3-3-piperidine-1-sulfonyl)-benzylcarbamoyl]-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 3-[3-(piperidine-1-sulfonyl)-benzyl amine (253 mg, 1 mmol) as a pale yellow liquid (315 mg, 52%).

LCMS (Method A): 604.2 (M+H).

Intermediate E12: (R)-2-(4-Methoxy-phenyl)-5,5-dimethyl-[1,3]dioxane-4-carboxylic acid {3-hydroxy-3-4-pyridin-4-yloxy)-benzylcarbamoyl]-propyl}amide

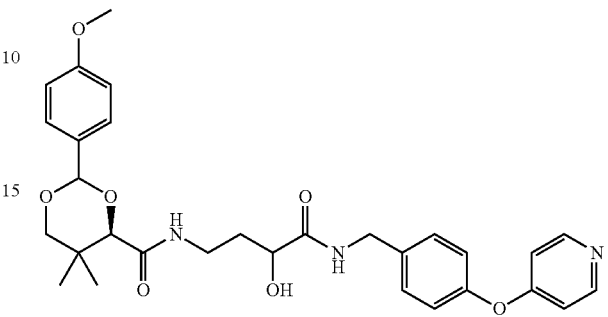

(R)-2-(4-Methoxy-phenyl)-5,5-dimethyl-[1,3]dioxane-4-carboxylic acid {3-hydroxy-3-4-pyridin-4-yloxy)-benzylcarbamoyl]-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 4-(pyridin-4-yloxy)-benzylamine (199 mg, 1 mmol) as a pale yellow gummy liquid (258 mg, 47%).

LCMS (Method A): 550.2 (M+H).

Intermediate E13: (R)-2-(4-Methoxy-phenyl)-5,5-dimethyl-[1,3]dioxane-4-carboxylic acid (3-{[1-(biphenyl-4-sulfonyl)-piperidin-4-ylmethyl]-carbamoyl}-3-hydroxy-propyl)-amide (R)-2-(4-Methoxy-phenyl)-5,5-dimethyl-[1,3]dioxane-4-carboxylic acid (3-{[1-(biphenyl-4-sulfonyl)-piperidin-4-ylmethyl]-carbamoyl}-3-hydroxy-propyl)-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 4-(pyridin-4-yloxy)-benzyl amine (329 mg, 1 mmol) as a pale yellow liquid (320 mg, 47%).

LCMS (Method A): 680.2 (M+H).

Intermediate E14: (R)-2-(4-Methoxy-phenyl)-5,5-dimethyl-[1,3]dioxane-4-carboxylic acid }3-hydroxy-3-[4-(2-methanesulfonylamino-ethoxy)-benzylcarbamoyl]-propyl}-amide

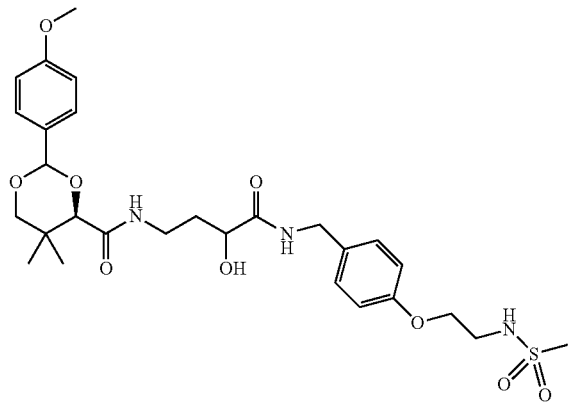

(R)-2-(4-Methoxy-phenyl)-5,5-dimethyl-[1,3]dioxane-4-carboxylic acid {3-hydroxy-3-[4-(2-methanesulfonylamino-ethoxy)-benzylcarbamoyl]-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 4-(pyridin-4-yloxy)-benzyl amine (243 mg, 1 mmol) as a pale yellow liquid (290 mg, 49%).

LCMS (Method A): 593.0 (M+H).

Intermediate E15: (R)-2-(4-Methoxy-phenyl)-5,5-dimethyl-[1,3]dioxane-4-carboxylic acid {3-hydroxy-3-3-3-oxo-morpholin-4-yl)-propylcarbamoyl]-propyl}-amide

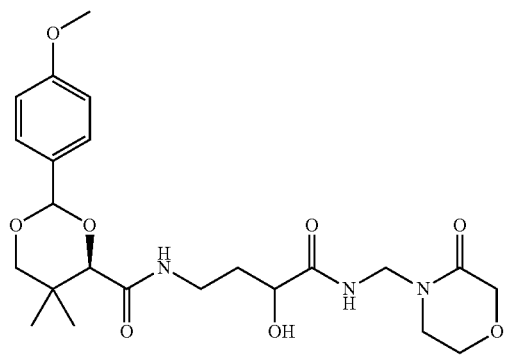

(R)-2-(4-Methoxy-phenyl)-5,5-dimethyl-[1,3]dioxane-4-carboxylic acid {3-hydroxy-3-3-3-oxo-morpholin-4-yl)-propylcarbamoyl]-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 4-(3-amino-propyl)-morpholin-3-one (157 mg, 1 mmol) as a pale yellow liquid (282 mg, 55%).

LCMS (Method A): 508.3 (M+H).

Intermediate E16: (R)-2-(4-Methoxy-phenyl)-5,5-dimethyl-[1,3]dioxane-4-carboxylic acid [3-hydroxy-3-(4-morpholin-4-yl-benzylcarbamoyl)-propyl]-amide

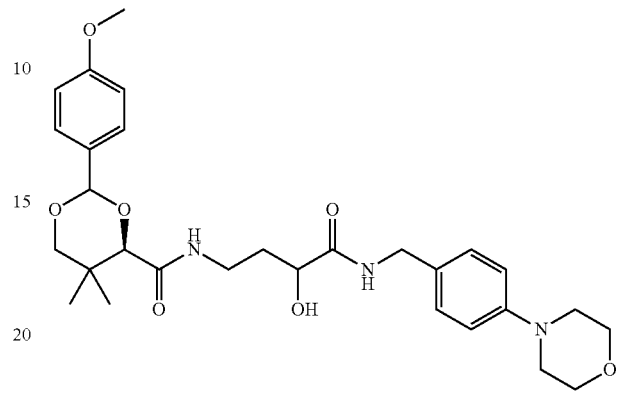

(R)-2-(4-Methoxy-phenyl)-5,5-dimethyl-[1,3]dioxane-4-carboxylic acid [3-hydroxy-3-(4-morpholin-4-yl-benzylcarbamoyl)-propyl]-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 4-(3-amino-propyl)-morpholin-3-one (191 mg, 1 mmol) as a pale yellow liquid (265 mg, 49%).

LCMS (Method A): 542.3 (M+H).

Intermediate E17: (R)-2-(4-Methoxy-phenyl)-5,5-dimethyl-[1,3]dioxane-4-carboxylic acid [3-hydroxy-3-(2-phenoxy-ethylcarbamoyl)-propyl]-amide

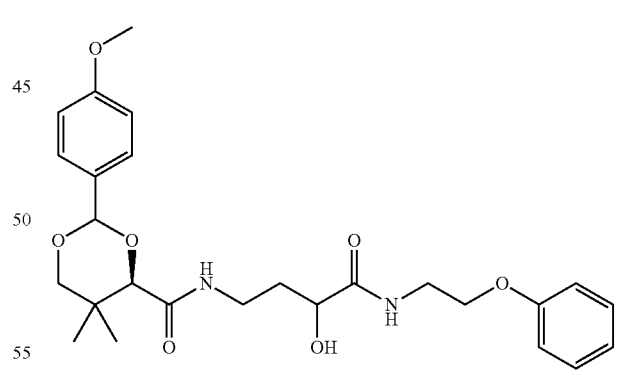

(R)-2-(4-Methoxy-phenyl)-5,5-dimethyl-[1,3]dioxane-4-carboxylic acid [3-hydroxy-3-(2-phenoxy-ethylcarbamoyl)-propyl]-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 2-phenoxy-ethylamine (136 mg, 1 mmol) as a pale yellow liquid (228 mg, 47%).

LCMS (Method A): 487.2 (M+H).

Intermediate E18: (R)-2-(4-Methoxy-phenyl)-5,5-dimethyl-[1,3]dioxane-4-carboxylic acid }3-hydroxy-4-oxo-4-[4-(3-trifluoromethanesulfonyl-phenylamino)-piperidin-1-yl]-butyl}-amide

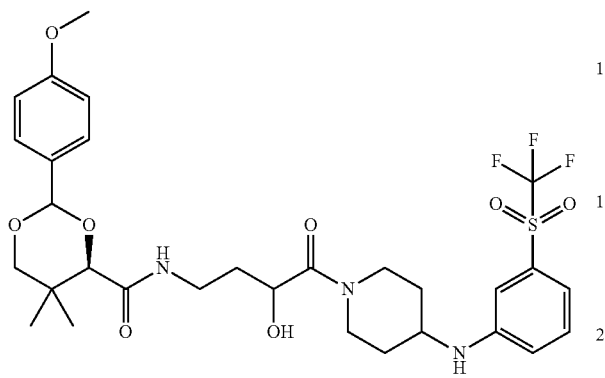

(R)-2-(4-Methoxy-phenyl)-5,5-dimethyl-[1,3]dioxane-4-carboxylic acid {3-hydroxy-4-oxo-4-[4-(3-trifluoromethanesulfonyl-phenylamino)-piperidin-1-yl]-butyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and piperidin-4-yl-(3-trifluoromethanesulfonyl-phenyl)-amine (307 mg, 1 mmol) as a pale yellow liquid (415 mg, 63%).

LCMS (Method A): 659.2 (M+H).

Intermediate E19: (R)-2-(4-Methoxy-phenyl)-5,5-dimethyl-[1,3]dioxane-4-carboxylic acid {3-hydroxy-3-4-2-morpholin-4-yl-ethoxy)-benzylcarbamoyl}-propyl)-amide

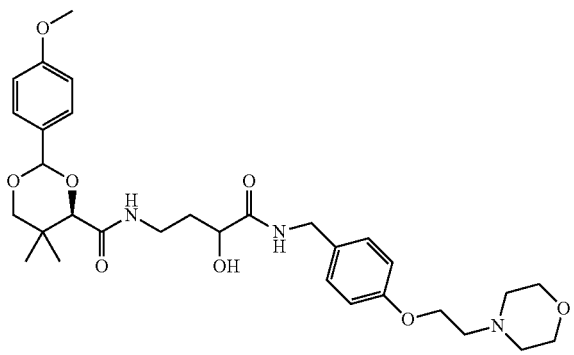

(R)-2-(4-Methoxy-phenyl)-5,5-dimethyl-[1,3]dioxane-4-carboxylic acid {3-hydroxy-3-4-2-morpholin-4-yl-ethoxy)-benzylcarbamoyl]-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 4-(2-morpholin-4-yl-ethoxy)-benzylamine (235 mg, 1 mmol) as a pale yellow liquid (340 mg, 58%).

LCMS (Method A): 584.2 (M+H).

Intermediate E20: 4-[(2-Hydroxy-4-{[(R)-2-(4-methoxy-phenyl)-5,5-dimethyl-[1,3]dioxane-4-carbonyl]-amino}-butyrylamino)-methyl]-benzoic acid ethyl ester

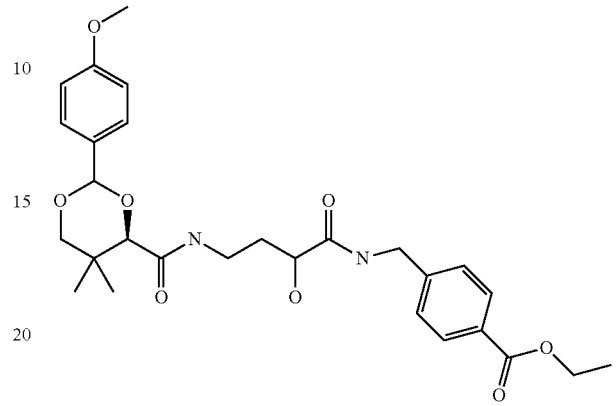

4-[(2-Hydroxy-4-{[(R)-2-(4-methoxy-phenyl)-5,5-dimethyl-[1,3]dioxane-4-carbonyl]-amino}-butyrylamino)-methyl]-benzoic acid ethyl ester was synthesized following the general procedure E from 2-hydroxy-4-{[(R)-2-(4-methoxy-phenyl)-5,5-dimethyl-[1,3]dioxane-4-carbonyl]-amino}-butyric acid (350 mg, 1 mmol) and 4-aminomethyl-benzoic acid ethyl ester (362 mg, 1 mmol) as a pale yellow liquid (412 mg, 45%).

LCMS (Method A): 529.3 (M+H).

Intermediate E21: (R)-2-(4-Methoxy-phenyl)-5,5-dimethyl-[1,3]dioxane-4-carboxylic acid [3-hydroxy-3-({1-[4-(2-oxo-pyrrolidin-1-yl)-benzenesulfonyl]-piperidin-4-ylmethyl}-carbamoyl)-propyl]-amide

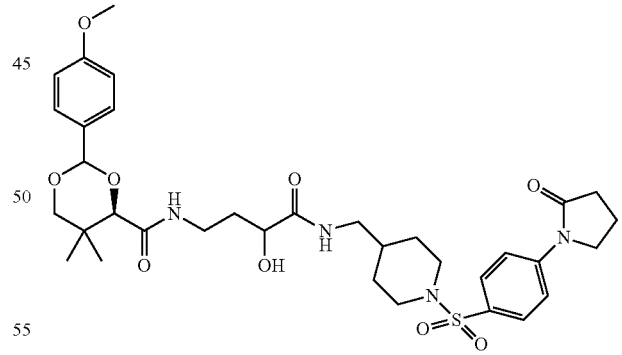

(R)-2-(4-Methoxy-phenyl)-5,5-dimethyl-[1,3]dioxane-4-carboxylic acid [3-hydroxy-3-({1-[4-(2-oxo-pyrrolidin-1-yl)-benzenesulfonyl]-piperidin-4-ylmethyl}-carbamoyl)-propyl]-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 1-[4-(4-aminomethyl-piperidine-1-sulfonyl)-phenyl]-pyrrolidin-2-one (336 mg, 1 mmol) as a pale yellow liquid (415 mg, 60%).

LCMS (Method A): 688.2 (M+H).

Intermediate E22: (R)-2-(4-Methoxy-phenyl)-5,5-dimethyl-[1,3]dioxane-4-carboxylic acid {3-hydroxy-3-(1-methanesulfonyl-piperidin-4-ylmethyl)-carbamoyl]-propyl}-amide

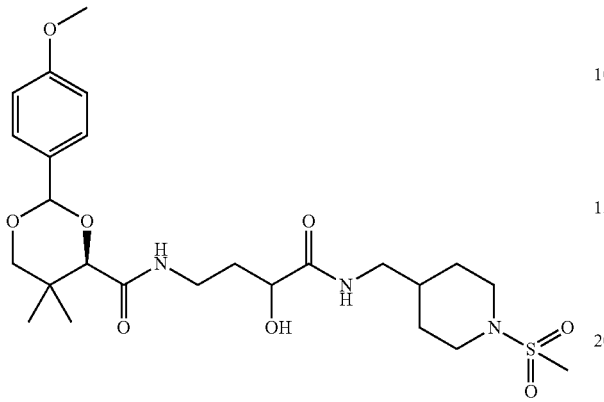

(R)-2-(4-Methoxy-phenyl)-5,5-dimethyl-[1,3]dioxane-4-carboxylic acid {3-hydroxy-3-(1-methanesulfonyl-piperidin-4-ylmethyl)-carbamoyl]-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and (1-methanesulfonyl-piperidin-4-yl)-methylamine (191 mg, 1 mmol) as a pale yellow liquid (325 mg, 60%).

LCMS (Method A): 542.3 (M+H).

Intermediate E23: (R)-2-(4-Methoxy-phenyl)-5,5-dimethyl-[1,3]dioxane-4-carboxylic acid {3-[(1-acetyl-piperidin-4-ylmethyl)-carbamoyl]-3-hydroxy-propyl}-amide

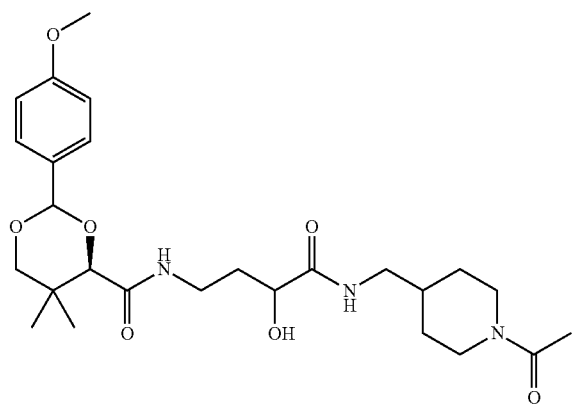

(R)-2-(4-Methoxy-phenyl)-5,5-dimethyl-[1,3]dioxane-4-carboxylic acid {3-[(1-acetyl-piperidin-4-ylmethyl)-carbamoyl]-3-hydroxy-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (365 mg, 1 mmol) and 1-(4-aminomethyl-piperidin-1-yl)-ethanone (350 mg, 1 mmol) as a pale yellow liquid (285 mg, 56%).

LCMS (Method A): 506.2 (M+H).

Intermediate E24: (R)-2-(4-Methoxy-phenyl)-5,5-dimethyl-[1,3]dioxane-4-carboxylic acid (3-hydroxy-4-morpholin-4-yl-4-oxo-butyl)-amide

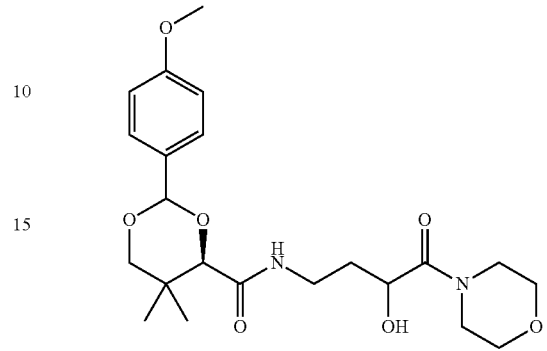

(R)-2-(4-Methoxy-phenyl)-5,5-dimethyl-[1,3]dioxane-4-carboxylic acid (3-hydroxy-4-morpholin-4-yl-4-oxo-butyl)-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and morpholine (86 mg, 1 mmol) as a pale yellow gummy liquid (230 mg, 53%).

LCMS (Method A): 438.3 (M+H).

Intermediate E25: (R)-2-(4-Methoxy-phenyl)-5,5-dimethyl-[1,3]dioxane-4-carboxylic acid {3-hydroxy-3-[4-(2-methoxy-ethoxy)-benzylcarbamoyl]-propyl}-amide

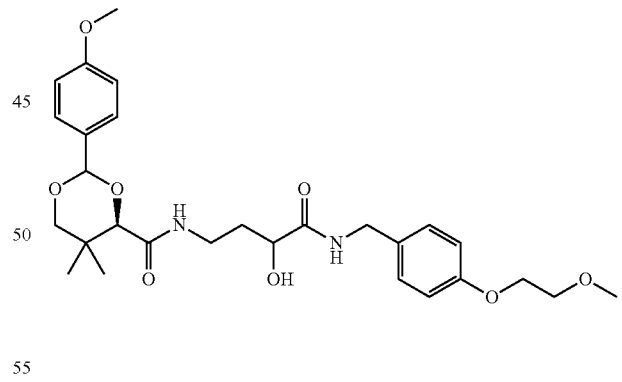

(R)-2-(4-Methoxy-phenyl)-5,5-dimethyl-[1,3]dioxane-4-carboxylic acid {3-hydroxy-3-[4-(2-methoxy-ethoxy)-benzylcarbamoyl]-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 4-(2-methoxy-ethoxy)-benzylamine (180 mg, 1 mmol) as a pale yellow liquid (375 mg, 70%).

LCMS (Method A): 531.3 (M+H).

Intermediate E26: (R)-2-(4-Methoxy-phenyl)-5,5-dimethyl-[1,3]dioxane-4-carboxylic acid (3-{[1-(4-fluoro-benzenesulfonyl)-piperidin-4-ylmethyl]-carbamoyl}-3-hydroxy-propyl)-amide

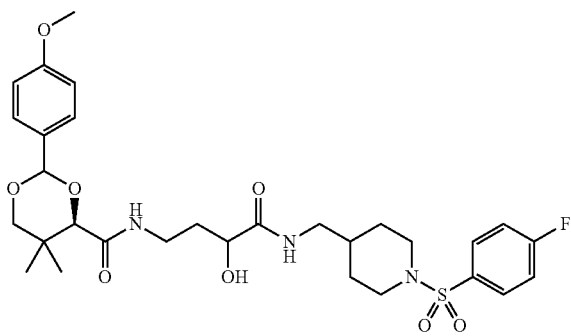

(R)-2-(4-Methoxy-phenyl)-5,5-dimethyl-[1,3]dioxane-4-carboxylic acid (3-{[1-(4-fluoro-benzenesulfonyl)-piperidin-4-ylmethyl]-carbamoyl}-3-hydroxy-propyl)-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and (1-((4-fluorophenyl)sulfonyl)piperidin-4-yl) (271 mg, 1 mmol) as a pale yellow gummy liquid (360 mg, 58%).

LCMS (Method A): 623.2 (M+H).

Intermediate E27: (R)-2-(4-Methoxy-phenyl)-5,5-dimethyl-[1,3]dioxane-4-carboxylic acid (3-{[1-(3-fluoro-benzenesulfonyl)-piperidin-4-ylmethyl]-carbamoyl}-3-hydroxy-propyl)-amide

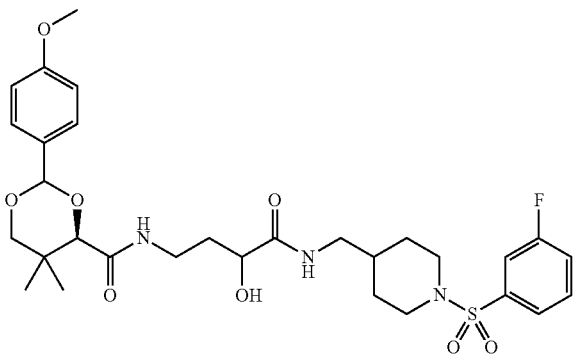

(R)-2-(4-Methoxy-phenyl)-5,5-dimethyl-[1,3]dioxane-4-carboxylic acid (3-{[1-(3-fluoro-benzenesulfonyl)-piperidin-4-ylmethyl]-carbamoyl}-3-hydroxy-propyl)-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and [1-(3-fluoro-benzenesulfonyl)-piperidin-4-yl]-methyl-amine (271 mg, 1 mmol) as a pale yellow liquid (280 mg, 45%).

LCMS (Method A): 623.0 (M+H).

Intermediate E28: (R)-2-(4-Methoxy-phenyl)-5,5-dimethyl-[1,3]dioxane-4-carboxylic acid {3-hydroxy-3-(4'-methanesulfonyl-biphenyl-4-ylmethyl)-carbamoyl]-propyl}-amide

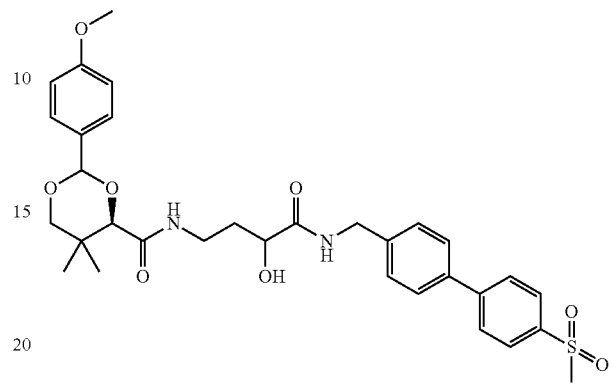

(R)-2-(4-Methoxy-phenyl)-5,5-dimethyl-[1,3]dioxane-4-carboxylic acid {3-hydroxy-3-(4'-methanesulfonyl-biphenyl-4-ylmethyl)-carbamoyl]-propyl}-amide was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and (4'-methanesulfonyl-biphenyl-4-yl)-methylamine (260 mg, 1 mmol) as a pale yellow liquid (325 mg, 53%).

LCMS (Method A): 611.2 (M+H).

Intermediate E29: 4-[(2-Hydroxy-4-{[(R)-2-(4-methoxy-phenyl)-5,5-dimethyl-[1,3]dioxane-4-carbonyl]-amino}-butyrylamino)-methyl]-benzoic acid methyl ester

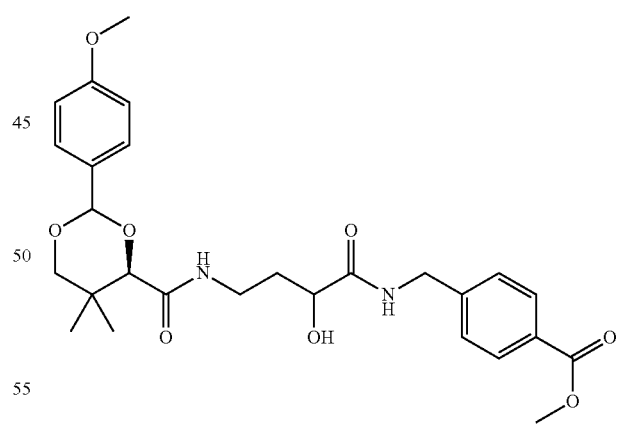

4-[(2-Hydroxy-4-{[(R)-2-(4-methoxy-phenyl)-5,5-dimethyl-[1,3]dioxane-4-carbonyl]amino}-butyrylamino)-methyl]-benzoic acid methyl ester was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 4-aminomethyl-benzoic acid methyl ester (167 mg, 1 mmol) as a pale yellow liquid (250 mg, 49%).

LCMS (Method A): 515.3 (M+H).

Intermediate E30: 4'-[(2-Hydroxy-4-{[(R)-2-(4-methoxy-phenyl)-5,5-dimethyl-[1,3]dioxane-4-carbonyl]-amino}-butyrylamino)-methyl]-biphenyl-4-carboxylic acid methyl ester

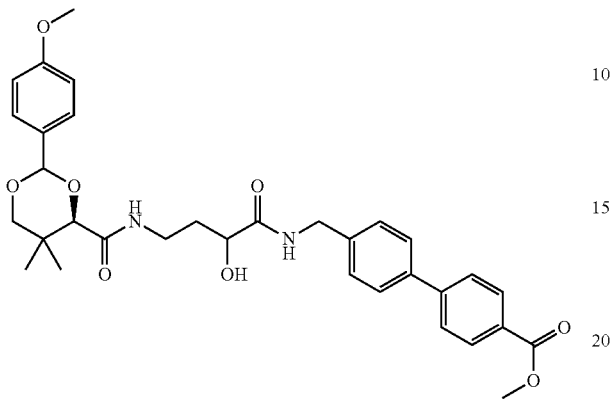

4'-[(2-Hydroxy-4-{[(R)-2-(4-methoxy-phenyl)-5,5-dimethyl-[1,3]dioxane-4-carbonyl]-amino}-butyrylamino)-methyl]-biphenyl-4-carboxylic acid methyl ester was synthesized following the general procedure E from 2-hydroxy-4-{[(R)-2-(4-methoxy-phenyl)-5,5-dimethyl-[1,3]dioxane-4-carbonyl]-amino}-butyric acid (367 mg, 1 mmol) and 4'-aminomethyl-biphenyl-4-carboxylic acid methyl ester (240 mg, 1 mmol) as a pale yellow liquid (215 mg, 36%).

LCMS (Method A): 591.2 (M+H).

Intermediate F1:
N'-(3-Phenyl-propyl)-ethane-1,2-diamine

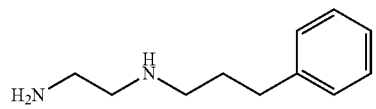

N'-(3-Phenyl-propyl)-ethane-1,2-diamine was prepared following the general procedure F from methanesulfonic acid 3-phenyl-propyl ester (1.92 g, 9 mmol) as a colorless liquid (1.15 g, 72%).

LCMS (Method A): 179.2 (M+H).

Intermediate F2: N'-Phenethyl-ethane-1,2-diamine

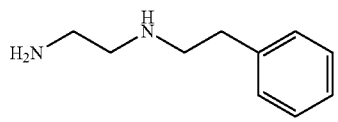 [SMILES: NCCNCCc1ccccc1]

N'-Phenethyl-ethane-1,2-diamine was prepared following the general procedure F from methanesulfonic acid phenethyl ester (2.5 g, 12.5 mmol) as a colorless liquid (1.65 g, 80%).

LCMS (Method A): 165.3 (M+H).

Intermediate F3:
4-[2-(2-Amino-ethylamino)-ethoxy]-benzonitrile

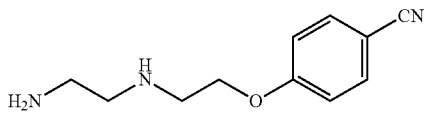 [SMILES: N#Cc1ccc(OCCNCCN)cc1]

4-[2-(2-Amino-ethylamino)-ethoxy]-benzonitrile was prepared following the general procedure F from methanesulfonic acid 2-(4-cyano-phenoxy)-ethyl ester (1.56 g, 7.5 mmol) as a colorless liquid (920 mg, 60%).

LCMS (Method A): 206.3 (M+H).

Intermediate F4: 4-{4-[(2-Amino-ethylamino)-methyl]-piperidin-1-yl}-benzonitrile

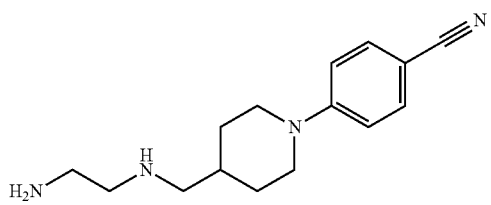 [SMILES: N#Cc1ccc(N2CCC(CNCCN)CC2)cc1]

4-{4-[(2-Amino-ethylamino)-methyl]-piperidin-1-yl}-benzonitrile was prepared following the general procedure F from methane sulfonic acid 4-(4-cyano-phenyl)-cyclohexyl methyl ester (2.02 g, 6 mmol) as a pale yellow liquid (920 mg, 60%).

LCMS (Method A): 259.3 (M+H).

Intermediate F5:
N'-(2-Phenoxy-ethyl)-ethane-1,2-diamine

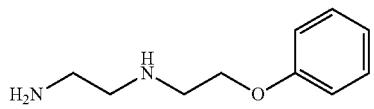

N'-(2-Phenoxy-ethyl)-ethane-1,2-diamine was prepared following the general procedure F from methanesulfonic acid 2-phenoxy-ethyl ester (1.56 g, 7.2 mmol) as a colorless liquid (820 mg, 63%).

LCMS (Method A): 181.2 (M+H).

Intermediate F6: N'-(2-(4-(Methylsulfonyl)phenoxy)ethyl)ethane-1,2-diamine

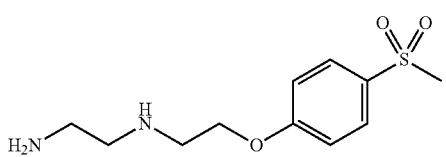 [SMILES: CS(=O)(=O)c1ccc(OCCNCCN)cc1]

N'-(2-(4-(Methylsulfonyl)phenoxy)ethyl)ethane-1,2-diamine was prepared following the general procedure F from methanesulfonic acid 2-(4-methanesulfonyl-phenoxy)-ethyl ester (1.1 g, 3.7 mmol) as a colorless liquid (750 mg, 78%).

LCMS (Method A, ELSD): 259.3 (M+H).

Intermediate F7:
4-[2-(2-Amino-ethylamino)-ethoxy]-benzoic acid methyl ester

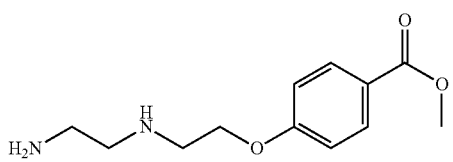 [SMILES: COC(=O)c1ccc(OCCNCCN)cc1]

4-[2-(2-Amino-ethylamino)-ethoxy]-benzoic acid methyl ester was prepared following the general procedure F from 4-(2-methanesulfonyloxy-ethoxy)-benzoic acid methyl ester (1.6 g, 5.8 mmol) as a colorless liquid (650 mg, 47%).

LCMS (Method A, ELSD): 239.3 (M+H).

Intermediate F8: N'-(2-(4-bromophenoxy)ethyl)ethane-1,2-diamine

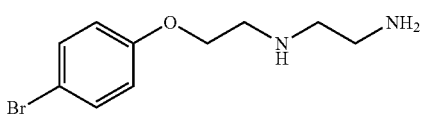 [SMILES: NCCNCCOc1ccc(Br)cc1]

N'-(2-(4-bromophenoxy)ethyl)ethane-1,2-diamine was prepared following general procedure F from 2-(4-bromophenoxy) ethanol (4.34 g, 20 mmol) as a colourless liquid to get the title compound (3.86 g, 72%).

LCMS (Method A): 261.2 (M+H).

Intermediate G1: (R)—N-(2-Amino-ethyl)-2,4-dihydroxy-3,3-dimethyl-butyramide

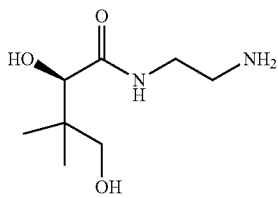

(R)—N-(2-Amino-ethyl)-2,4-dihydroxy-3,3-dimethyl-butyramide was prepared following the general procedure G from ethane-1,2-diamine (150 mg, 2 mmol) and D-pantolactone (390 mg, 3 mmol) as a pale yellow liquid (150 mg, 37%).

LCMS (Method A, ELSD): 191.0 (M+H).

Intermediate G2: (R)-2,4-Dihydroxy-3,3-dimethyl-N-[2-(3-phenyl-propylamino)-ethyl]-butyramide

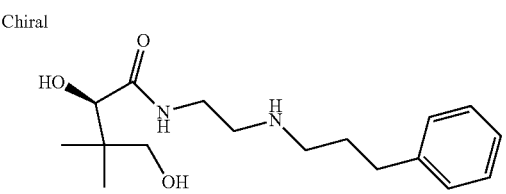 [SMILES: CC(C)(CO)[C@@H](O)C(=O)NCCNCCCc1ccccc1]

(R)-2,4-Dihydroxy-3,3-dimethyl-N-[2-(3-phenyl-propylamino)-ethyl]-butyramide was prepared following general procedure G from N'-(3-phenyl-propyl)-ethane-1,2-diamine (445 mg, 2.5 mmol) and D-pantolactone (487 mg, 3.75 mmol) as a colorless liquid (200 mg, 26%).

LCMS (Method A): 309.2 (M+H).

Intermediate G3: (R)-2,4-Dihydroxy-3,3-dimethyl-N-(2-phenethylamino-ethyl)-butyramide

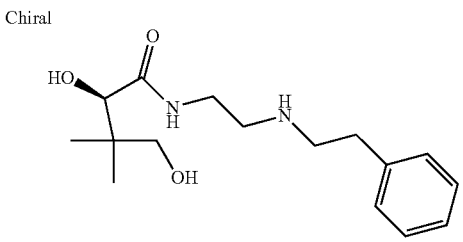 [SMILES: CC(C)(CO)[C@@H](O)C(=O)NCCNCCc1ccccc1]

(R)-2,4-Dihydroxy-3,3-dimethyl-N-(2-phenethylamino-ethyl)-butyramide was prepared following the general procedure G from N'-phenethyl-ethane-1,2-diamine (489 mg, 3 mmol) and D-pantolactone (585 mg 4.5 mmol) as a pale yellow liquid (510 mg, 58%).

LCMS (Method A): 295.2 (M+H).

Intermediate G4: (R)—N-(2-Benzylamino-ethyl)-2,4-dihydroxy-3,3-dimethyl-butyramide

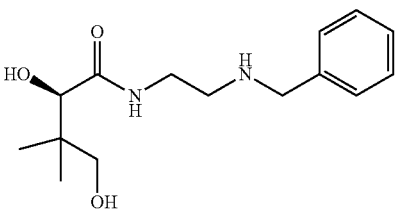 [SMILES: CC(C)(CO)[C@@H](O)C(=O)NCCNCc1ccccc1]

(R)—N-(2-Benzylamino-ethyl)-2,4-dihydroxy-3,3-dimethyl-butyramide was prepared following the general procedure G using N'-benzyl-ethane-1,3-diamine (656 mg, 4 mmol) and D-pantolactone (640 mg, 6 mmol) as a colorless liquid (305 mg, 26%).

LCMS (Method A, ELSD): 281.0 (M+H).

Intermediate G5: (R)—N-{2-[2-(4-Cyano-phenoxy)-ethylamino]-ethyl}-2,4-dihydroxy-3,3-dimethyl-butyramide

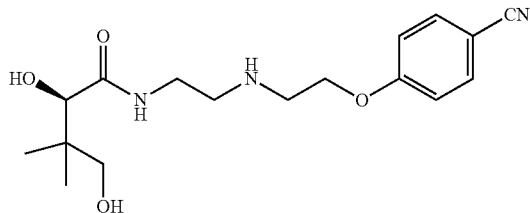 [SMILES: CC(C)(CO)[C@@H](O)C(=O)NCCNCCOc1ccc(C#N)cc1]

(R)—N-{2-[2-(4-Cyano-phenoxy)-ethylamino]-ethyl}-2,4-dihydroxy-3,3-dimethyl-butyramide was prepared following the general procedure G from 4-(2-((2-aminoethyl)amino)ethoxy)benzonitrile (717 mg, 3.5 mmol) and D-pantolactone (682 mg, 5.25 mmol) as a colorless liquid (520 mg, 44%).
LCMS (Method A): 336.3 (M+H).

Intermediate G6: (R)—N-(2-{[1-(4-Cyano-phenyl)-piperidin-4-ylmethyl]-amino}ethyl)-2,4-dihydroxy-3,3-dimethyl-butyramide

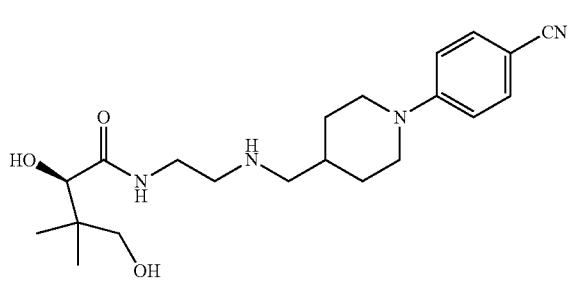 [SMILES: CC(C)(CO)[C@@H](O)C(=O)NCCNCC1CCN(c2ccc(C#N)cc2)CC1]

(R)—N-(2-{[1-(4-Cyano-phenyl)-piperidin-4-ylmethyl]-amino}-ethyl)-2,4-dihydroxy-3,3-dimethyl-butyramide was prepared following the general procedure G from 4-{4-[(2-amino-ethylamino)-methyl]-piperidin-1-yl}-benzonitrile (600 mg, 2.33 mmol) and D-pantolactone (453 mg, 3.49 mmol) as a pale yellow liquid (560 mg, 62%).
LCMS (Method A): 389.3 (M+H).

Intermediate G7: (R)-2,4-Dihydroxy-3,3-dimethyl-N-[2-(2-phenoxy-ethylamino)-ethyl]butyramide

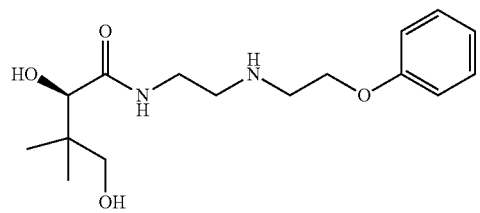 [SMILES: CC(C)(CO)[C@@H](O)C(=O)NCCNCCOc1ccccc1]

(R)-2,4-Dihydroxy-3,3-dimethyl-N-[2-(2-phenoxy-ethylamino)-ethyl]-butyramide was prepared following the general procedure G from N'-(2-phenoxyethyl)ethane-1,2-diamine (1.56 g, 8.7 mmol) and D-pantolactone (1.51 mmol, 13 mmol) as a colorless liquid (820 mg, 29%).
LCMS (Method A): 312.3 (M+H).

Intermediate G8: (R)-2,4-Dihydroxy-N-{2-[2-(4-methanesulfonyl-phenoxy)-ethylamino]-ethyl}-3,3-dimethyl-butyramide

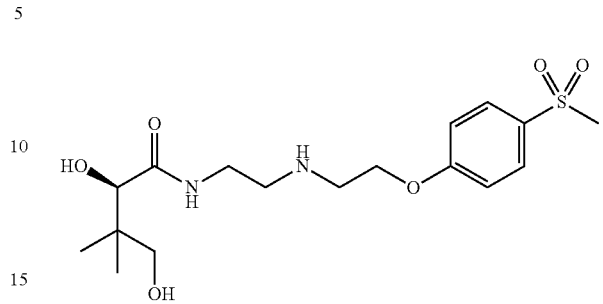

(R)-2,4-Dihydroxy-N-{2-[2-(4-methanesulfonyl-phenoxy)-ethylamino]-ethyl}-3,3-dimethyl-butyramide was prepared following the general procedure G from N'-(2-(4-(methylsulfonyl)phenoxy)ethyl)ethane-1,2-diamine (1.1 g, 4.2 mmol) and D-pantolactone (744 mg, 6.4 mmol) as a colorless liquid (750 mg, 46%).
LCMS (Method A): 389.2 (M+H).

Intermediate G9: 4-{2-[2-((R)-2,4-Dihydroxy-3,3-dimethyl-butrylamino)-ethylamino]ethoxy}-benzoic acid methyl ester

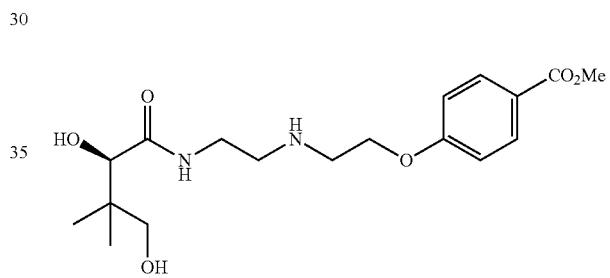

4-{2-[2-((R)-2,4-Dihydroxy-3,3-dimethyl-butyrylamino)-ethylamino]-ethoxy}-benzoic acid methyl ester was prepared following the general procedure G from 4-[2-(2-amino-ethylamino)-ethoxy]-benzoic acid methyl ester (1.6 g, 6.7 mmol) and D-pantolactone (1.16 g, 10 mmol) as a colorless liquid (650 mg, 26%).
LCMS (Method A): 369.2 (M+H).

Intermediate G10: (R)—N-(2-[2-(4-Bromo-phenoxy)-ethylamino]-ethyl)-2,4-dihydroxy-3,3-dimethyl-butyramide

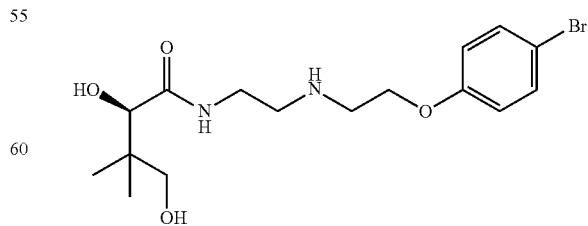

(R)—N-{2-[2-(4-Bromo-phenoxy)-ethylamino]-ethyl}-2,4-dihydroxy-3,3-dimethyl-butyramide was prepared following the general procedure G from N'-(2-(4-bromophenoxy)

ethyl)ethane-1,2-diamine (520 mg, 2 mmol) and D-pantolactone as a pale yellow oil (410 mg, 52%).

LCMS (Method A): 391.0 (M+H]).

Example 1

(R)-2,4-Dihydroxy-3,3-dimethyl-N-(3-oxo-butyl)-butyramide

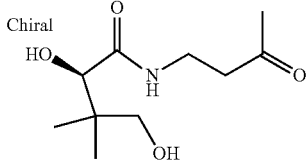

(R)-2,4-Dihydroxy-3,3-dimethyl-N-(3-oxo-butyl)-butyramide was synthesized following the general procedure B from (R)-2,2,5,5-tetramethyl-[1,3]dioxane-4-carboxylic acid (3-hydroxy-butyl)-amide (180 mg, 0.7 mmol) as a colorless gummy liquid (8 mg, 4%).

HPLC (Method A, ELSD): Rt 2.4 min (Purity 99.2%). LCMS (Method A, ELSD): 218 (M+H). ¹H NMR: (400 MHz, DMSO-d₆): δ 7.71 (t, J=4.0 Hz, 1H), 5.31 (d, J=4.0 Hz, 1H), 4.52 (t, J=4.0 Hz, 1H), 3.71 (d, J=4.0 Hz, 1H), 3.32-3.14 (m, 4H), 2.60-2.57 (m, 2H), 2.11 (s, 3H), 0.80 (s, 3H), 0.78 (s, 3H).

Example 2

(R)-2,4-Dihydroxy-3,3-dimethyl-N-(3-oxo-pentyl)-butyramide

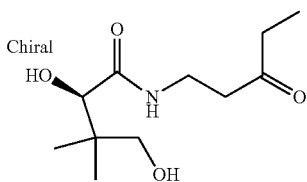 [SMILES: CCC(=O)CCNC(=O)[C@H](O)C(C)(C)CO]

(R)-2,4-Dihydroxy-3,3-dimethyl-N-(3-oxo-pentyl)-butyramide was synthesized following the general procedure B starting from (R)-2,2,5,5-tetramethyl-[1,3]dioxane-4-carboxylic acid (3-hydroxy-pentyl)-amide (118 mg, 0.43 mmol) as a pale yellow oil (65 mg, 65%).

HPLC (Method B): Rt 2.93 min (Purity 87.93%). LCMS (Method A, ELSD): 232 (M+H). ¹H NMR (400 MHz, DMSO-d₆): δ 7.71 (t, J=4.0 Hz, 1H), 5.32 (d, J=4.0 Hz, 1H), 4.52 (t, J=4.0 Hz, 1H), 3.71 (d, J=4.0 Hz, 1H), 3.32-3.14 (m, 4H), 2.60-2.57 (m, 2H), 2.49-2.41 (m, 2H), 1.98-1.94 (m, 3H), 0.80 (s, 3H), 0.78 (s, 3H).

Example 3

(R)-2,4-Dihydroxy-3,3-dimethyl-N-(3-oxo-pent-4-enyl)-butyramide

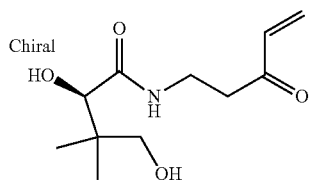 [SMILES: C=CC(=O)CCNC(=O)[C@H](O)C(C)(C)CO]

(R)-2,4-Dihydroxy-3,3-dimethyl-N-(3-oxo-pent-4-enyl)-butyramide was synthesized following the general procedure B starting from (R)-2,2,5,5-tetramethyl-[1,3]dioxane-4-carboxylic acid (3-hydroxy-pent-4-enyl)-amide (118 mg, 0.43 mmol) as a pale yellow solid (22 mg, 22%).

HPLC (Method A, ELSD): Rt 1.64 min (Purity 89.55%). LCMS (Method A, ELSD): 230 (M+H). ¹H NMR (400 MHz, DMSO-d₆): δ 7.82 (t, J=4.0 Hz, 1H), 6.36-6.21 (m, 1H), 5.94-5.91 (m, 1H), 5.30 (dd, J=4.0, 8.0 Hz, 1H), 4.41 (t, J=4.0 Hz, 1H), 3.72 (d, J=4.0 Hz, 1H), 3.36-3.24 (m, 2H), 3.17-3.13 (m, 3H), 2.81 (dd, J=4.0, 8.0 Hz, 2H), 0.80 (s, 3H), 0.78 (s, 3H).

Example 4

(R)-2,4-Dihydroxy-3,3-dimethyl-N-((E)-3-oxo-6-phenyl-hex-4-enyl)-butyramide

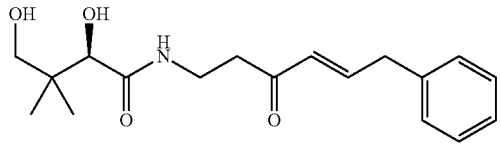 [SMILES: CC(C)(CO)[C@@H](O)C(=O)NCCC(=O)/C=C/Cc1ccccc1]

Step 1: (R)-2,2,5,5-Tetramethyl-[1,3]dioxane-4-carboxylic acid ((E)-3-hydroxy-6-phenyl-hex-4-enyl)-amide To a solution (R)-2,2,5,5-Tetramethyl-[1,3]dioxane-4-carboxylic acid (3-hydroxy-pent-4-enyl)-amide (448 mg, 1.84 mmol) in dry DCM (10 mL) was added allylbenzene (424 mg, 3.6 mmol) followed by Grubbs 2$^{nd}$ generation catalyst (75 mg, 0.088 mmol) and heated at reflux for 16 h. After completion of the reaction the solvent was removed and the crude product was purified by silica gel column chromatography (pet ether:EtOAc, 9:1) to afford a colorless gum (260 mg, 39%).

LCMS (Method A): 362.3 (M+H).

Step 2: (R)-2, 4-Dihydroxy-3, 3-dimethyl-N-((E)-3-oxo-6-phenyl-hex-4-enyl)-butyramide (R)-2,4-Dihydroxy-3,3-dimethyl-N-((E)-3-oxo-6-phenyl-hex-4-enyl)-butyramide was synthesized following the general procedure B starting from (R)-2,2,5,5-Tetramethyl-[1,3]dioxane-4-carboxylic acid (3-hydroxy-pent-4-enyl)-amide (250 mg, 0.7 mmol) as a colorless gum (6 mg, 10%).

HPLC (Method A): Rt 3.53 (Purity 91.77%). LCMS (Method A): 320.2 (M+H). $^1$H NMR (400 MHz, DMSO-d$_6$): δ 7.61 (t, J=4.0 Hz, 1H), 7.33-7.29 (m, 2H), 7.24-7.20 (m, 3H), 6.97-6.92 (m, 1H), 6.08-6.04 (m, 1H), 5.32 (d, J=8.0 Hz, 1H), 4.41 (t, J=4.0 Hz, 1H), 3.72 (d, J=8.0 Hz, 1H), 3.51 (d, J=8.0 Hz, 2H), 3.32-3.26 (m, 3H), 3.25-3.16 (m, 1H), 2.76-2.73 (m, 2H), 0.80 (s, 3H), 0.76 (s, 3H).

Example 5

(R)-2,4-Dihydroxy-3,3-dimethyl-N-((E)-5-oxo-hex-3-enyl)-butyramide

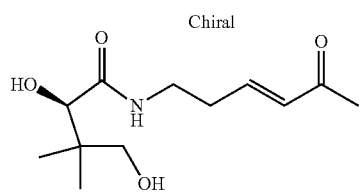 [SMILES: CC(=O)/C=C/CCNC(=O)[C@H](O)C(C)(C)CO]

Step 1: (R)-2,2,5,5-Tetramethyl-[1,3]dioxane-4-carboxylic acid ((E)-5-oxo-hex-3-enyl)-amide To a solution of (2-oxo-propyl)-phosphonic acid diethyl ester (388 mg, 2 mmol) in dry THF (10 mL) was added 60% NaH in mineral oil (80 mg, 2 mmol) at 0° C. and stirred for 15 min. A solution of (R)-2,2,5,5-tetramethyl-[1,3]dioxane-4-carboxylic acid (3-oxo-propyl)-amide (485 mg, 2 mmol) in THF (10 mL) was added dropwise and stirred for 1 h at 0° C. and another 1 h at RT. After completion of the reaction, a saturated aqueous solution of NH$_4$Cl was added and extracted with EtOAc, dried over Na$_2$SO$_4$, concentrated under reduced pressure to get crude compound which was purified by silica gel column chromatography (pet ether: EtOAc, 9:1) to afford a white solid (345 mg, 61%).

Step 2: (R)-2, 4-Dihydroxy-3, 3-dimethyl-N-((E)-5-oxo-hex-3-enyl)-butyramide (R)-2,4-Dihydroxy-3,3-dimethyl-N-((E)-5-oxo-hex-3-enyl)-butyramide was synthesized following the general procedure A starting from (R)-2,2,5,5-Tetramethyl-[1,3]dioxane-4-carboxylic acid ((E)-5-oxo-hex-3-enyl)-amide as a yellow gum (61 mg, 54%).

HPLC (Method A): Rt 1.64 min (Purity 99.16%). LCMS (Method A): 244.3 (M+H). $^1$H NMR (400 MHz, DMSO-d$_6$): δ 8.92 (t, J=4.0 Hz, 1H), 6.82-6.81 (m, 1H), 6.02 (d, J=4.0 Hz, 1H), 5.41 (d, J=8.0 Hz, 1H), 4.52 (t, J=4.0 Hz, 1H), 3.72 (d, J=8.0 Hz, 1H), 3.32-3.25 (m, 2H), 3.18-3.13 (m, 2H), 2.38-2.32 (m, 2H), 2.22 (s, 3H), 0.80 (s, 3H), 0.78 (s, 3H).

Example 6

(R)-2,4-Dihydroxy-3,3-dimethyl-N-(E)-5-oxo-7-phenyl-hept-3-enyl)-butyramide

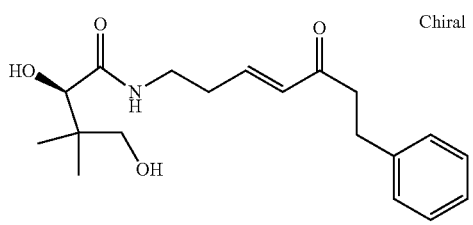 [SMILES: CC(C)(CO)[C@@H](O)C(=O)NCC/C=C/C(=O)CCc1ccccc1]

Step 1: (R)-2,2,5,5-Tetramethyl-[1,3]dioxane-4-carboxylic acid ((E)-5-oxo-7-phenyl-hept-3-enyl)-amide To a solution of diethyl (2-oxo-3-phenylpropyl) phosphonate (1.08 g, 4 mmol) in dry THF (20 mL) was added 60% NaH in mineral oil (160 mg, 4 mmol) at 0° C. and stirred for 15 min. A solution of (R)-2,2,5,5-tetramethyl-[1,3]dioxane-4-carboxylic acid (3-oxo-propyl)-amide (970 mg, 4 mmol) in THF (20 mL) was added dropwise and stirred for 1 h at 0° C. and another 1 h at RT. After completion of reaction, a saturated aqueous solution of NH$_4$Cl was added and extracted with EtOAc, dried over Na$_2$SO$_4$, and concentrated under reduced pressure to get the crude compound which was purified by silica gel column chromatography (pet ether:EtOAc, 9:1 to afford the title compound as a colorless liquid (746 mg, 52%).

LCMS (Method A): 374.2 (M+H).

Step 2: (R)-2,4-Dihydroxy-3,3-dimethyl-N-(E)-5-oxo-7-phenyl-hept-3-enyl)-butyramide (R)-2,4-Dihydroxy-3,3-dimethyl-N-(E)-5-oxo-7-phenyl-hept-3-enyl)-butyramide was synthesized following the general procedure A starting from (R)-2,2,5,5-tetramethyl-[1,3]dioxane-4-carboxylic acid ((E)-5-oxo-7-phenyl-hept-3-enyl)-amide as a colorless gum (15 mg, 87%).

HPLC (Method A): Rt 3.46 min (Purity 98.4%). LCMS (Method A): 334.2 (M+H). $^1$H NMR (400 MHz, DMSO-d$_6$): δ 7.81 (t, J=4.0 Hz, 1H), 7.27-7.15 (m, 5H), 6.83-6.79 (m, 1H), 6.11-6.07 (m, 1H), 5.42 (d, J=8.0 Hz, 1H), 4.52 (t, J=4.0 Hz, 1H), 3.71 (d, J=4.0 Hz, 1H), 3.31-3.12 (m, 4H), 2.88-2.76 (m, 4H), 2.36-2.31 (m, 2H), 0.77 (s, 3H), 0.76 (s, 3H).

Example 7

(R)—N-(3-Carbamoyl-3-oxo-propyl)-2,4-dihydroxy-3,3-dimethyl-butyramide

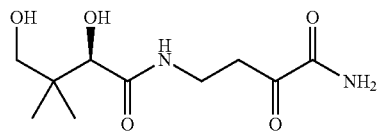 [SMILES: CC(C)(CO)[C@@H](O)C(=O)NCCC(=O)C(N)=O]

Step 1: (R)-2,2,5,5-Tetramethyl-[1,3]dioxane-4-carboxylic acid (3-carbamoyl-3-hydroxy-propyl)-amide To a solution of (R)-2,2,5,5-tetramethyl-[1,3]dioxane-4-carboxylic acid (3-oxo-propyl)-amide (500 mg, 2.05 mmol) in H$_2$O:Et$_2$O (1:1, 10 mL) was added NaHSO$_3$ (442 mg, 4.1 mmol) and cooled to 0° C. for 30 min. To this reaction mixture KCN (382 mg, 5.8 mmol) was added and stirred at RT for 2 h. After completion of the reaction, the reaction was quenched with sodium hypochlorite and extracted with Et$_2$O, dried over anhydrous Na$_2$SO$_4$ and evaporated under vacuum. The solid residue was dissolved in MeOH (10 mL) to which LiOH.H$_2$O (164 mg, 4 mmol) and H$_2$O$_2$ (0.52 mL) were added and allowed to stir at RT for 12 h. After completion of the reaction, the reaction mixture was diluted with a saturated aqueous solution of Na$_2$S$_2$O$_3$ and extracted with DCM. The organic layer was dried over Na$_2$SO$_4$, filtered and evaporated under vacuum to afford the crude product which was purified by silica gel column chromatography (pet ether:EtOAc, 7:3) to afford the title compound as a white solid (237 mg, 40%).

LCMS (Method A, ELSD): 229.2 (M+H).

Step 2: (R)—N-(3-Carbamoyl-3-oxo-propyl)-2,4-dihydroxy-3,3-dimethyl-butyramide (R)—N-(3-Carbamoyl-3-oxo-propyl)-2,4-dihydroxy-3,3-dimethyl-butyramide was synthesized following the general procedure B starting from (R)-2,2,5,5-tetramethyl-[1,3]dioxane-4-carboxylic acid (3-carbamoyl-3-hydroxy-propyl)-amide (230 mg, 1 mmol) as a colorless gum (120 mg, 45%).

HPLC (Method B): Rt 5.25 (Purity 98.05%). LCMS (Method A, ELSD): 247.2 (M+H). $^1$H NMR (400 MHz, DMSO-$d_6$): δ 7.93 (s, 1H), 7.72 (t, J=4.0 Hz, 1H), 7.63 (s, 1H), 5.31 (d, J=8.0 Hz, 1H), 4.43 (t, J=4.0 Hz, 1H), 3.72 (d, J=4.0 Hz, 1H), 3.37-3.25 (m, 3H), 3.11 (dd, J=4.0, 8.0 Hz, 1H), 2.95-2.91 (m, 2H), 0.78 (s, 3H), 0.77 (s, 3H).

Example 8

(R)—N-(3-Cyclopropylcarbamoyl-3-oxo-propyl)-2,4-dihydroxy-3,3-dimethyl-butyramide

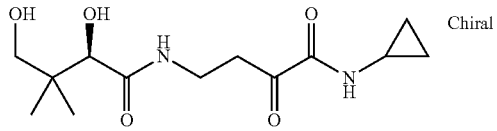 [SMILES: CC(C)(CO)[C@@H](O)C(=O)NCCC(=O)C(=O)NC1CC1]

(R)—N-(3-Cyclopropylcarbamoyl-3-oxo-propyl)-2,4-dihydroxy-3,3-dimethyl-butyramide was synthesized following the general procedure B starting from (R)-2,2,5,5-tetramethyl-[1,3]dioxane-4-carboxylic acid (3-cyclopropyl carbamoyl-3-hydroxy-propyl)-amide as a colorless gum (23 mg, 31%).

HPLC (Method A, ELSD): Rt 1.72 min (Purity 94.2%). LCMS (Method A, ELSD): 287.2 (M+H). $^1$H NMR (400 MHz, DMSO-$d_6$): δ 8.81 (t, J=4.0 Hz, 1H), 7.72 (t, J=4.0 Hz, 1H), 5.33 (d, J=8.0 Hz, 1H), 4.41 (t, J=4.0 Hz, 1H), 3.72 (d, J=4.0 Hz, 1H), 3.31-3.12 (m, 4H), 2.97-2.95 (m, 2H), 2.72-2.70 (m, 1H), 0.80 (s, 3H), 0.78 (s, 3H), 0.64-0.56 (m, 4H).

Example 9

(R)—N-(3-Benzylcarbamoyl-3-oxo-propyl)-2,4-dihydroxy-3,3-dimethyl-butyramide

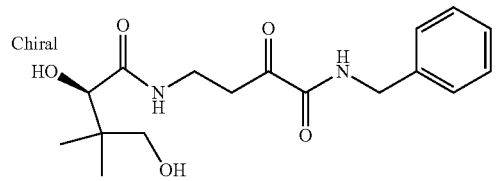 [SMILES: CC(C)(CO)[C@@H](O)C(=O)NCCC(=O)C(=O)NCc1ccccc1]

(R)—N-(3-Benzylcarbamoyl-3-oxo-propyl)-2,4-dihydroxy-3,3-dimethyl-butyramide was synthesized following the general procedure B starting from (R)-2,2,5,5-tetramethyl-[1,3]dioxane-4-carboxylic acid (3-benzylcarbamoyl-3-hydroxy-propyl)-amide (137 mg, 0.36 mmol) as a white solid (83 mg, 68%).

HPLC (Method A, ELSD): Rt 2.85 min (Purity 97.9%). LCMS (Method A, ELSD): 337.2 (M+H). $^1$H NMR (400 MHz, DMSO-$d_6$): δ 9.10 (t, J=4.0 Hz, 1H), 7.76 (s, 1H), 7.31-7.22 (m, 5H), 5.33 (d, J=8.0 Hz, 1H), 4.43 (t, J=4.0 Hz, 1H), 4.30-3.68 (m, 2H), 3.67-3.36 (m, 1H), 3.37-3.29 (m, 1H), 3.28-3.25 (m, 2H), 3.17-3.13 (m, 1H), 3.01-2.97 (m, 2H), 0.80 (s, 3H), 0.75 (s, 3H).

Example 10

(R)—N-[3-(2-Fluoro-benzylcarbamoyl)-3-oxo-propyl]-2,4-dihydroxy-3,3-dimethyl-butyramide

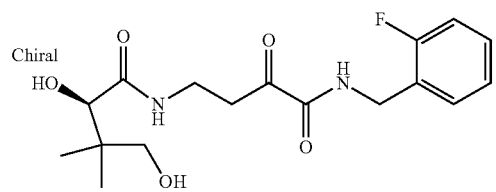 [SMILES: CC(C)(CO)[C@@H](O)C(=O)NCCC(=O)C(=O)NCc1ccccc1F]

(R)—N-[3-(2-Fluoro-benzylcarbamoyl)-3-oxo-propyl]-2,4-dihydroxy-3,3-dimethyl-butyramide was synthesized following the general procedure B starting from (R)-2,2,5,5-tetramethyl-[1,3]dioxane-4-carboxylic acid [3-(2-fluoro-benzylcarbamoyl)-3-hydroxy-propyl]-amide (90 mg, 0.23 mmol) as a white solid (32 mg, 40%).

HPLC (Method A, ELSD): Rt 2.8 min (Purity 98.8%). LCMS (Method A, ELSD): 355.2 (M+H). $^1$H NMR (400 MHz, DMSO-$d_6$): δ 9.10 (t, J=4.0 Hz, 1H), 7.77 (s, 1H), 7.32-7.28 (m, 2H), 7.18-7.12 (m, 2H), 5.34 (d, J=5.5 Hz, 1H), 4.74 (t, J=5.5 Hz, 1H), 4.35 (d, J=6.3 Hz, 2H), 3.68 (d, J=5.6 Hz, 1H), 3.38-3.28 (m, 1H), 3.27-3.25 (m, 2H), 3.17-3.13 (m, 1H), 3.00-2.96 (m, 2H), 0.78 (s, 3H), 0.76 (s, 3H).

Example 11

(R)—N-[3-(Cyclohexylmethyl-carbamoyl)-3-oxo-propyl]-2,4-dihydroxy-3,3-dimethyl-butyramide

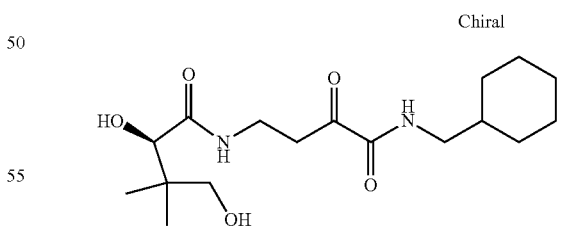

(R)—N-[3-(Cyclohexylmethyl-carbamoyl)-3-oxo-propyl]-2,4-dihydroxy-3,3-dimethyl-butyramide was synthesized following the general procedure B starting from (R)-2,2,5,5-tetramethyl-[1,3]dioxane-4-carboxylic acid [3-(cyclohexylmethyl-carbamoyl)-3-hydroxy-propyl]-amide (136 mg, 0.35 mmol) as a white solid (96 mg, 79%).

HPLC (Method A): Rt 3.3 min (Purity 99.4%). LCMS (Method A, ELSD): 343.3 (M+H). $^1$H NMR (400 MHz, DMSO-$d_6$): δ 8.51 (d, J=6.2 Hz, 1H), 7.73 (t, J=5.8 Hz, 1H), 5.33 (d, J=5.6 Hz, 1H), 4.43 (t, J=5.6 Hz, 1H), 3.67 (d, J=5.5 Hz, 1H), 3.33-3.27 (m, 1H), 3.26-3.14 (m, 2H), 3.13-2.96 (m, 1H), 2.96-2.92 (m, 4H), 1.61 (d, J=13.4 Hz, 5H), 1.46 (s, 1H), 1.16-1.10 (m, 3H), 0.84 (d, J=9.8 Hz, 2H), 0.78 (s, 3H), 0.76 (s, 3H).

Example 12

(R)-2,4-Dihydroxy-3,3-dimethyl-N-(3-oxo-3-phenethylcarbamoyl-propyl)-butyramide

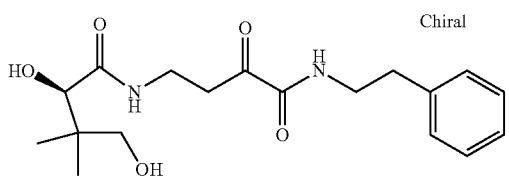 [SMILES: CC(C)(CO)[C@@H](O)C(=O)NCCC(=O)C(=O)NCCc1ccccc1]

(R)-2,4-Dihydroxy-3,3-dimethyl-N-(3-oxo-3-phenethylcarbamoyl-propyl)-butyramide was synthesized following the general procedure B starting from (R)-2,2,5,5-tetramethyl-[1, 3]dioxane-4-carboxylic acid (3-hydroxy-3-phenethylcarbamoyl-propyl)-amide (102 mg, 0.26 mmol) as a white solid (60 mg, 66%).

HPLC (Method A, ELSD): Rt 3.08 min (Purity 98.2%). LCMS (Method A, ELSD): 351.3 (M+H). $^1$H NMR (400 MHz, DMSO-$d_6$): δ 8.60 (t, J=4.2 Hz, 1H), 7.73 (t, J=4.2 Hz, 1H), 7.30-7.26 (m, 2H), 7.20-7.17 (m, 3H), 5.33 (d, J=5.6 Hz, 1H), 4.44 (t, J=5.6 Hz, 1H), 3.67 (d, J=5.5 Hz, 1H), 3.36-3.30 (m, 2H), 3.29-3.17 (m, 3H), 3.16-3.13 (m, 1H), 2.97-2.93 (m, 2H), 2.76 (t, J=7.1 Hz, 2H), 0.78 (s, 3H), 0.76 (s, 3H).

Example 13

(S)—N-(3-Benzylcarbamoyl-3-oxo-propyl)-2,4-dihydroxy-3,3-dimethyl-butyramide

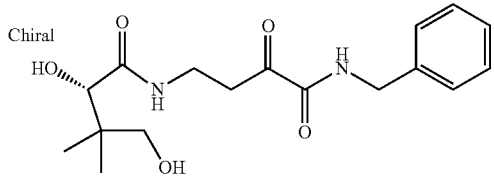 [SMILES: CC(C)(CO)[C@H](O)C(=O)NCCC(=O)C(=O)NCc1ccccc1]

(S)—N-(3-Benzylcarbamoyl-3-oxo-propyl)-2,4-dihydroxy-3,3-dimethyl-butyramide was synthesized following the general procedure B starting from (S)-2,2,5,5-tetramethyl-[1,3]dioxane-4-carboxylic acid (3-benzylcarbamoyl-3-hydroxy-propyl)-amide (73 mg, 0.19 mmol) as a white solid (31 mg, 48%).

HPLC (Method A, ELSD): Rt 2.8 min (Purity 94.4%). LCMS (Method A, ELSD): 337.2 (M+H). $^1$H NMR (400 MHz, DMSO-$d_6$): δ 9.10 (t, J=4.2 Hz, 1H), 7.76 (s, 1H), 7.31-7.22 (m, 5H), 5.33 (d, J=5.6 Hz, 1H), 4.44 (t, J=5.6 Hz, 1H), 4.30 (d, J=6.4 Hz, 2H), 3.68 (d, J=5.6 Hz, 1H), 3.36-3.27 (m, 1H), 3.26-3.16 (m, 2H), 3.15-3.13 (m, 2H), 3.01-2.97 (m, 2H), 0.78 (s, 3H), 0.76 (s, 3H).

Example 14

(R)-2,4-Dihydroxy-3,3-dimethyl-N-[3-oxo-3-(2-thiophen-2-yl-ethylcarbamoyl)-propyl]-butyramide

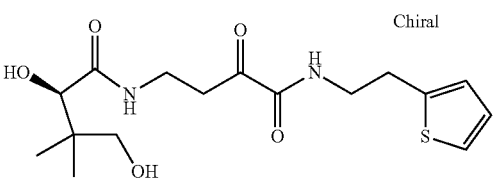 [SMILES: CC(C)(CO)[C@@H](O)C(=O)NCCC(=O)C(=O)NCCc1cccs1]

(R)-2,4-Dihydroxy-3,3-dimethyl-N-[3-oxo-3-(2-thiophen-2-yl-ethylcarbamoyl)-propyl]-butyramide was synthesized following the general procedure B starting from (R)-2,2,5,5-tetramethyl-[1,3]dioxane-4-carboxylic acid [3-hydroxy-3-(2-thiophen-2-yl-ethylcarbamoyl)-propyl]-amide (69 mg, 0.17 mmol) as an off-white solid (19 mg, 31%).

HPLC (Method A, ELSD): Rt 2.9 min (Purity 99.1%). LCMS (Method A, ELSD): 357.3, (M+H). $^1$H NMR (400 MHz, DMSO-$d_6$): δ 8.81 (t, J=4.0 Hz, 1H), 7.72 (t, J=4.0 Hz, 1H), 7.31 (dd, J=4.0, 8.0 Hz, 1H), 6.94-6.86 (m, 2H), 5.31 (dd, J=6.0, 4.0 Hz, 1H), 4.4 (t, J=4.0 Hz, 1H), 3.71 (dd, J=8.0, 4.2 Hz, 1H), 3.37-3.25 (m, 5H), 3.22 (dd, J=8.0, 4.2 Hz, 1H), 2.99-2.94 (m, 4H), 0.78 (s, 3H), 0.76 (s, 3H).

Example 15

(R)-2,4-Dihydroxy-3,3-dimethyl-N-[3-oxo-3-(3-trifluoromethoxy-benzylcarbamoyl)-propyl]-butyramide

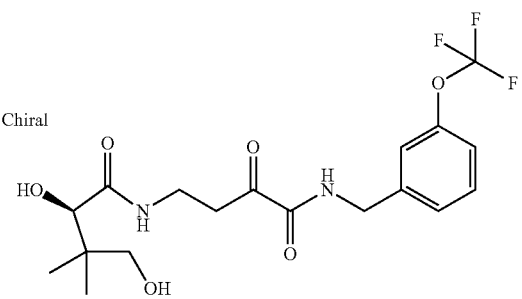 [SMILES: CC(C)(CO)[C@@H](O)C(=O)NCCC(=O)C(=O)NCc1cccc(OC(F)(F)F)c1]

(R)-2,4-Dihydroxy-3,3-dimethyl-N-[3-oxo-3-(3-trifluoromethoxy-benzylcarbamoyl)-propyl]-butyramide was synthesized following the general procedure B starting from (R)-2,2,5,5-tetramethyl-[1,3]dioxane-4-carboxylic acid [3-hydroxy-3-(3-trifluoro methoxy-benzylcarbamoyl)-propyl]-amide (166 mg, 0.36 mmol) as a off-white solid (130 mg, 86%).

HPLC (Method B): Rt 5.04 min (Purity 99.6%). LCMS (Method A, ELSD): 421.3 (M+H). $^1$H NMR (400 MHz, DMSO-$d_6$): δ 9.11 (d, J=8.0 Hz, 1H), 7.81 (t, J=4.0 Hz, 1H), 7.42 (t, J=4.0 Hz, 1H), 7.31-7.21 (m, 3H), 5.31 (d, J=8.0 Hz, 1H), 4.42 (t, J=4.0 Hz, 1H), 4.31 (d, J=4.0 Hz, 2H), 3.71 (d, J=8.0 Hz, 1H), 3.39-3.25 (m, 3H), 3.23 (t, J=4.0 Hz, 1H), 3.00-2.96 (m, 2H), 0.78 (s, 3H), 0.76 (s, 3H).

Example 16

(R)-2,4-Dihydroxy-3,3-dimethyl-N-(3-oxo-3-phenyl-carbamoyl-propyl)-butyramide

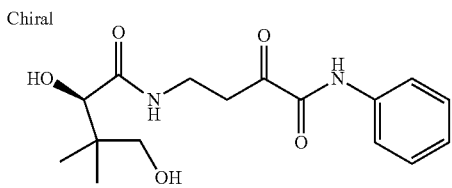 [SMILES: CC(C)(CO)[C@@H](O)C(=O)NCCC(=O)C(=O)Nc1ccccc1]

(R)-2,4-Dihydroxy-3,3-dimethyl-N-(3-oxo-3-phenylcarbamoyl-propyl)-butyramide was synthesized following the general procedure B starting from (R)-2,2,5,5-tetramethyl-[1,3]dioxane-4-carboxylic acid (3-hydroxy-3-phenyl carbamoyl-propyl)-amide (31 mg, 0.09 mmol) as a white solid (3 mg, 11%).

HPLC (Method A, ELSD): Rt 2.85 min (Purity 99.4%). LCMS (Method A, ELSD): 323.3 (M+H). $^1$H NMR (400 MHz, DMSO-$d_6$): δ 10.41 (s, 1H), 7.83-7.80 (m, 3H), 7.35-7.31 (m, 2H), 7.13 (t, J=4.0 Hz, 1H), 5.31 (d, J=4.0 Hz, 1H), 4.51 (t, J=4.0 Hz, 1H), 3.7 (d, J=8.0 Hz, 1H), 3.41-3.26 (m, 3H), 3.17-3.03 (m, 3H), 0.78 (s, 3H), 0.76 (s, 3H).

Example 17

(R)—N-[3-(4-Fluoro-benzylcarbamoyl)-3-oxo-propyl]-2,4-dihydroxy-3,3-dimethyl-butyramide

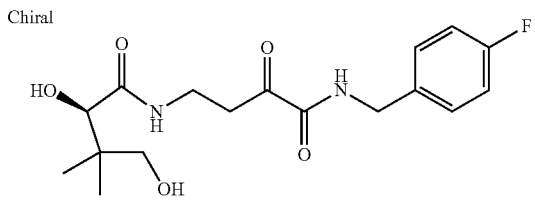 [SMILES: CC(C)(CO)[C@@H](O)C(=O)NCCC(=O)C(=O)NCc1ccc(F)cc1]

(R)—N-[3-(4-Fluoro-benzylcarbamoyl)-3-oxo-propyl]-2,4-dihydroxy-3,3-dimethyl-butyramide was synthesized following the general procedure B starting from (R)-2,2,5,5-tetramethyl-[1, 3]dioxane-4-carboxylic acid [3-(4-fluoro-benzylcarbamoyl)-3-hydroxy-propyl]-amide (154 mg, 0.39 mmol) as an off-white solid (91 mg, 66%).

HPLC (Method A, ELSD): Rt 2.97 min (Purity 95.6%). LCMS (Method A, ELSD): 355.3 (M+H). $^1$H NMR (400 MHz, DMSO-$d_6$): δ 9.11 (t, J=4.0 Hz, 1H), 7.81 (t, J=4.0 Hz, 1H), 7.32-7.28 (m, 2H), 7.13-7.09 (m, 2H), 5.33 (d, J=8.0 Hz, 1H), 4.43 (t, J=4.0 Hz, 1H), 4.31 (d, J=4.0 Hz, 2H), 3.73 (d, J=4.0 Hz, 1H), 3.67-3.25 (m, 3H), 3.13 (dd, J=4.0, 8.0 Hz, 1H), 2.99-2.95 (m, 2H), 0.78 (s, 3H), 0.76 (s, 3H).

Example 18

(R)—N-(3-Cyclohexylcarbamoyl-3-oxo-propyl)-2,4-dihydroxy-3,3-dimethyl butyramide

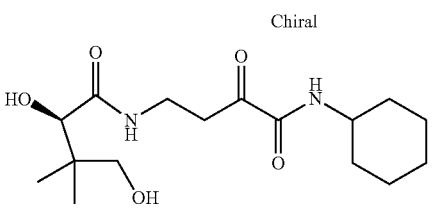 [SMILES: CC(C)(CO)[C@@H](O)C(=O)NCCC(=O)C(=O)NC1CCCCC1]

(R)—N-(3-Cyclohexylcarbamoyl-3-oxo-propyl)-2,4-dihydroxy-3,3-dimethyl butyramide was synthesized following the general procedure B starting from (R)-2,2,5,5-tetramethyl-[1,3]dioxane-4-carboxylic acid (3-cyclohexylcarbamoyl-3-hydroxy-propyl)-amide (61 mg, 0.17 mmol) as a white solid (17 mg, 31%).

HPLC (Method A, ELSD): Rt 2.98 min (Purity 99.1%). LCMS (Method A, ELSD): 329.3 (M+H). $^1$H NMR (400 MHz, DMSO-$d_6$): δ 8.33 (t, J=4.0 Hz, 1H), 7.73 (d, J=4.0 Hz, 1H), 5.32 (d, J=4.0 Hz, 1H), 4.43 (t, J=4.0 Hz, 1H), 3.71 (d, J=4.0 Hz, 1H), 3.54-3.51 (m, 1H), 3.34-3.24 (m, 3H), 3.1 (dd, J=4.0, 8.0 Hz, 1H), 2.97-2.93 (m, 2H), 1.68-1.54 (m, 5H), 1.30-1.22 (m, 4H), 1.07-1.05 (m, 1H), 0.78 (s, 3H), 0.76 (s, 3H).

Example 19

(R)-2,4-Dihydroxy-3,3-dimethyl-N-{3-[(naphthalen-1-ylmethyl)-carbamoyl]-3-oxo-propyl}-butyramide

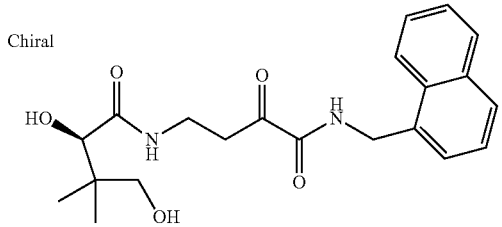 [SMILES: CC(C)(CO)[C@@H](O)C(=O)NCCC(=O)C(=O)NCc1cccc2ccccc12]

(R)-2,4-Dihydroxy-3,3-dimethyl-N-{3-[(naphthalen-1-ylmethyl)-carbamoyl]-3-oxo-propyl}-butyramide was synthesized following the general procedure B starting from (R)-2,2,5,5-tetramethyl-[1,3]dioxane-4-carboxylic acid {3-hydroxy-3-[(naphthalen-1-ylmethyl)-carbamoyl]-propyl}-amide (131 mg, 0.36 mmol) as a white gum (96 mg, 81%).

HPLC (Method A): Rt 3.52 min (Purity 91%). LCMS (Method A): 387.2 (M+H). $^1$H NMR (400 MHz, DMSO-$d_6$): δ 9.21 (t, J=4.0 Hz, 1H), 8.12 (d, J=8.0 Hz, 1H), 7.91 (t, J=4.0 Hz, 1H), 7.82-7.77 (m, 2H), 7.56-7.52 (m, 2H), 7.42 (t, J=4.0 Hz, 2H), 5.31 (d, J=8.0 Hz, 1H), 4.82 (d, J=4.0 Hz, 2H), 4.42 (t, J=4.0 Hz, 1H), 3.71 (d, J=4.0 Hz, 2H), 3.31-3.25 (m, 2H), 3.21 (t, J=4.0 Hz, 1H), 3.02-3.00 (m, 2H), 0.78 (s, 3H), 0.76 (s, 3H).

Example 20

(R)-2,4-Dihydroxy-3,3-dimethyl-N-(3-oxo-3-phenethylcarbamoyl-propyl)-butyramide

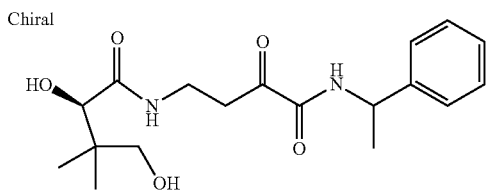 [SMILES: CC(NC(=O)C(=O)CCNC(=O)[C@H](O)C(C)(C)CO)c1ccccc1]

(R)-2,4-Dihydroxy-3,3-dimethyl-N-(3-oxo-3-phenethylcarbamoyl-propyl)-butyramide was synthesized following the general procedure B starting from (R)-2,2,5,5-tetramethyl-[1,3]dioxane-4-carboxylic acid [3-hydroxy-3-(1-phenyl-ethylcarbamoyl)-propyl]-amide (133 mg, 0.34 mmol) as a white solid (19 mg, 16%).

HPLC (Method A): Rt 3.02 min (Purity 94.7%). LCMS (Method A, ELSD): 351.2 (M+H). $^1$H NMR (400 MHz, DMSO-$d_6$): δ 9.02 (d, J=8.0 Hz, 1H), 7.72 (d, J=8.0 Hz, 1H), 7.35-7.20 (m, 5H), 5.32 (dd, J=4.0, 8.0 Hz, 1H), 4.95-4.91 (m, 1H), 4.42 (t, J=4.0 Hz, 1H), 3.72 (d, J=4.0 Hz, 1H), 3.35-3.24 (m, 3H), 3.12 (dd, J=4.0, 8.0 Hz, 3H), 1.42 (d, J=8.0 Hz, 3H), 0.78 (s, 3H), 0.76 (s, 3H).

Example 21

(R)—N-[3-(Benzhythyl-carbamoyl)-3-oxo-propyl]-2,4-dihydroxy-3,3-dimethyl-butyramide

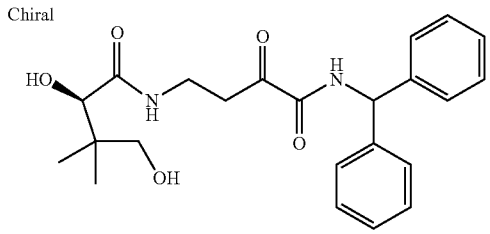 [SMILES: CC(C)(CO)[C@@H](O)C(=O)NCCC(=O)C(=O)NC(c1ccccc1)c1ccccc1]

(R)—N-[3-(Benzhydryl-carbamoyl)-3-oxo-propyl]-2,4-dihydroxy-3,3-dimethyl-butyramide was synthesized following the general procedure B starting from (R)-2,2,5,5-tetramethyl-[1,3]dioxane-4-carboxylic acid [3-(benzhydryl-carbamoyl)-3-hydroxy-propyl]-amide (87 mg, 0.20 mmol) as a pale yellow gum (25 mg, 31%).

HPLC (Method A, ELSD): Rt 3.59 min (Purity 98.5%). LCMS (Method A): 413.3 (M+H). $^1$H NMR (400 MHz, DMSO-$d_6$): δ 9.32 (t, J=4.0 Hz, 1H), 7.82 (t, J=4.0 Hz, 1H), 7.34-7.24 (m, 10H), 6.22 (d, J=8.0 Hz, 1H), 5.32 (d, J=4.0 Hz, 1H), 4.42 (t, J=4.0 Hz, 1H), 3.71 (d, J=8.0 Hz, 1H), 3.33-3.25 (m, 3H), 3.21 (t, J=4.0 Hz, 1H), 3.00-2.97 (m, 2H), 0.78 (s, 3H), 0.76 (s, 3H)

Example 22

(R)-2,4-Dihydroxy-N-[3-(3-methoxy-benzylcarbamoyl)-3-oxo-propyl]-3,3-dimethyl-butyramide

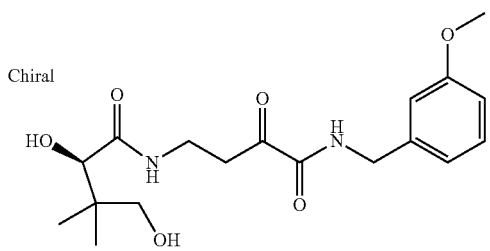 [SMILES: COc1cccc(CNC(=O)C(=O)CCNC(=O)[C@H](O)C(C)(C)CO)c1]

(R)-2,4-Dihydroxy-N-[3-(3-methoxy-benzylcarbamoyl)-3-oxo-propyl]-3,3-dimethyl-butyramide was synthesized following the general procedure B starting from (R)-2,2,5,5-tetramethyl-[1,3]dioxane-4-carboxylic acid [3-hydroxy-3-(3-methoxy-benzylcarbamoyl)-propyl]-amide (17 mg, 0.04 mmol) as a pale yellow gum (12 mg, 79%).

HPLC (Method B): Rt 4.01 min (Purity 99.3%). LCMS (Method A, ELSD): 367.3 (M+H). $^1$H NMR (400 MHz, DMSO-$d_6$): δ 9.13 (t, J=4.0 Hz, 1H), 7.83 (t, J=4.0 Hz, 1H), 7.22 (t, J=4.0 Hz, 1H), 6.83-6.77 (m, 3H), 5.32 (d, J=4.0 Hz, 1H), 4.42 (t, J=4.0 Hz, 1H), 4.33 (d, J=4.0 Hz, 2H), 3.71-3.66 (m, 4H), 3.32-3.25 (m, 3H), 3.23 (t, J=4.0 Hz, 1H), 3.00-2.96 (m, 2H), 0.78 (s, 3H), 0.76 (s, 3H).

Example 23

(R)-2,4-Dihydroxy-3,3-dimethyl-N-[3-oxo-3-(2-trifluoromethyl-benzylcarbamoyl)-propyl]-butyramide

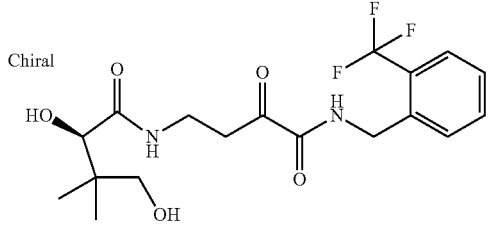 [SMILES: CC(C)(CO)[C@@H](O)C(=O)NCCC(=O)C(=O)NCc1ccccc1C(F)(F)F]

(R)-2,4-Dihydroxy-3,3-dimethyl-N-[3-oxo-3-(2-trifluoromethyl-benzylcarbamoyl)-propyl]-butyramide was synthesized following the general procedure B starting from (R)-2,2,5,5-tetramethyl-[1,3]dioxane-4-carboxylic acid [3-hydroxy-3-(2-trifluoromethyl-benzylcarbamoyl)-propyl]-amide (200 mg, 0.5 mmol) as a colorless gum (138 mg, 76%).

HPLC (Method A, ELSD): Rt 3.59 min (Purity 98%). LCMS (Method A, ELSD): 405.2 (M+H). $^1$H NMR (400 MHz, DMSO-$d_6$): δ 9.24 (d, J=8.0 Hz, 1H), 7.83 (t, J=4.0 Hz, 1H), 7.73 (d, J=8.0 Hz, 1H), 7.63 (d, J=8.0 Hz, 1H), 7.59-7.44 (m, 2H), 5.42 (d, J=4.0 Hz, 1H), 4.50-4.43 (m, 3H), 3.74 (d, J=4.0 Hz, 1H), 3.32-3.26 (m, 2H), 3.17-3.13 (m, 2H), 3.00-2.96 (m, 2H), 0.78 (s, 3H), 0.76 (s, 3H).

Example 24

(R)-2,4-Dihydroxy-N-[3-(4-methanesulfonyl-benzyl-carbamoyl)-3-oxo-propyl]-3,3-dimethyl-butyramide

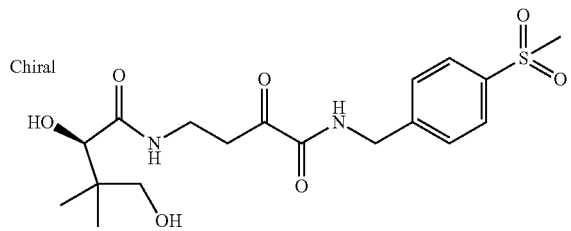 [SMILES: CC(C)(CO)[C@@H](O)C(=O)NCCC(=O)C(=O)NCc1ccc(S(C)(=O)=O)cc1]

(R)-2,4-Dihydroxy-N-[3-(4-methanesulfonyl-benzylcarbamoyl)-3-oxo-propyl]-3,3-dimethyl-butyramide was synthesized following the general procedure B starting from (R)-2,2,5,5-tetramethyl-[1,3]dioxane-4-carboxylic acid [3-hydroxy-3-(4-methane sulfonyl-benzyl carbamoyl)-propyl]-amide (32 mg, 0.07 mmol) as a pale yellow gum (4 mg, 14%).

HPLC (Method B): Rt 3.33 min (Purity 90.12%). LCMS (Method B): 415.0 (M+H). $^1$H NMR (400 MHz, DMSO-$d_6$): δ 9.24 (t, J=4.0 Hz, 1H), 7.86-7.78 (m, 3H), 7.53 (d, J=8.0 Hz, 2H), 5.34 (d, J=8.0 Hz, 1H), 4.45-4.39 (m, 3H), 3.72 (d, J=4.0 Hz, 1H), 3.31-3.27 (m, 3H), 3.17-3.15 (m, 4H), 2.99-2.96 (m, 2H), 0.80 (s, 3H), 0.78 (s, 3H).

Example 25

[4-((R)-2,4-Dihydroxy-3,3-dimethyl-butyrylamino)-2-oxo-butyrylamino]-acetic acid methyl ester

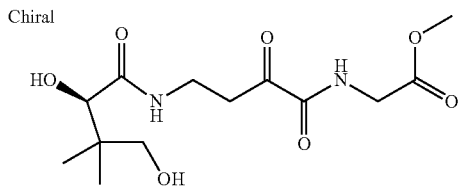 [SMILES: COC(=O)CNC(=O)C(=O)CCNC(=O)[C@H](O)C(C)(C)CO]

[4-((R)-2,4-Dihydroxy-3,3-dimethyl-butyrylamino)-2-oxo-butyrylamino]-acetic acid methyl ester was synthesized following the general procedure B starting from {2-hydroxy-4-R(R)-2,2,5,5-tetramethyl-[1,3]dioxane-4-carbonyl)-amino] butyryl amino}-acetic acid methyl ester (93 mg, 0.26 mmol) as a colorless gum (33 mg, 40%).

HPLC (Method B): Rt 2.56 min (Purity 95%). LCMS (Method B): 319.0 (M+H). $^1$H NMR (400 MHz, DMSO-$d_6$): δ 8.93 (t, J=4.0 Hz, 1H), 7.84 (t, J=4.0 Hz, 1H), 5.33 (d, J=4.0 Hz, 1H), 4.54 (t, J=4.0 Hz, 1H), 3.92 (d, J=4.0 Hz, 2H), 3.68-3.61 (m, 4H), 3.39-3.24 (m, 3H), 3.17-3.12 (m, 1H), 2.90-2.50 (m, 2H), 0.78 (s, 3H), 0.76 (s, 3H).

Example 26

(R)-2,4-Dihydroxy-N-{3-[3-(2-methanesulfonylamino-ethoxy)-benzylcarbamoyl]-3-oxo-propyl}-3,3-dimethyl-butyramide

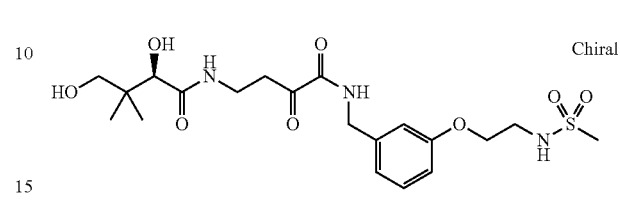

(R)-2,4-Dihydroxy-N-{3-[3-(2-methanesulfonylamino-ethoxy)-benzylcarbamoyl]-3-oxo-propyl}-3,3-dimethyl-butyramide was synthesized following the general procedure B starting from (R)-2-(4-methoxy-phenyl)-5,5-dimethyl-[1,3]dioxane-4-carboxylic acid {3-hydroxy-3-3-2-methanesulfonylamino-ethoxy)-benzylcarbamoyl]-propyl}-amide (149 mg, 0.25 mmol) as an off-white solid (22 mg, 19%).

HPLC (Method A, ELSD): Rt 2.52 min (Purity 98.9%). LCMS (Method A, ELSD): 474.3 (M+H). $^1$H NMR (400 MHz, DMSO-$d_6$): δ 9.33 (t, J=4.0 Hz, 1H), 7.83 (t, J=4.0 Hz, 1H), 7.27-7.19 (m, 2H), 6.85-6.80 (m, 3H), 5.33 (d, J=8.0 Hz, 1H), 4.42 (t, J=4.0 Hz, 1H), 4.3 (d, J=8.0 Hz, 2H), 3.72 (d, J=8.0 Hz, 2H), 3.36-3.25 (m, 6H), 3.02 (dd, J=4.0, 8.0 Hz, 3H), 2.92 (s, 3H), 0.79 (m, 3H), 0.76 (m, 3H).

Example 27

(R)—N-[3-(Benzyl-methyl-carbamoyl-3-oxo-propyl]-2,4-dihydroxy-3,3-dimethyl-butyramide

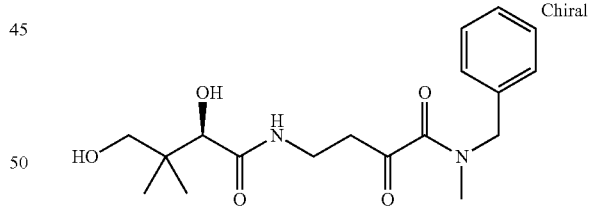

(R)—N-[3-(Benzyl-methyl-carbamoyl)-3-oxo-propyl]-2,4-dihydroxy-3,3-dimethyl-butyramide was synthesized following the general procedure B starting from (R)-2-(4-methoxy-phenyl)-5,5-di methyl-[1,3]dioxane-4-carboxylic acid [3-(benzyl-ethyl-carbamoyl)-3-hydroxy-propyl]-amide (108 mg, 0.23 mmol) as an off-white gum (26 mg, 32%).

HPLC (Method A): Rt 3.13 min (Purity 92.1%). LCMS (Method A): 351.0 (M+H). $^1$H NMR (400 MHz, DMSO-$d_6$): δ 7.80-7.76 (m, 1H), 7.39-7.24 (m, 5H), 5.42 (t, J=4.0 Hz, 1H), 4.52 (s, 1H), 4.43 (t, J=4.0 Hz, 2H), 3.73 (dd, J=4.0, 8.0 Hz, 1H), 3.41-3.37 (m, 1H), 3.28-3.25 (m, 2H), 3.17-3.13 (m, 1H), 3.00-2.85 (m, 2H), 2.75-2.50 (m, 3H), 0.79 (m, 3H), 0.75 (m, 3H).

Example 28

(R)—N-{3-[(Biphenyl-4-ylmethyl)-carbamoyl]-3-oxo-propyl}-2,4-dihydroxy-3,3-dimethyl-butyramide

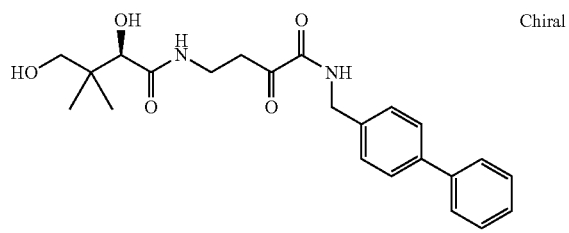 [SMILES: CC(C)(CO)[C@@H](O)C(=O)NCCC(=O)C(=O)NCc1ccc(-c2ccccc2)cc1]

(R)—N-{3-[(Biphenyl-4-ylmethyl)-carbamoyl]-3-oxo-propyl}-2,4-dihydroxy-3,3-dimethyl-butyramide was synthesized following the general procedure B starting from (R)-2-(4-methoxy-phenyl)-5,5-dimethyl-[1,3]dioxane-4-carboxylic acid {3-[(biphenyl-4-lmethyl)-carbamoyl]-3-hydroxy-propyl}-amide (75 mg, 0.14 mmol) as a pale yellow solid (9 mg, 16%).

HPLC (Method A): Rt 3.94 min (Purity 96.5%). LCMS (Method A): 413.3 (M+H). $^1$H NMR (400 MHz, DMSO-$d_6$): δ 9.32-9.18 (m, 1H), 7.73 (t, J=4.0 Hz, 1H), 7.63-7.58 (m, 4H), 7.46-7.42 (m, 2H), 7.36-7.32 (m, 3H), 5.34 (d, J=8.0 Hz, 1H), 4.53 (t, J=4.0 Hz, 1H), 4.32 (d, J=8.0 Hz, 2H), 3.73 (d, J=4.0 Hz, 1H), 3.37-3.25 (m, 3H), 3.12 (dd, J=4.0, 8.0 Hz, 1H), 3.01-2.98 (m, 2H), 0.78 (m, 3H), 0.76 (m, 3H).

Example 29

(R)-2,4-Dihydroxy-3,3-dimethyl-N-(3-oxo-3-[(tetrahydro-furan-2-ylmethyl)-carbamoyl]-propyl)-butyramide

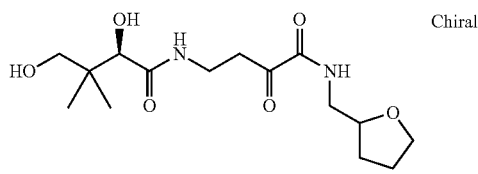 [SMILES: CC(C)(CO)[C@@H](O)C(=O)NCCC(=O)C(=O)NCC1CCCO1]

(R)-2,4-Dihydroxy-3,3-dimethyl-N-{3-oxo-3-[(tetrahydro-furan-2-ylmethyl)-carbamoyl]-propyl}-butyramide was synthesized following the general procedure B starting from (R)-2-(4-methoxy-phenyl)-5,5-dimethyl-[1,3]dioxane-4-carboxylic acid {3-hydroxy-3-(tetrahydro-furan-2-ylmethyl)-carbamoyl]-propyl}-amide (132 mg, 0.29 mmol) as an off-white gum (37 mg, 38%).

HPLC (Method A, ELSD): Rt 1.95 min (Purity 99%). LCMS (Method A ELSD): 331.3 (M+H). $^1$H NMR (400 MHz, DMSO-$d_6$): δ 8.65-8.55 (m, 1H), 7.85-7.83 (m, 1H), 5.33 (d, J=8.0 Hz, 1H), 4.43 (t, J=4.0 Hz, 1H), 3.93 (t, J=4.0 Hz, 1H), 3.73-3.72 (m, 3H), 3.67-3.57 (m, 3H), 3.31-3.12 (m, 3H), 2.97-2.94 (m, 2H), 1.83-1.77 (m, 1H), 1.65-1.62 (m, 1H), 0.79 (m, 3H), 0.77 (m, 3H).

Example 30

(R)-2,4-Dihydroxy-N-{3-[2-(4-methanesulfonyl-phenyl)-ethylcarbamoyl]-3-oxo-propyl}-3,3-dimethyl-butyramide

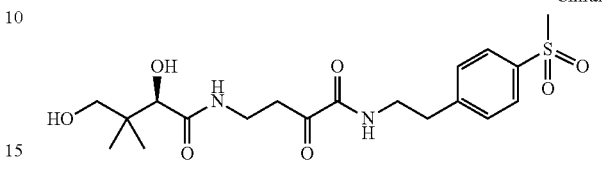

(R)-2,4-Dihydroxy-N-{3-[2-(4-methanesulfonyl-phenyl)-ethylcarbamoyl]-3-oxo-propyl}-3,3-dimethyl-butyramide was synthesized following the general procedure B starting from (R)-2-(4-methoxy-phenyl)-5,5-dimethyl-[1,3]dioxane-4-carboxylic acid {3-hydroxy-3-2-4-methanesulfonyl-phenyl)-ethylcarbamoyl]-propyl}-amide (64 mg, 0.12 mmol) as a colorless gum (11 mg, 22%).

HPLC (Method A): Rt 3.46 min (Purity 94.7%). LCMS (Method A): 429.0 (M+H). $^1$H NMR (400 MHz, DMSO-$d_6$): δ 8.74 (t, J=4.0 Hz, 1H), 7.83-7.73 (m, 3H), 7.53 (d, J=8.0 Hz, 2H), 5.32 (d, J=8.0 Hz, 1H), 4.43 (t, J=4.0 Hz, 1H), 3.73 (d, J=4.0 Hz, 1H), 3.38-3.25 (m, 4H), 3.16-3.12 (m, 4H), 2.96-2.86 (m, 3H), 2.50-2.49 (m, 2H), 0.78 (s, 3H), 0.77 (s, 3H).

Example 31

(R)—N-[3-(4-Bromo-benzylcarbamoyl)-3-oxo-propyl]-2,4-dihydroxy-3,3-dimethyl-butyramide

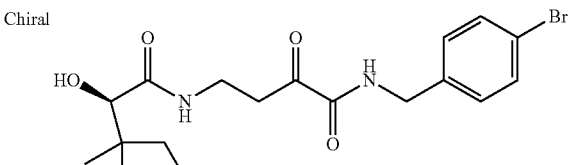

(R)—N-[3-(4-Bromo-benzylcarbamoyl)-3-oxo-propyl]-2,4-dihydroxy-3,3-di methyl-butyramide was synthesized following the general procedure B starting from (R)-2-(4-methoxy-phenyl)-5,5-dimethyl-[1,3]dioxane-4-carboxylic acid [3-(4-bromo-benzylcarbamoyl)-3-hydroxy-propyl]-amide (44 mg, 0.08 mmol) as a pale yellow solid (11 mg, 32%).

HPLC (Method B): Rt 4.64 min (Purity 92.55%). LCMS (Method B): 417.0 (M+H). $^1$H NMR (400 MHz, DMSO-$d_6$): δ 9.14 (t, J=4.0 Hz, 1H), 7.80 (t, J=4.0 Hz, 1H), 7.53 (dd, J=4.0, 6.6 Hz, 2H), 7.23 (d, J=8.0 Hz, 2H), 5.30 (d, J=8.0 Hz, 1H), 4.40 (t, J=4.0 Hz, 1H), 4.34 (d, J=8.0 Hz, 2H), 3.74 (d, J=8.0 Hz, 1H), 3.33-3.25 (m, 3H), 3.23 (t, J=4.0 Hz, 1H), 2.99-2.97 (m, 2H), 0.78 (s, 3H), 0.77 (s, 3H).

Example 32

4-{[4-((R)-2,4-Dihydroxy-3,3-dimethyl-butyrylamino)-2-oxo-butyrylamino]-methyl}-N-[2-(4-phenoxy-phenyl)-ethyl]-benzamide

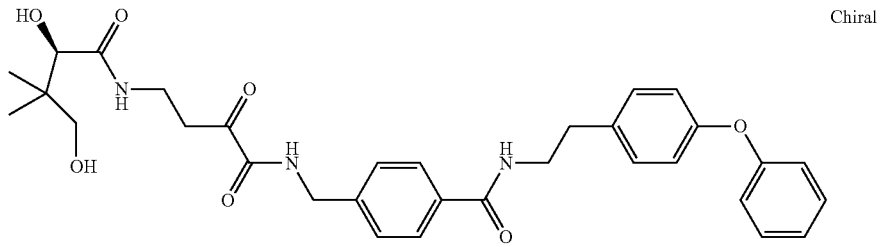 [SMILES: CC(C)(CO)[C@@H](O)C(=O)NCCC(=O)C(=O)NCc1ccc(C(=O)NCCc2ccc(Oc3ccccc3)cc2)cc1]

4-{[4-((R)-2,4-Dihydroxy-3,3-dimethyl-butyrylamino)-2-oxo-butyrylamino]-methyl}-N-[2-(4-phenoxy-phenyl)-ethyl]-benzamide was synthesized following the general procedure B starting from (R)-2-(4-methoxy-phenyl)-5,5-dimethyl-[1,3]dioxane-4-carboxylic acid (3-hydroxy-3-4-2-(4-phenoxy-phenyl)-ethylcarbamoyl]-benzylcarbamoyl}-propyl)-amide (159 mg, 0.28 mmol) as a white solid (40 mg, 38%).

HPLC (Method B): Rt 5.49 min (Purity 92.11%). LCMS (Method B): 576.2 (M+H). $^1$H NMR (400 MHz, DMSO-d$_6$): δ 9.14-9.10 (m, 1H), 8.50-8.45 (m, 1H), 7.78-7.73 (m, 3H), 7.38-7.32 (m, 4H), 7.24 (d, J=8.4 Hz, 2H), 7.10 (s, 1H), 6.97-6.92 (m, 4H), 5.34 (d, J=5.3 Hz, 1H), 4.45 (s, 1H), 3.68 (d, J=5.6 Hz, 2H), 3.47-3.37 (m, 7H), 3.00 (t, J=4.0 Hz, 2H), 2.81 (t, J=7.2 Hz, 2H), 0.78 (s, 3H), 0.77 (s, 3H).

Example 33

(R)-2,4-Dihydroxy-3,3-dimethyl-N-{3-oxo-3-[4-(piperidine-1-sulfonyl)-benzylcarbamoyl]-propyl}-butyramide

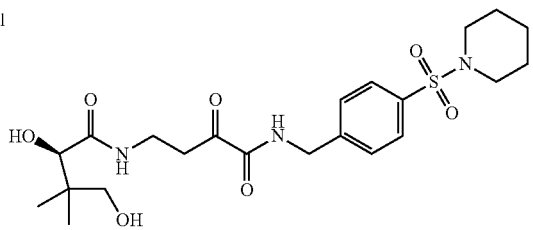

(R)-2,4-Dihydroxy-3,3-dimethyl-N-{3-oxo-3-[4-(piperidine-1-sulfonyl)-benzylcarbamoyl]-propyl}-butyramide was synthesized following the general procedure B starting from (R)-2-(4-methoxy-phenyl)-5,5-dimethyl-[1,3]dioxane-4-carboxylic acid {3-hydroxy-3-4-piperidine-1-sulfonyl)-benzylcarbamoyl]-propyl}-amide (125 mg, 0.21 mmol) as a white solid (58 mg, 50%).

HPLC (Method B): Rt 4.65 min (Purity 97.48%). LCMS (Method B): 484.0 (M+H). $^1$H NMR (400 MHz, DMSO-d$_6$): δ 9.20-9.19 (m, 1H), 7.85-7.82 (m, 1H), 7.65 (d, J=8.4 Hz, 2H), 7.51 (d, J=8.3 Hz, 2H), 5.35 (d, J=5.6 Hz, 1H), 4.45-4.40 (m, 3H), 3.68 (d, J=5.6 Hz, 1H), 3.36-3.17 (m, 4H), 2.99 (t, J=4.0 Hz, 2H), 2.84 (t, J=5.0 Hz, 4H), 1.52 (t, J=5.0 Hz, 6H), 0.78 (s, 3H), 0.77 (s, 3H).

Example 34

(R)—N-(3-[(1-Benzenesulfonyl-piperidin-4-ylmethyl)-carbamoyl]-3-oxo-propyl)-2,4-dihydroxy-3,3-dimethyl-butyramide

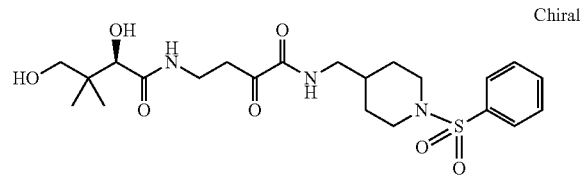 [SMILES: CC(C)(CO)[C@@H](O)C(=O)NCCC(=O)C(=O)NCC1CCN(S(=O)(=O)c2ccccc2)CC1]

(R)—N-{3-[(1-Benzenesulfonyl-piperidin-4-ylmethyl)-carbamoyl]-3-oxo-propyl}-2,4-dihydroxy-3,3-dimethyl-butyramide was synthesized following the general procedure B starting from (R)-2-(4-methoxy-phenyl)-5,5-dimethyl-[1,3]dioxane-4-carboxylic acid {3-[(1-benzenesulfonyl-piperidin-4-ylmethyl)-carbamoyl]-3-hydroxy-propyl}-amide (260 mg, 0.43 mmol) as a white solid (184 mg, 88%).

HPLC (Method B): Rt 4.46 min (Purity 96.97%). LCMS (Method B): 484.0 (M+H). $^1$H NMR (400 MHz, DMSO-d$_6$): δ 8.54-8.52 (m, 1H), 7.74-7.61 (m, 6H), 6.67 (d, J=5.6 Hz, 1H), 4.43 (t, J=5.6 Hz, 1H), 3.67-3.57 (m, 3H), 3.57-3.48 (m, 4H), 2.96-2.91 (m, 4H), 2.18 (d, J=2.4 Hz, 2H), 1.66-1.63 (m, 2H), 1.51-1.42 (m, 1H), 1.21-1.01 (m, 2H), 0.77 (s, 3H), 0.76 (s, 3H).

Example 35

(R)-2,4-Dihydroxy-3,3-dimethyl-N-(3-oxo-3-{3-[4-(piperidine-1-sulfonyl)-phenyl]-propylcarbamoyl}-propyl)-butyramide

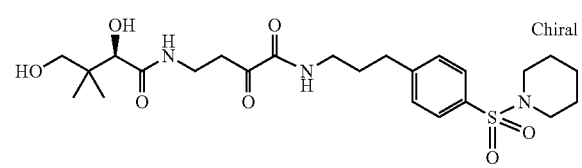 [SMILES: CC(C)(CO)[C@@H](O)C(=O)NCCC(=O)C(=O)NCCCc1ccc(S(=O)(=O)N2CCCCC2)cc1]

(R)-2,4-Dihydroxy-3,3-dimethyl-N-(3-oxo-3-{3-[4-(piperidine-1-sulfonyl)-phenyl]-propylcarbamoyl}-propyl)-butyramide was synthesized following the general procedure B starting from (R)-2-(4-methoxy-phenyl)-5,5-dimethyl-[1,3]dioxane-4-carboxylic acid (3-hydroxy-3-3-3-(piperidine-1-sulfonyl)-phenyl]-propylcarbamoyl}-propyl)-amide (111 mg, 0.18 mmol) as a colorless gum (19 mg, 21%).

HPLC (Method B): Rt 5.01 min (Purity 86.53%). LCMS (Method B): 512.3 (M+H). $^1$H NMR (400 MHz, DMSO-$d_6$): δ 8.63-8.61 (m, 1H), 7.62 (d, J=8.3 Hz, 3H), 7.46 (d, J=8.3 Hz, 2H), 5.34 (d, J=5.5 Hz, 1H), 4.45 (d, J=5.60 Hz, 1H), 3.67 (d, J=5.5 Hz, 1H), 3.32-3.11 (m, 5H), 2.98-2.94 (m, 2H), 2.85-2.83 (m, 4H), 2.67-2.65 (m, 2H), 2.50-2.46 (m, 1H), 1.78 (t, J=7.1 Hz, 2H), 1.51 (t, J=5.6 Hz, 4H), 1.34 (d, J=4.4 Hz, 2H), 0.77 (s, 3H), 0.76 (s, 3H).

Example 36

(R)-2,4-Dihydroxy-3,3-dimethyl-N-{3-oxo-3-[3-(piperidine-1-sulfonyl)-benzylcarbamoyl}-propyl)-butyramide

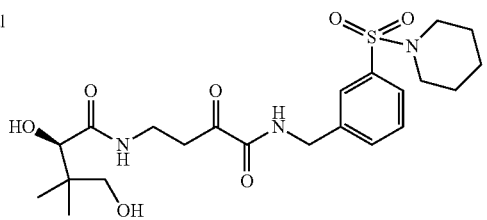

(R)-2,4-Dihydroxy-3,3-dimethyl-N-{3-oxo-3-[3-(piperidine-1-sulfonyl)-benzylcarbamoyl]-propyl}-butyramide was synthesized following the general procedure B starting from (R)-2-(4-methoxy-phenyl)-5,5-dimethyl-[1,3]dioxane-4-carboxylic acid {3-hydroxy-3-3-piperidine-1-sulfonyl)-benzylcarbamoyl]-propyl}-amide (107 mg, 0.18 mmol) as a white solid (60 mg, 70%).

HPLC (Method B): Rt 4.27 min (Purity 98.5%). LCMS (Method B): 484.0 (M+H). $^1$H NMR (400 MHz, DMSO-$d_6$): δ 9.22-9.21 (m, 1H), 7.64-7.58 (m, 5H), 5.33 (d, J=5.2 Hz, 1H), 4.45-4.40 (m, 3H), 3.67 (d, J=5.6 Hz, 1H), 3.68-3.58 (m, 4H), 2.99-2.96 (m, 2H), 2.86-2.84 (m, 4H), 1.53-1.43 (m, 4H), 1.32-1.30 (m, 2H), 0.77 (s, 3H), 0.76 (s, 3H).

Example 37

(R)-2,4-Dihydroxy-3,3-dimethyl-N-{3-oxo-3-[4-(pyridin-4-yloxy)-benzylcarbamoyl]-propyl}-butyramide

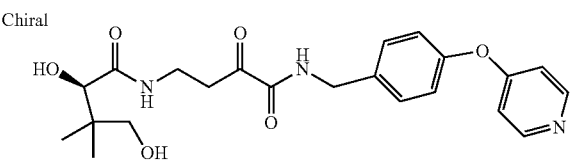 [SMILES: CC(C)(CO)[C@@H](O)C(=O)NCCC(=O)C(=O)NCc1ccc(Oc2ccncc2)cc1]

(R)-2,4-Dihydroxy-3,3-dimethyl-N-{3-oxo-3-[4-(pyridin-4-yloxy)-benzylcarbamoyl]-propyl}-butyramide was synthesized following the general procedure B starting from (R)-2-(4-methoxy-phenyl)-5,5-dimethyl-[1,3]dioxane-4-carboxylic acid {3-hydroxy-3-4-pyridin-4-yloxy)-benzylcarbamoyl]-propyl}-amide (146 mg, 0.26 mmol) as a white solid (86 mg, 75%).

HPLC (Method B): Rt 4.17 min (Purity 96.38%). LCMS (Method B): 430.0 (M+H). $^1$H NMR (400 MHz, DMSO-$d_6$): δ 9.14-9.12 (m, 1H), 8.44-8.43 (m, 2H), 7.38 (d, J=8.4 Hz, 3H), 7.13-7.11 (m, 2H), 6.89-6.87 (m, 2H), 5.34 (d, J=5.6 Hz, 1H), 4.45 (d, J=5.6 Hz, 1H), 4.34 (d, J=6.4 Hz, 2H), 4.03 (t, J=4.0 Hz, 2H), 3.32-3.13 (m, 3H), 3.02-2.98 (m, 2H), 0.77 (s, 3H), 0.76 (s, 3H).

Example 38

(R)—N-(3-{[1-(Biphenyl-4-sulfonyl)-piperidin-4-ylmethyl]-carbamoyl}-3-oxo-propyl)-2,4-dihydroxy-3,3-dimethyl-butyramide

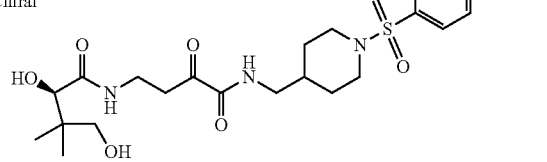

(R)—N-(3-{[1-(Biphenyl-4-sulfonyl)-piperidin-4-ylmethyl]-carbamoyl}-3-oxo-propyl)-2,4-dihydroxy-3,3-dimethyl-butyramide was synthesized following the general procedure B starting from (R)-2-(4-methoxy-phenyl)-5,5-dimethyl-[1,3]dioxane-4-carboxylic acid (3-{[1-(biphenyl-4-sulfonyl)-piperidin-4-ylmethyl]-carbamoyl}-3-hydroxy-propyl)-amide (124 mg, 0.18 mmol) as a white solid (99 mg, 97%). 37

HPLC (Method B): Rt 5.54 min (Purity 97.27%). LCMS (Method B): 560.3 (M+H). $^1$H NMR (400 MHz, DMSO-$d_6$): δ 8.55-8.52 (m, 1H), 7.93-7.91 (m, 2H), 7.80-7.74 (m, 5H), 7.54-7.44 (m, 3H), 5.32 (d, J=5.5 Hz, 1H), 4.43 (s, 1H), 3.66-3.61 (m, 4H), 3.32-3.23 (m, 4H), 2.98-2.92 (m, 3H), 2.24 (d, J=1.92 Hz, 2H), 1.76-1.66 (m, 2H), 1.53-1.43 (m, 1H), 1.18-1.15 (m, 2H), 0.76 (s, 3H), 0.75 (s, 3H).

Example 39

(R)-2,4-Dihydroxy-N-(3-[4-(2-methanesulfonylamino-ethoxy)-benzylcarbamoyl]-3-oxo-propyl)-3,3-dimethyl-butyramide

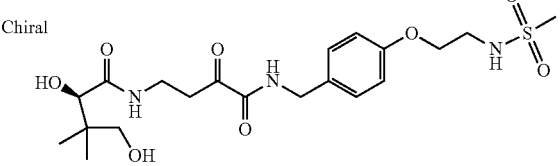

(R)-2,4-Dihydroxy-N-{3-[4-(2-methanesulfonylamino-ethoxy)-benzylcarbamoyl]-3-oxo-propyl}-3,3-dimethyl-butyramide was synthesized following the general procedure B starting from (R)-2-(4-methoxy-phenyl)-5,5-dimethyl-[1,3]dioxane-4-carboxylic acid {3-hydroxy-3-[4-(2-methanesulfonylamino-ethoxy)-benzylcarbamoyl]-propyl}-amide (97 mg, 0.16 mmol) as a colorless liquid (14 mg, 18%).

HPLC (Method B): Rt 3.63 min (Purity 99.18%). LCMS (Method B): 474.0 (M+H). $^1$H NMR (400 MHz, DMSO-d$_6$): δ 9.12-9.10 (m, 1H), 7.78-7.76 (m, 1H), 7.18 (d, J=4.0 Hz, 3H), 6.87 (d, J=4.8 Hz, 2H), 5.34 (d, J=5.2 Hz, 1H), 4.44 (t, J=4.0 Hz, 1H), 4.22 (d, J=6.2 Hz, 2H), 3.98 (t, J=5.7 Hz, 2H), 3.67 (d, J=5.6 Hz, 2H), 3.36-3.15 (m, 5H), 2.98 (d, J=5.00 Hz, 2H), 2.93 (s, 3H), 0.77 (s, 3H), 0.76 (s, 3H).

Example 40

(R)-2,4-Dihydroxy-3,3-dimethyl-N-{3-oxo-3-[3-(3-oxo-morpholin-4-yl)-propylcarbamoyl]-propyl)butyramide

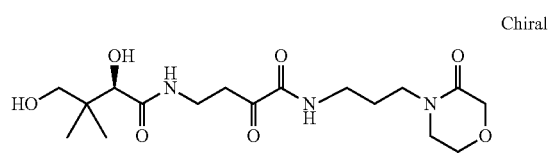 [SMILES: CC(C)(CO)[C@@H](O)C(=O)NCCC(=O)C(=O)NCCCN1CCOCC1=O]

(R)-2,4-Dihydroxy-3,3-dimethyl-N-{3-oxo-3-[3-(3-oxo-morpholin-4-yl)-propylcarbamoyl]-propyl}-butyramide was synthesized following the general procedure B starting from (R)-2-(4-methoxy-phenyl)-5,5-dimethyl-[1,3]dioxane-4-carboxylic acid {3-hydroxy-3-3-3-oxo-morpholin-4-yl)-propylcarbamoyl]-propyl}-amide (94 mg, 0.18 mmol) as a brown gum (28 mg, 39%).

HPLC (Method B): Rt 2.71 min (Purity 95.79%). LCMS (Method B): 388.3 (M+H). $^1$H NMR (400 MHz, DMSO-d$_6$): δ 8.65-8.64 (m, 1H), 7.85-7.83 (m, 1H), 5.34 (d, J=5.5 Hz, 1H), 4.44 (t, J=5.6 Hz, 1H), 4.00 (s, 2H), 3.80 (t, J=5.2 Hz, 2H), 3.67 (d, J=5.6 Hz, 1H), 3.35-3.25 (m, 7H), 3.17-2.94 (m, 5H), 1.67 (t, J=6.8 Hz, 2H), 0.77 (s, 3H), 0.76 (s, 3H).

Example 41

(R)-2,4-Dihydroxy-3,3-dimethyl-N-[3-(4-morpholin-4-yl-benzylcarbamoyl)-3-oxo-propyl]-butyramide

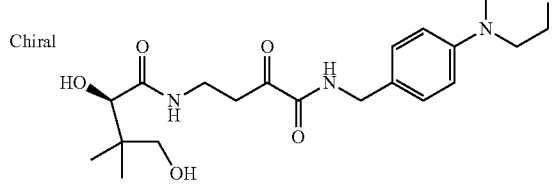

(R)-2,4-Dihydroxy-3,3-dimethyl-N-[3-(4-morpholin-4-yl-benzylcarbamoyl)-3-oxo-propyl]-butyramide was synthesized following the general procedure B starting from (R)-2-(4-methoxy-phenyl)-5,5-dimethyl-[1,3]dioxane-4-carboxylic acid [3-hydroxy-3-4-morpholin-4-yl-benzylcarbamoyl)-propyl]-amide (95 mg, 0.18 mmol) as a brown gum (29 mg, 39%).

HPLC (Method B): Rt 3.75 min (Purity 95.51%). LCMS (Method B): 422.2 (M+H). $^1$H NMR (400 MHz, DMSO-d$_6$): δ 9.01-8.98 (m, 1H), 7.76-7.75 (m, 1H), 7.13 (d, J=8.8 Hz, 2H), 6.86 (d, J=8.8 Hz, 2H), 5.33 (d, J=5.6 Hz, 1H), 4.44 (t, J=5.6 Hz, 1H), 4.19 (d, J=6.3 Hz, 2H), 3.72-3.66 (m, 5H), 3.32-3.25 (m, 3H), 3.17-3.13 (m, 1H), 3.05-2.86 (m, 6H), 0.77 (s, 3H), 0.76 (s, 3H).

Example 42

(R)-2,4-Dihydroxy-3,3-dimethyl-N-[3-oxo-3-(2-phenoxy-ethylcarbamoyl)-propyl]-butyramide

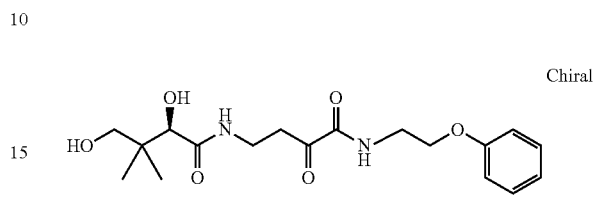

(R)-2,4-Dihydroxy-3,3-dimethyl-N-[3-oxo-3-(2-phenoxy-ethylcarbamoyl)-propyl]-butyramide was synthesized following the general procedure B starting from (R)-2-(4-methoxy-phenyl)-5,5-dimethyl-[1,3]dioxane-4-carboxylic acid [3-hydroxy-3-(2-phenoxy-ethylcarbamoyl)-propyl]-amide (81 mg, 0.17 mmol) as a colorless liquid (11 mg, 18%).

HPLC (Method B): Rt 4.29 min (Purity 95.56%). LCMS (Method B): 367.3 (M+H). $^1$H NMR (400 MHz, DMSO-d$_6$): δ 8.75-8.70 (m, 1H), 7.75-7.70 (m, 1H), 7.29-7.25 (m, 2H), 6.94-6.91 (m, 3H), 5.34 (d, J=5.6 Hz, 1H), 4.44 (t, J=5.6 Hz, 1H), 4.03 (t, J=5.9 Hz, 2H), 3.67 (d, J=5.2 Hz, 1H), 3.50-3.25 (m, 5H), 3.15 (t, J=5.0 Hz, 1H), 3.00-2.96 (m, 2H), 0.77 (s, 3H), 0.76 (s, 3H).

Example 43

(R)—N-{3,4-Dioxo-4-[4-(3-trifluoromethanesulfonyl-phenylamino)-piperidin-1-yl]-butyl}-2,4-dihydroxy-3,3-dimethyl-butyramide

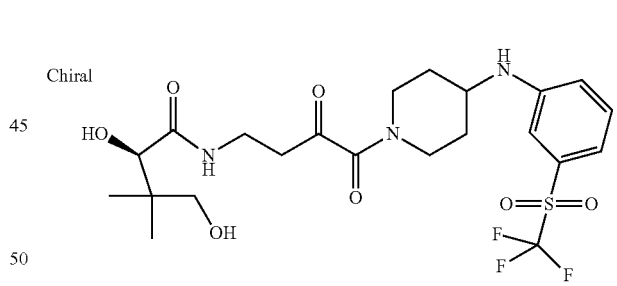

(R)—N-{3,4-Dioxo-4-[4-(3-trifluoromethanesulfonyl-phenylamino)-piperidin-1-yl]-butyl}-2,4-dihydroxy-3,3-dimethyl-butyramide was synthesized following the general procedure B starting from (R)-2-(4-methoxy-phenyl)-5,5-dimethyl-[1,3]dioxane-4-carboxylic acid {3-hydroxy-4-oxo-4-[4-(3-trifluoromethanesulfonyl-phenylamino)-piperidin-1-yl]-butyl}-amide (143 mg, 0.26 mmol) as an off-white solid (77 mg, 66%).

HPLC (Method B): Rt 5.55 min (Purity 97.61%). LCMS (Method A): 538.0 (M+H). $^1$H NMR (400 MHz, DMSO-d$_6$): δ 7.76 (t, J=5.6 Hz, 1H), 7.50 (t, J=7.9 Hz, 1H), 7.19-7.15 (m, 3H), 6.58 (d, J=8.0 Hz, 1H), 5.39-5.37 (m, 1H), 4.30-4.29 (m, 1H), 4.10-4.09 (m, 1H), 3.70-3.62 (m, 3H), 3.40-3.24 (m, 6H), 2.93 (t, J=6.6 Hz, 2H), 1.94-1.90 (m, 2H), 1.41-1.11 (m, 2H), 0.78 (s, 3H), 0.77 (s, 3H).

Example 44

(R)-2,4-Dihydroxy-3,3-dimethyl-N-(3-[4-(2-morpholin-4-yl-ethoxy)-benzylcarbamoyl]-3-oxo-propyl)-butyramide

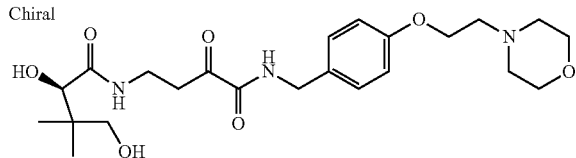 [SMILES: CC(C)(CO)[C@@H](O)C(=O)NCCC(=O)C(=O)NCc1ccc(OCCN2CCOCC2)cc1]

(R)-2,4-Dihydroxy-3,3-dimethyl-N-{3-[4-(2-morpholin-4-yl-ethoxy)-benzylcarbamoyl]-3-oxo-propyl}-butyramide was synthesized following the general procedure B starting from (R)-2-(4-methoxy-phenyl)-5,5-dimethyl-[1,3]dioxane-4-carboxylic acid {3-hydroxy-3-4-2-morpholin-4-yl-ethoxy)-benzylcarbamoyl]-propyl}-amide (54 mg, 0.1 mmol) as a colorless gum (27 mg, 63%).

HPLC (Method B): Rt 3.79 min (Purity 93.47%). LCMS (Method B): 466.3 (M+H). $^1$H NMR (400 MHz, DMSO-$d_6$): δ 9.10-9.02 (m, 1H), 7.75-7.72 (m, 1H), 7.17 (d, J=4.0 Hz, 2H), 6.86 (d, J=8.4 Hz, 2H), 5.34 (d, J=5.6 Hz, 1H), 4.44 (t, J=5.6 Hz, 1H), 4.22 (d, J=6.3 Hz, 2H), 4.03 (t, J=5.7 Hz, 2H), 3.62-3.61 (m, 1H), 3.56 (t, J=4.4 Hz, 4H), 3.38-3.13 (m, 4H), 3.00-2.96 (m, 2H), 2.65 (t, J=5.6 Hz, 2H), 2.50-2.44 (m, 4H), 0.78 (s, 3H), 0.77 (s, 3H).

Example 45

4-{[4-((R)-2,4-Dihydroxy-3,3-dimethyl-butyrylamino)-2-oxo-butyrylamino]-methyl}-benzoic acid ethyl ester

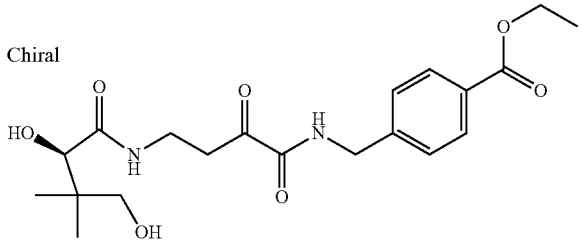 [SMILES: CCOC(=O)c1ccc(CNC(=O)C(=O)CCNC(=O)[C@H](O)C(C)(C)CO)cc1]

4-{[4-((R)-2,4-Dihydroxy-3,3-dimethyl-butyrylamino)-2-oxo-butyrylamino]-methyl}-benzoic acid ethyl ester was synthesized following the general procedure B starting from 4-[(2-hydroxy-4-{[(R)-2-(4-methoxy-phenyl)-5,5-dimethyl-[1,3]dioxane-4-carbonyl]amino}-butyrylamino)-methyl]-benzoic acid ethyl ester (49 mg, 0.1 mmol) as a white solid (17 mg, 45%).

HPLC (Method B): Rt 4.40 min (Purity 95.88%). LCMS (Method B): 409.2 (M+H). $^1$H NMR (400 MHz, DMSO-$d_6$): δ 9.28-9.26 (m, 1H), 7.89 (d, J=6.4 Hz, 2H), 7.82-7.80 (m, 1H), 7.40 (d, J=8.4 Hz, 2H), 5.35 (d, J=5.6 Hz, 1H), 4.45 (t, J=5.6 Hz, 1H), 4.36 (t, J=8.0 Hz, 2H), 4.28 (t, J=7.2 Hz, 2H), 3.68 (d, J=5.6 Hz, 1H), 3.37-3.25 (m, 3H), 3.16 (t, J=5.2 Hz, 1H), 3.00-2.97 (m, 2H), 1.30 (t, J=7.0 Hz, 3H), 0.78 (s, 3H), 0.77 (s, 3H).

Example 46

(R)-2,4-Dihydroxy-3,3-dimethyl-N-[3-oxo-3-({1-[4-(2-oxo-pyrrolidin-1-yl)-benzenesulfonyl]-piperidin-4-ylmethyl}-carbamoyl)-propyl]-butyramide

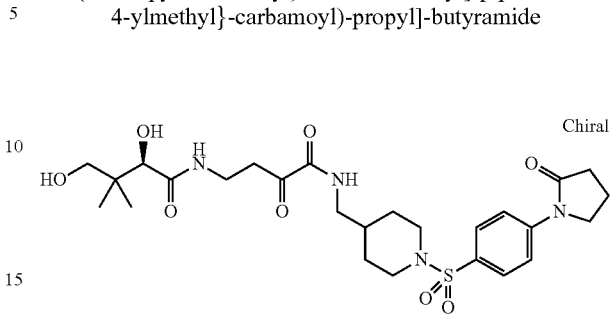

(R)-2,4-Dihydroxy-3,3-dimethyl-N-[3-oxo-3-({1-[4-(2-oxo-pyrrolidin-1-yl)-benzenesulfonyl]-piperidin-4-ylmethyl}-carbamoyl)-propyl]-butyramide was synthesized following the general procedure B starting from (R)-2-(4-methoxy-phenyl)-5,5-dimethyl-[1,3]dioxane-4-carboxylic acid [3-hydroxy-3-{1-[4-(2-oxo-pyrrolidin-1-yl)-benzenesulfonyl]-piperidin-4-ylmethyl}-carbamoyl)-propyl]-amide (200 mg, 0.29 mmol) as a white solid (33 mg, 20%).

HPLC (Method B): Rt 4.21 min (Purity 98.52%). LCMS (Method B): 567.0 (M+H). $^1$H NMR (400 MHz, DMSO-$d_6$): δ 8.65-8.62 (m, 1H), 7.91 (d, J=5.2 Hz, 2H), 7.90-7.69 (m, 3H), 5.33 (d, J=5.5 Hz, 1H), 3.87 (t, J=7.2 Hz, 2H), 3.66 (d, J=5.5 Hz, 1H), 3.56 (d, J=8.0 Hz, 2H), 3.32-3.14 (m, 4H), 2.97-2.92 (m, 4H), 2.56-2.51 (m, 3H), 2.15-2.05 (m, 4H), 1.71-1.62 (m, 2H), 1.49-1.32 (m, 1H), 1.17-1.05 (m, 2H), 0.76 (s, 3H), 0.75 (s, 3H).

Example 47

(R)-2,4-Dihydroxy-N-(3-[(1-methanesulfonyl-piperidin-4-ylmethyl)-carbamoyl]-3-oxo-propyl)-3,3-dimethyl-butyramide

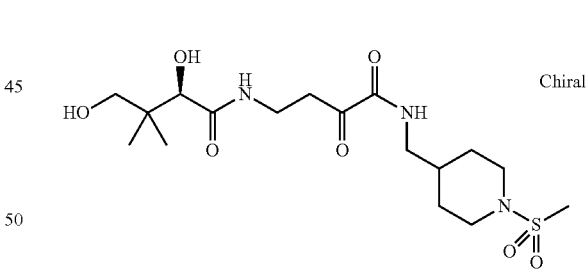

(R)-2,4-Dihydroxy-N-{3-[(1-methanesulfonyl-piperidin-4-ylmethyl)-carbamoyl]-3-oxo-propyl}-3,3-dimethyl-butyramide was synthesized following the general procedure B starting from (R)-2-(4-methoxy-phenyl)-5,5-dimethyl-[1,3]dioxane-4-carboxylic acid {3-hydroxy-3-(1-methanesulfonyl-piperidin-4-ylmethyl)-carbamoyl]-propyl}-amide (128 mg, 0.24 mmol) as an off-white gum (50 mg, 50%).

HPLC (Method B): Rt 3.21 min (Purity 98.08%). LCMS (Method B): 422.2 (M+H). $^1$H NMR (400 MHz, DMSO-$d_6$): δ 8.80-8.76 (m, 1H), 7.75-7.72 (m, 1H), 5.34 (d, J=5.5 Hz, 1H), 4.44 (t, J=5.6 Hz, 1H), 3.67 (d, J=5.6 Hz, 1H), 3.51 (d, J=8.0 Hz, 2H), 3.37-3.25 (m, 3H), 3.16-3.12 (m, 2H), 3.04-2.94 (m, 3H), 2.82 (s, 3H), 2.69-2.59 (m, 2H), 1.71-1.55 (m, 3H), 1.15-1.12 (m, 2H), 0.78 (d, 3H), 0.77 (d, 3H).

Example 48

(R)—N-(3-[(1-Acetyl-piperidin-4-ylmethyl)-carbamoyl]-3-oxo-propyl)-2,4-dihydroxy-3,3-dimethyl-butyramide

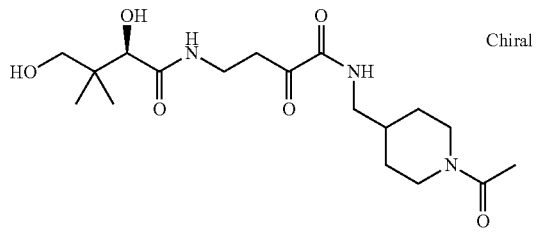 [SMILES: CC(=O)N1CCC(CNC(=O)C(=O)CCNC(=O)[C@H](O)C(C)(C)CO)CC1]

(R)—N-{3-[(1-Acetyl-piperidin-4-ylmethyl)-carbamoyl]-3-oxo-propyl}-2,4-dihydroxy-3,3-dimethyl-butyramide was synthesized following the general procedure B starting from (R)-2-(4-methoxy-phenyl)-5,5-dimethyl-[1,3]dioxane-4-carboxylic acid {3-[(1-acetyl-piperidin-4-ylmethyl)-carbamoyl]-3-hydroxy-propyl}-amide (139 mg, 0.26 mmol) as a yellow gum (72 mg, 68%).

HPLC (Method B): Rt 2.92 min (Purity 97.15%). LCMS (Method B): 386.3 (M+H). $^1$H NMR (400 MHz, DMSO-$d_6$): δ 8.60-8.58 (m, 1H), 7.75-7.72 (m, 1H), 5.34 (d, J=5.4 Hz, 1H), 4.44 (t, J=5.6 Hz, 1H), 4.30 (d, J=8.0 Hz, 1H), 3.75 (d, J=8.0 Hz, 1H), 3.67 (d, J=5.5 Hz, 1H), 3.37-2.93 (m, 8H), 2.51-2.44 (m, 1H), 1.95 (s, 3H), 1.90 (s, 1H), 1.56-1.60 (m, 3H), 1.06-0.88 (m, 2H), 0.77 (s, 3H), 0.76 (s, 3H).

Example 49

(R)-2,4-Dihydroxy-3,3-dimethyl-N-(4-morpholin-4-yl-3,4-dioxo-butyl)-butyramide

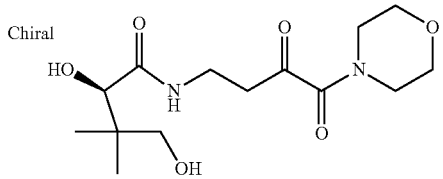 [SMILES: CC(C)(CO)[C@@H](O)C(=O)NCCC(=O)C(=O)N1CCOCC1]

(R)-2,4-Dihydroxy-3,3-dimethyl-N-(4-morpholin-4-yl-3,4-dioxo-butyl)-butyramide was synthesized following the general procedure B starting from (R)-2-(4-methoxy-phenyl)-5,5-di methyl-[1,3]dioxane-4-carboxylic acid (3-hydroxy-4-morpholin-4-yl-4-oxo-butyl)-amide (116 mg, 0.26 mmol) as an off-white solid (59 mg, 70%).

HPLC (Method B): Rt 2.91 min (Purity 98.15%). LCMS (Method B): 317.3 (M+H). $^1$H NMR (400 MHz, DMSO-$d_6$): δ 7.79 (t, J=4.5 Hz, 1H), 5.37 (d, J=5.5 Hz, 1H), 4.45 (t, J=5.6 Hz, 1H), 3.68 (d, J=5.5 Hz, 1H), 3.59-3.53 (m, 4H), 3.48-3.26 (m, 7H), 3.28-3.17 (m, 1H), 2.93 (t, J=6.6 Hz, 2H), 0.77 (s, 3H), 0.75 (s, 3H).

Example 50

(R)-2,4-Dihydroxy-N-(3-[4-(2-methoxy-ethoxy)-benzylcarbamoyl]-3-oxo-propyl)-3,3-dimethyl-butyramide

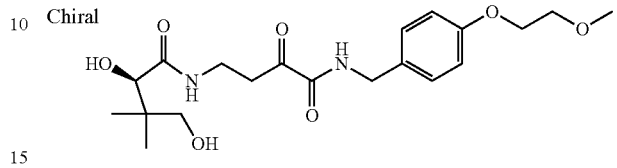

(R)-2,4-Dihydroxy-N-{3-[4-(2-methoxy-ethoxy)-benzylcarbamoyl]-3-oxo-propyl}-3,3-dimethyl-butyramide was synthesized following the general procedure B starting from (R)-2-(4-methoxy-phenyl)-5,5-dimethyl-[1,3]dioxane-4-carboxylic acid {3-hydroxy-3-[4-(2-methoxy-ethoxy)-benzylcarbamoyl]-propyl}-amide (67 mg, 0.13 mmol) as a white solid (36 mg, 69%).

HPLC (Method B): Rt 3.93 min (Purity 93.74%). LCMS (Method B): 411.0 (M+H). $^1$H NMR (400 MHz, DMSO-$d_6$): δ 9.15-9.13 (m, 1H), 7.75 (t, J=4.0 Hz, 1H), 7.17 (d, J=8.6 Hz, 2H), 6.85 (d, J=6.6 Hz, 2H), 5.34 (d, J=5.6 Hz, 1H), 4.44 (t, J=5.6 Hz, 1H), 4.22 (d, J=6.3 Hz, 2H), 4.05-4.03 (m, 2H), 3.68-3.61 (m, 3H), 3.32-3.13 (m, 7H), 3.00-2.96 (m, 2H), 0.77 (s, 3H), 0.75 (s, 3H).

Example 51

(R)—N-(3-{[1-(3-Fluoro-benzenesulfonyl)-piperidin-4-ylmethyl]-carbamoyl}-3-oxo-propyl)-2,4-dihydroxy-3,3-dimethyl-butyramide

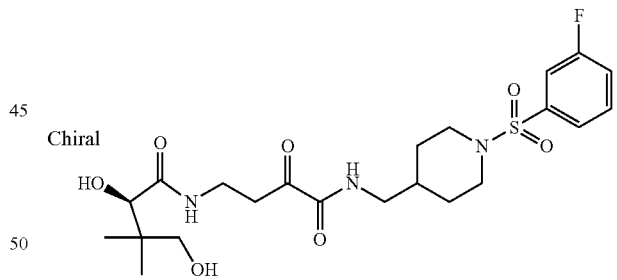

(R)—N-(3-{[1-(3-Fluoro-benzenesulfonyl)-piperidin-4-ylmethyl]-carbamoyl}-3-oxo-propyl)-2,4-dihydroxy-3,3-dimethyl-butyramide was synthesized following the general procedure B starting from (R)-2-(4-methoxy-phenyl)-5,5-dimethyl-[1,3]dioxane-4-carboxylic acid (3-{[1-(4-fluoro-benzenesulfonyl)-piperidin-4-ylmethyl]-carbamoyl}-3-hydroxy-propyl)-amide (99 mg, 0.16 mmol) as a white solid (36 mg, 45%).

HPLC (Method B): Rt 4.69 min (Purity 99.15%). LCMS (Method B): 502.0 (M+H). $^1$H NMR (400 MHz, DMSO-$d_6$): δ 8.56 (s, 1H), 7.74-7.53 (m, 5H), 5.33 (d, J=5.6 Hz, 1H), 4.45-4.44 (m, 1H), 3.67-3.59 (m, 3H), 3.32-3.12 (m, 3H), 2.97-2.93 (m, 4H), 2.32-2.22 (m, 2H), 1.65 (m, 2H), 1.45-1.42 (m, 2H), 1.19-1.05 (m, 2H), 0.76 (s, 3H), 0.75 (s, 3H).

Example 52

(R)—N-(3-{[1-(3-Fluoro-phenylmethanesulfonyl)-piperidin-4-ylmethyl]-carbamoyl}-3-oxo-propyl)-2,4-dihydroxy-3,3-dimethyl-butyramide

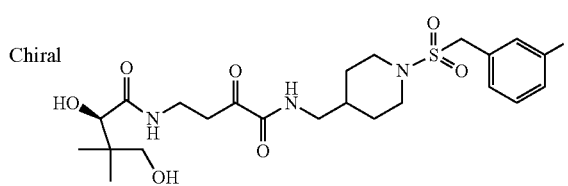

(R)—N-(3-{[1-(3-Fluoro-phenylmethanesulfonyl)-piperidin-4-ylmethyl]-carbamoyl}-3-oxo-propyl)-2,4-dihydroxy-3,3-dimethyl-butyramide was synthesized following the general procedure B starting from (R)-5,5-Dimethyl-2-phenyl-[1,3]dioxane-4-carboxylic acid (3-{[1-(3-fluoro-phenylmethanesulfonyl)-piperidin-4-ylmethyl]-carbamoyl}-3-oxo-propyl)-amide (98 mg, 0.12 mmol) as a white solid (28 mg, 44%).

HPLC (Method B): Rt 4.67 min (Purity 97.86%). LCMS (Method B): 516.0 (M+H). $^1$H NMR (400 MHz, DMSO-$d_6$): δ 8.75-8.72 (m, 1H), 7.75-7.73 (m, 1H), 7.41 (t, J=4.0 Hz, 1H), 7.25-7.19 (m, 3H), 5.34 (d, J=5.6 Hz, 1H), 4.46-4.41 (m, 3H), 3.67 (d, J=5.4 Hz, 1H), 3.52 (m, 2H), 3.32-3.14 (m, 4H), 2.99-2.94 (m, 4H), 2.66 (m, 2H), 1.63-1.62 (m, 3H), 1.05-1.03 (m, 2H), 0.78 (s, 3H), 0.77 (s, 3H).

Example 53

(R)-2,4-Dihydroxy-N-{3-[(4'-methanesulfonyl-biphenyl-4-ylmethyl)-carbamoyl]-3-oxo-propyl}-3,3-dimethyl-butyramide

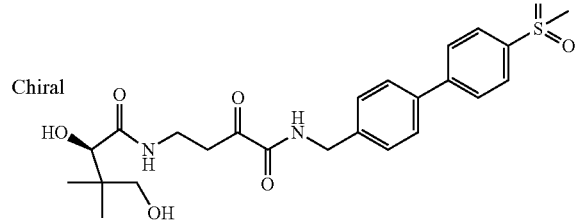

(R)-2,4-Dihydroxy-N-{3-[(4'-methanesulfonyl-biphenyl-4-ylmethyl)-carbamoyl]-3-oxo-propyl}-3,3-dimethyl-butyramide was synthesized following the general procedure B starting from (R)-2-(4-methoxy-phenyl)-5,5-dimethyl-[1,3]dioxane-4-carboxylic acid {3-hydroxy-3-(4'-methanesulfonyl-biphenyl-4-ylmethyl)-carbamoyl]-propyl}-amide (71 mg, 0.11 mmol) as an off-white solid (16 mg, 28%).

HPLC (Method B): Rt 4.31 min (Purity 98.94%). LCMS (Method B): 491.0 (M+H). $^1$H NMR (400 MHz, DMSO-$d_6$): δ 9.17 (t, J=6.4 Hz, 1H), 7.99-7.90 (m, 4H), 7.72 (t, J=8.2 Hz, 3H), 7.41 (d, J=8.2 Hz, 2H), 5.35 (d, J=5.5 Hz, 1H), 4.45 (t, J=5.6 Hz, 1H), 4.37 (d, J=6.4 Hz, 2H), 3.68 (d, J=5.4 Hz, 1H), 3.37-2.98 (m, 9H), 0.8 (s, 3H), 0.78 (s, 3H).

Example 54

4-{[4-((R)-2,4-Dihydroxy-3,3-dimethyl-butyrylamino)-2-oxo-butyrylamino]-methyl}-benzoic acid

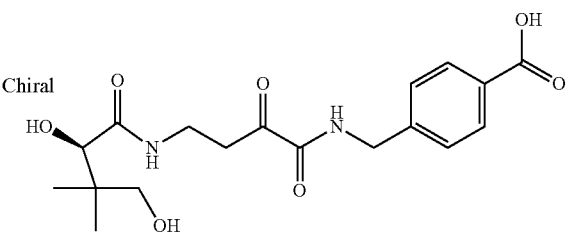 [SMILES: CC(C)(CO)[C@@H](O)C(=O)NCCC(=O)C(=O)NCc1ccc(C(=O)O)cc1]

4-{[4-((R)-2,4-Dihydroxy-3,3-dimethyl-butyrylamino)-2-oxo-butyrylamino]-methyl}-benzoic acid was synthesized following the general procedure B starting from 4-[(2-hydroxy-4-{[(R)-2-(4-methoxy-phenyl)-5,5-dimethyl-[1,3]dioxane-4-carbonyl]-amino}-butyrylamino)-methyl]-benzoic acid methyl ester followed by hydrolysis using LiOH.H$_2$O (2 eq) to afford a white solid (17 mg, 24%).

HPLC (Method B): Rt 2.16 min (Purity 94.12%). LCMS (Method B): 381.0 (M+H). $^1$H NMR (400 MHz, DMSO-$d_6$): δ 12.88 (bs, 1H), 9.17 (t, J=6.4 Hz, 1H), 7.87 (d, J=6.6 Hz, 2H), 7.78 (t, J=5.7 Hz, 1H), 7.37 (d, J=8.4 Hz, 2H), 5.35 (d, J=5.4 Hz, 1H), 4.45 (t, J=5.1 Hz, 1H), 4.37 (d, J=6.3 Hz, 2H), 3.68 (d, J=5.6 Hz, 1H), 3.37-2.97 (m, 6H), 0.8 (s, 3H), 0.78 (s, 3H).

Example 55

4'-{[4-((R)-2,4-Dihydroxy-3,3-dimethyl-butyrylamino)-2-oxo-butyrylamino]-methyl}-biphenyl-4-carboxylic acid

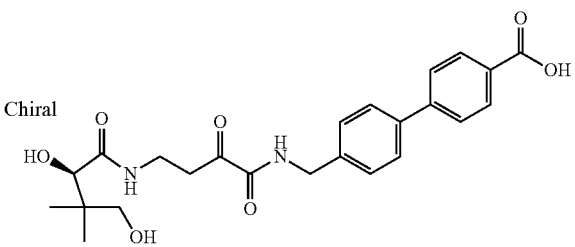 [SMILES: CC(C)(CO)[C@@H](O)C(=O)NCCC(=O)C(=O)NCc1ccc(-c2ccc(C(=O)O)cc2)cc1]

4'-{[4-((R)-2,4-Dihydroxy-3,3-dimethyl-butyrylamino)-2-oxo-butyrylamino]-methyl}-biphenyl-4-carboxylic acid was synthesized following the general procedure B starting from 4'-[(2-hydroxy-4-{[(R)-2-(4-methoxy-phenyl)-5,5-dimethyl-[1,3]dioxane-4-carbonyl]-amino}-butyrylamino)-methyl]-biphenyl-4-carboxylic acid methyl ester followed by hydrolysis using LiOH.H$_2$O (2 eq) to afford a pale yellow solid (35 mg, 50%).

HPLC (Method B): Rt 3.08 min (Purity 95.35%). LCMS (Method B): 457.0 (M+H). $^1$H NMR (400 MHz, DMSO-$d_6$): δ 13.12 (s, 1H), 9.16 (t, J=6.4 Hz, 1H), 8.00 (d, J=6.4 Hz, 2H), 7.76 (d, J=2.0 Hz, 3H), 7.67 (d, J=8.1 Hz, 2H), 7.39 (d, J=8.0 Hz, 2H), 5.34 (d, J=1.8 Hz, 1H), 4.45 (s, 1H), 4.36 (d, J=6.4 Hz, 2H), 3.68 (d, J=5.2 Hz, 1H), 3.39-3.15 (m, 6H), 0.8 (s, 3H), 0.78 (s, 3H).

Example 56

4'-{[4-((R)-2,4-Dihydroxy-3,3-dimethyl-butyrylamino)-2-oxo-butyrylamino]-methyl}-biphenyl-4-carboxylic acid methyl ester

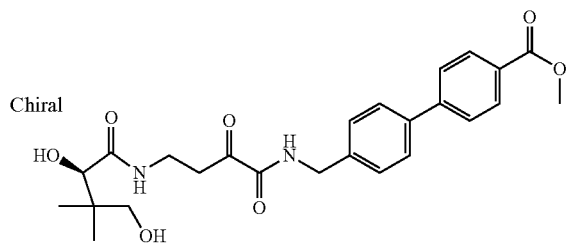 [SMILES: COC(=O)c1ccc(-c2ccc(CNC(=O)C(=O)CCNC(=O)[C@H](O)C(C)(C)CO)cc2)cc1]

4'-{[4-((R)-2,4-Dihydroxy-3,3-dimethyl-butyrylamino)-2-oxo-butyrylamino]-methyl}-biphenyl-4-carboxylic acid methyl ester was synthesized following the general procedure E starting from 4'-[(2-hydroxy-4-{[(R)-2-(4-methoxy-phenyl)-5,5-dimethyl-[1,3]dioxane-4-carbonyl]-amino}-butyrylamino)-methyl]-biphenyl-4-carboxylic acid methyl ester as a white solid (14 mg, 32%).

HPLC (Method B): Rt 5.08 min (Purity 96.85%). LCMS (Method B): 471.3 (M+H). $^1$H NMR (400 MHz, DMSO-d$_6$): δ 9.16 (t, J=4 Hz, 1H), 8.02 (d, J=6.8 Hz, 2H), 7.79 (d, J=6.0 Hz, 3H), 7.68 (d, J=8.4 Hz, 2H), 7.39 (d, J=8.4 Hz, 2H), 5.35 (d, J=5.6 Hz, 1H), 4.45 (t, J=5.6 Hz, 1H), 4.36 (d, J=6.4 Hz, 2H), 3.86 (s, 3H), 3.68 (d, J=5.3 Hz, 1H), 3.37-3.13 (m, 3H), 3.02-2.98 (m, 3H), 0.8 (s, 3H), 0.78 (s, 3H).

Example 57

(R)—N-[2-(2-Chloro-acetylamino)-ethyl]-2,4-dihydroxy-3,3-dimethyl-butyramide

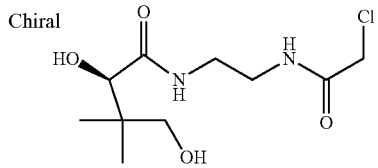 [SMILES: CC(C)(CO)[C@@H](O)C(=O)NCCNC(=O)CCl]

(R)—N-[2-(2-Chloro-acetylamino)-ethyl]-2,4-dihydroxy-3,3-dimethyl-butyramide was synthesized following the general procedure H starting from (R)—N-(2-amino-ethyl)-2,4-dihydroxy-3,3-dimethyl-butyramide (148 mg, 0.72 mmol) as a colorless gum (147 mg, 76%).

HPLC (Method A ELSD): Rt 1.35 min (Purity 99.62%). LCMS (Method A): 267.3 (M+H). $^1$H NMR (400 MHz, DMSO-d$_6$): δ 8.20 (s, 1H), 7.81 (d, J=5.4 Hz, 1H), 5.36 (d, J=5.5 Hz, 1H), 4.46 (t, J=5.6 Hz, 1H), 4.03 (s, 2H), 3.70 (d, J=5.4 Hz, 1H), 3.32-3.19 (m, 5H), 0.8 (s, 3H), 0.78 (s, 3H).

Example 58

(R)—N-{2-[(2-Chloro-acetyl)-(3-phenyl-propyl)-amino]-ethyl}-2,4-dihydroxy-3,3-dimethyl-butyramide

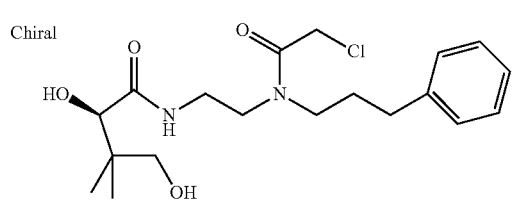 [SMILES: CC(C)(CO)[C@@H](O)C(=O)NCCN(CCCc1ccccc1)C(=O)CCl]

(R)—N-{2-[(2-Chloro-acetyl)-(3-phenyl-propyl)-amino]-ethyl}-2,4-dihydroxy-3,3-dimethyl-butyramide was synthesized following the general procedure H starting from (R)-2,4-dihydroxy-3,3-dimethyl-N-[2-(3-phenyl-propylamino)-ethyl]-butyramide (34 mg, 0.11 mmol) as a colorless gum (13 mg, 30%).

HPLC (Method A ELSD): Rt 3.57 min (Purity 98.28%). LCMS (Method A): 385.3 (M+H). $^1$H NMR (400 MHz, DMSO-d$_6$): δ 7.93 (s, 1H), 7.28-7.16 (m, 5H), 5.47 (d, J=5.4 Hz, 2H), 4.46 (s, 1H), 4.36 (s, 2H), 3.72-3.71 (m, 3H), 3.32-3.14 (m, 4H), 2.55-2.44 (m, 2H), 1.82-1.75 (m, 3H), 0.8 (s, 3H), 0.78 (s, 3H).

Example 59

(R)—N-{2-[(2-Chloro-acetyl)-phenethyl-amino]-ethyl}-2,4-dihydroxy-3,3-dimethyl-butyramide

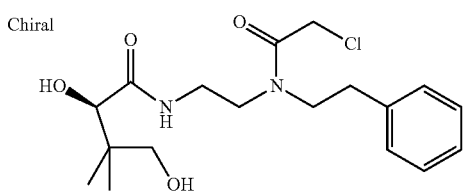 [SMILES: CC(C)(CO)[C@@H](O)C(=O)NCCN(CCc1ccccc1)C(=O)CCl]

(R)—N-{2-[(2-Chloro-acetyl)-phenethyl-amino]-ethyl}-2,4-dihydroxy-3,3-dimethyl-butyramide was synthesized following the general procedure H starting from (R)-2,4-dihydroxy-3,3-dimethyl-N-(2-phenethylamino-ethyl)-butyramide (162 mg, 0.55 mmol) as an off white gum (34 mg, 36%).

HPLC (Method A): Rt 3.24 min (Purity 99.49%). LCMS (Method A): 371.2 (M+H). $^1$H NMR (400 MHz, DMSO-d$_6$): δ 7.92-7.72 (m, 1H), 7.29-7.20 (m, 5H), 5.47-5.35 (m, 1H), 4.47-4.44 (m, 1H), 4.36 (s, 1H), 4.20 (s, 1H), 3.69 (d, J=5.1 Hz, 1H), 3.50-3.24 (m, 8H), 2.85-2.75 (m, 2H), 0.80 (s, 3H), 0.78 (s, 3H).

Example 60

(R)—N-{2-[Benzyl-(2-chloro-acetyl)-amino]-ethyl}-2,4-dihydroxy-3,3-dimethyl-butyramide

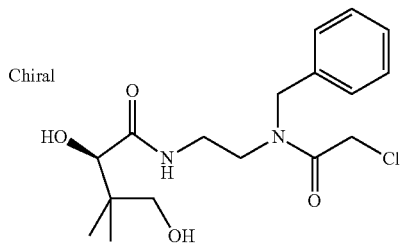 [SMILES: CC(C)(CO)[C@@H](O)C(=O)NCCN(Cc1ccccc1)C(=O)CCl]

(R)—N-{2-[Benzyl-(2-chloro-acetyl)-amino]-ethyl}-2,4-dihydroxy-3,3-dimethyl-butyramide was synthesized following the general procedure H starting from (R)—N-(2-benzylamino-ethyl)-2,4-dihydroxy-3,3-dimethyl-butyramide (77 mg, 0.26 mmol) as a colorless gum (71 mg, 76%).

HPLC (Method A): Rt 3.10 min (Purity 99.75%). LCMS (Method A): 357.2 (M+H). $^1$H NMR (400 MHz, DMSO-$d_6$): δ 7.94 (s, 1H), 7.39-7.20 (m, 5H), 5.47 (s, 1H), 4.61-4.37 (m, 5H), 3.72-3.68 (m, 1H), 3.32-3.13 (m, 6H), 0.80 (s, 3H), 0.78 (s, 3H).

Example 61

(R)—N-(2-{(2-Chloro-acetyl)-[2-(4-cyano-phenoxy)-ethyl]-amino}-ethyl)-2,4-dihydroxy-3,3-dimethyl-butyramide

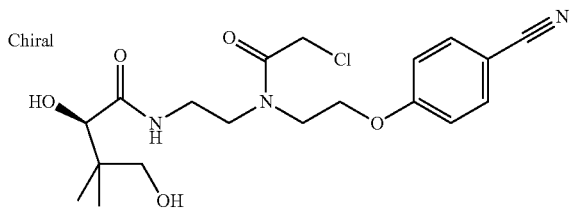 [SMILES: CC(C)(CO)[C@@H](O)C(=O)NCCN(CCOc1ccc(C#N)cc1)C(=O)CCl]

(R)—N-(2-{(2-Chloro-acetyl)-[2-(4-cyano-phenoxy)-ethyl]-amino}-ethyl)-2,4-dihydroxy-3,3-dimethyl-butyramide was synthesized following the general procedure H starting from (R)—N-{2-[2-(4-cyano-phenoxy)-ethyl-amino]-ethyl}-2,4-dihydroxy-3,3-dimethyl-butyramide (332 mg, 0.99 mmol) as an off-white solid (98 mg, 24%).

HPLC (Method A): Rt 3.05 min (Purity 99.75%). LCMS (Method A): 412.3 (M+H). $^1$H NMR (400 MHz, DMSO-$d_6$): δ 7.79-7.75 (m, 3H), 7.12 (d, J=8.8 Hz, 2H), 5.49-5.34 (m, 1H), 4.48-4.42 (m, 3H), 4.25-4.16 (m, 2H), 3.76-3.64 (m, 3H), 3.44-3.24 (m, 6H), 0.80 (s, 3H), 0.78 (s, 3H).

Example 62

(R)—N-(2-{(2-Chloro-acetyl)-[1-(4-cyano-phenyl)-piperidin-4-ylmethyl]-amino}-ethyl)-2,4-dihydroxy-3,3-dimethyl-butyramide

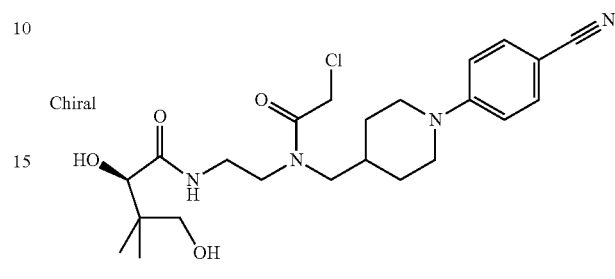

(R)—N-(2-{(2-Chloro-acetyl)-[1-(4-cyano-phenyl)-piperidin-4-ylmethyl]-amino}-ethyl)-2,4-dihydroxy-3,3-dimethyl-butyramide was synthesized following the general procedure H starting from (R)—N-(2-{[1-(4-cyano-phenyl)-piperidin-4-ylmethyl]-amino}-ethyl)-2,4-dihydroxy-3,3-dimethyl-butyramide (25 mg, 0.06 mmol) as an off-white solid (10 mg, 33%).

HPLC (Method A): Rt 3.38 min (Purity 90.54%). LCMS (Method A): 465.2 (M+H). $^1$H NMR (400 MHz, DMSO-$d_6$): δ 7.92 (s, 1H), 7.53 (d, J=9.0 Hz, 2H), 6.99 (d, J=8.8 Hz, 2H), 5.46 (s, 1H), 4.48-4.35 (m, 4H), 3.94-3.90 (m, 3H), 3.71 (t, J=4.3 Hz, 1H), 3.25-3.23 (m, 4H), 2.86-2.75 (m, 3H), 1.91 (bs, 1H), 1.60-1.58 (m, 2H), 1.23-1.12 (m, 3H), 0.80 (s, 3H), 0.78 (s, 3H).

Example 63

(R)—N-{2-[(2-Chloro-acetyl)-(2-phenoxy-ethyl)-amino]-ethyl}-2,4-dihydroxy-3,3-dimethyl-butyramide

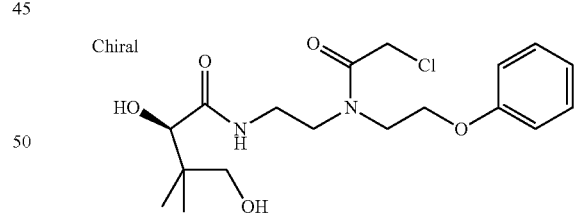

(R)—N-{2-[(2-Chloro-acetyl)-(2-phenoxy-ethyl)-amino]-ethyl}-2,4-dihydroxy-3,3-dimethyl-butyramide was synthesized following the general procedure H starting from (R)-2,4-dihydroxy-3,3-dimethyl-N-[2-(2-phenoxy-ethyl-amino)-ethyl]-butyramide (396 mg, 1.27 mmol) as a beige gum (74 mg, 15%).

HPLC (Method A): Rt 3.29 min (Purity 98.05%). LCMS (Method A): 387.0 (M+H). $^1$H NMR (400 MHz, DMSO-$d_6$): δ 8.02-7.79 (m, 1H), 7.31-7.25 (m, 2H), 6.94-6.92 (m, 3H), 5.75-5.33 (m, 1H), 4.48-4.42 (m, 3H), 4.13-4.04 (m, 2H), 3.74-3.62 (m, 3H), 3.44-3.23 (m, 6H), 0.80 (s, 3H), 0.78 (s, 3H).

Example 64

(R)—N-(2-{(2-Chloro-acetyl)-[2-(4-methanesulfonyl-phenoxy)-ethyl]-amino}-ethyl)-2,4-dihydroxy-3,3-dimethyl-butyramide

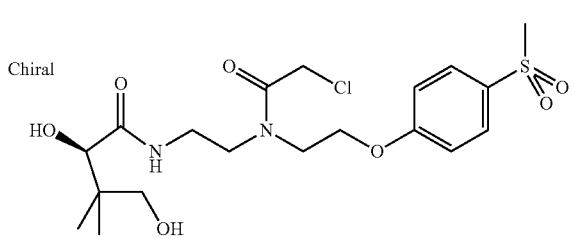 [SMILES: CC(C)(CO)[C@@H](O)C(=O)NCCN(CCOc1ccc(S(C)(=O)=O)cc1)C(=O)CCl]

(R)—N-(2-{(2-Chloro-acetyl)-[2-(4-methanesulfonyl-phenoxy)-ethyl]-amino}-ethyl)-2,4-dihydroxy-3,3-dimethyl-butyramide was synthesized following the general procedure H starting from (R)-2,4-dihydroxy-N-{2-[2-(4-methanesulfonyl-phenoxy)-ethylamino]-ethyl}-3,3-dimethyl-butyramide (38 mg, 0.11 mmol) as a brown gum (20 mg, 44%).

HPLC (Method B): Rt 3.81 min (Purity 95.91%). LCMS (Method A): 465.0 (M+H¹H NMR (400 MHz, DMSO-d$_6$): δ 7.97 (s, J=4.0 Hz 1H), 7.85 (d, J=8.8 Hz, 2H), 7.17 (d, J=8.8 Hz, 2H), 5.50-5.35 (m, 2H), 4.49-4.42 (m, 3H), 4.26-4.12 (m, 3H), 3.77-3.66 (m, 4H), 3.32-3.30 (m, 3H), 3.14 (s, 3H), 0.80 (s, 3H), 0.78 (s, 3H).

Example 65

4-(2-{(2-Chloro-acetyl)-[2-((R)-2,4-dihydroxy-3,3-dimethyl-butyrylamino)-ethyl]-amino}-ethoxy)-benzoic acid methyl ester

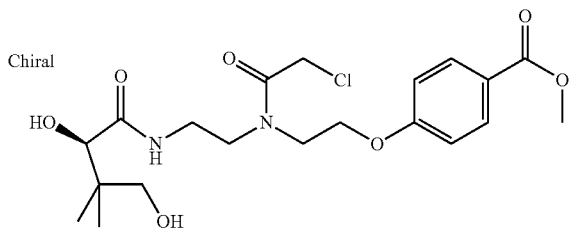 [SMILES: COC(=O)c1ccc(OCCN(CCNC(=O)[C@H](O)C(C)(C)CO)C(=O)CCl)cc1]

4-(2-{(2-Chloro-acetyl)-[2-((R)-2,4-di hydroxy-3,3-dimethyl-butyrylamino)-ethyl]-amino}-ethoxy)-benzoic acid methyl ester was synthesized following the general procedure H starting from 4-{2-[2-((R)-2,4-dihydroxy-3,3-dimethyl-butyrylamino)-ethylamino]-ethoxy}-benzoic acid methyl ester (33 mg, 0.09 mmol) as a yellow gum (4 mg, 10%).

HPLC (Method A): Rt 3.21 min (Purity 96.01%). LCMS (Method A): 445.0 (M+H). ¹H NMR (400 MHz, DMSO-d$_6$): δ 7.92-7.88 (m, 3H), 6.52 (d, J=8.0 Hz, 2H), 5.49-5.35 (m, 1H), 4.48-4.46 (m, 3H), 4.42-4.25 (m, 4H), 3.80 (s, 3H), 3.76-3.66 (m, 3H), 3.43-3.18 (m, 4H), 0.80 (s, 3H), 0.78 (s, 3H).

Example 66

(R)—N-{2-[[(2-(4-Bromo-phenoxy)-ethyl]-(2-chloro-acetyl)-amino]-ethyl}-2,4-dihydroxy-3,3-dimethyl-butyramide

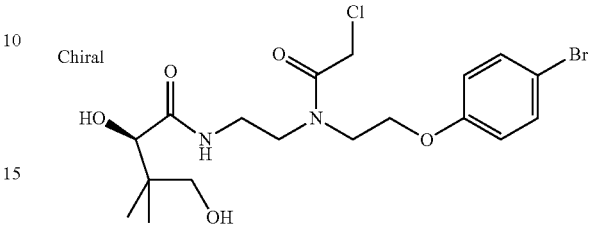

(R)—N-{2-[[2-(4-Bromo-phenoxy)-ethyl]-(2-chloro-acetyl)-amino]-ethyl}-2,4-dihydroxy-3,3-dimethyl-butyramide was synthesized following the general procedure H starting from (R)—N-{2-[2-(4-bromo-phenoxy)-ethylamino]-ethyl}-2,4-dihydroxy-3,3-dimethyl-butyramide (577 mg, 1.55 mmol) as a yellow gum (190 mg, 18%).

HPLC (Method A): Rt 3.86 min (Purity 98.1%). LCMS (Method A): 465.0 (M+H). ¹H NMR (400 MHz, DMSO-d$_6$): 7.95 (t, J=4.0 Hz, 1H), 7.46-7.42 (m, 2H), 6.93-6.91 (m, 2H), 5.49-5.34 (m, 1H), 4.47-4.42 (m, 4H), 4.13-4.05 (m, 2H), 3.73-3.63 (m, 3H), 3.42-3.18 (m, 5H), 0.8 (s, 3H), 0.78 (s, 3H).

Vanin-1 Enzymatic Assay:

Human recombinant Vanin-1 (VNN1) was purchased from Sino Biological Inc. (Catalog Number: 11662-H08H).

Measurement of VNN1 inhibition is performed in 384-well format based on fluorescence intensity assay. Purified recombinant human Vanin-1 (0.5 nM) and threefold serial diluted compounds in 3% DMSO (range of concentrations from 30 μM to 1.524 nM) or controls (3.0% DMSO) are incubated for 30 minutes at 30° C. with gentle agitation in assay buffer containing 100 mM potassium Phosphate Buffer (KPi), pH 7.5, 0.001% Bovine Serum Albumin (BSA), 0.5 mM dithiothreitol (DTT) and 0.0025% Brij-35. The reaction is initiated by the addition of the fluorogenic substrate, Pantothenate-AMC, at a concentration of 30 μM. After 60 minutes of incubation at 30° C. with gentle agitation, fluorescence intensity is measured at $\lambda_{ex}$=350 nm and $\lambda_{em}$=450 nm with a fluorescence reader (BMG PHERAstar reader or equivalent).

Vanin-1 Cell-Based Mechanistic Assay:

The cellular activity of the examples is measured in 96-well format based on fluorescence intensity assay using SUIT-S2 cell line (ATCC # CRL1596).

Cells are cultured at 37° C. with 5% CO$_2$ to 80-90% confluence and then washed once with phosphate-buffered saline (PBS). Adherent cells are detached with PBS-EDTA and once in suspension 40000 cells are dispensed in 90 μl of PBS in 96-well black plates with clear bottoms. Threefold serial dilutions of test compounds are made in DMSO and then solubilized in PBS, dilution range 1:30. Cells and serial diluted test compounds (final concentrations 10 μM to 4.6 nM) or controls (PBS/0.3% DMSO) are incubated for 2 hours at 37° C. with 5% CO$_2$. The reaction is initiated by the addition of the fluorogenic substrate, Pantothenate-AMC, at a concentration of 30 μM. After 30 minutes of incubation at 30° C. with gentle agitation, fluorescence intensity is measured at $\lambda_{ex}$=350 nm and $\lambda_{em}$=450 nm with a fluorescence reader (BMG PHERAstar reader or equivalent).

The invention claimed is:
1. A compound of formula (I):
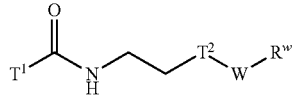
wherein:
T¹ denotes one of the following groups:
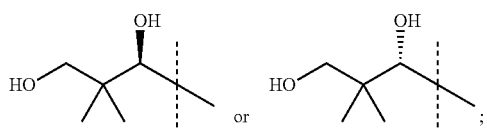
T²-W denotes one of the following groups:
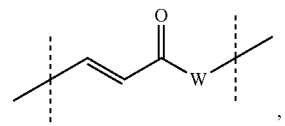
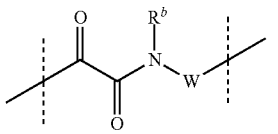
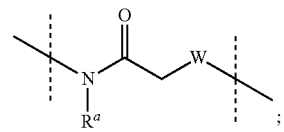
W denotes a single bond, or a group selected from —CHR$^c$— and —CH=CH—;
R$^w$ denotes H, Hal, linear or branched alkyl, or one of the following groups:
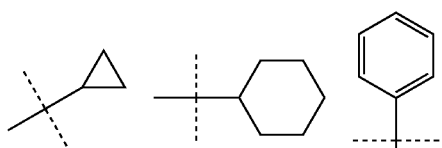
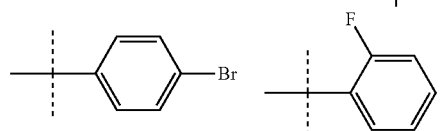
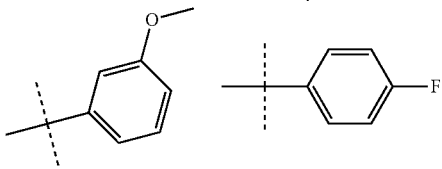
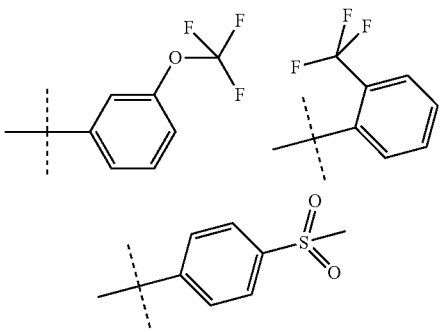
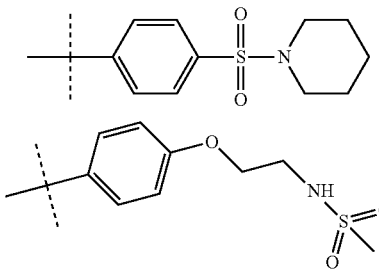
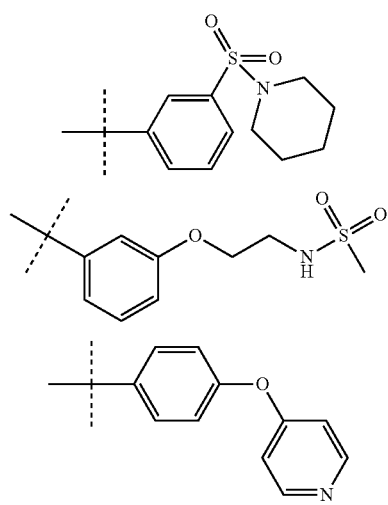
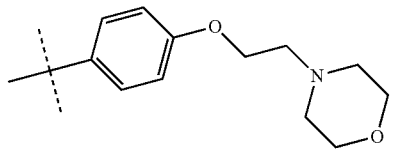
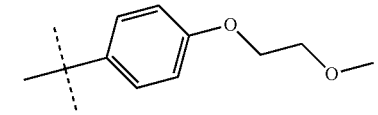
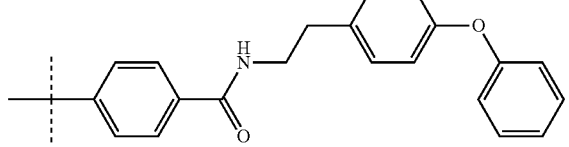
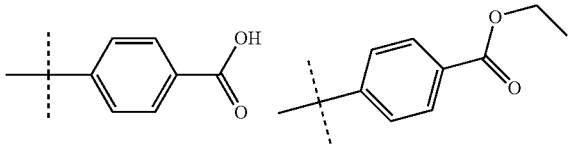

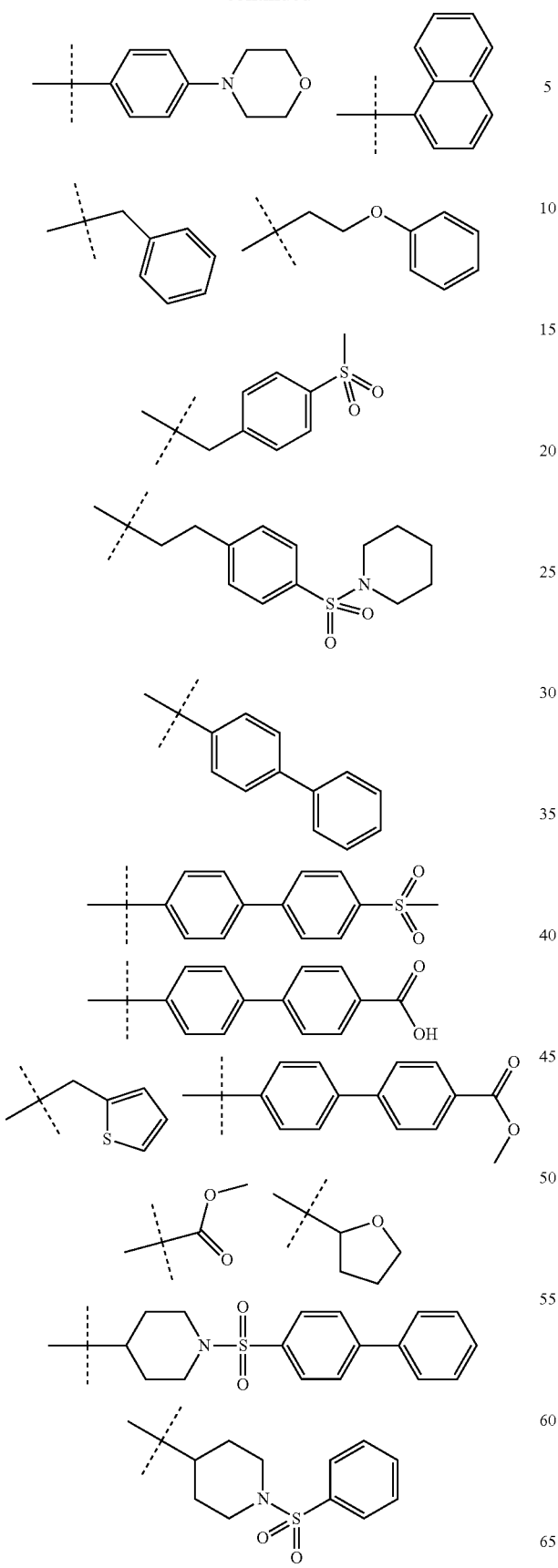
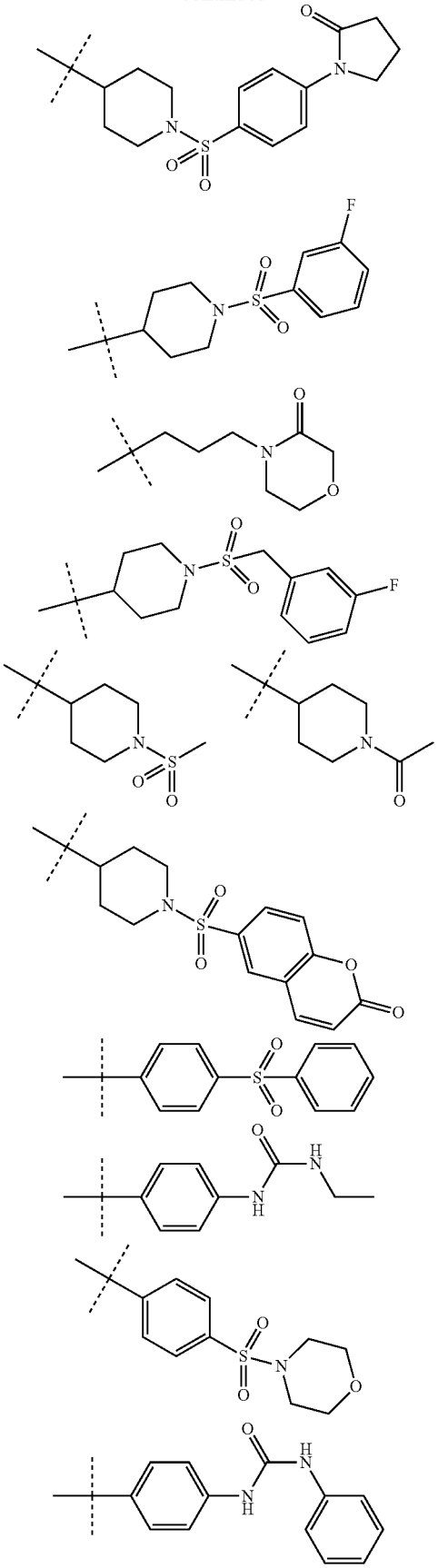

-continued

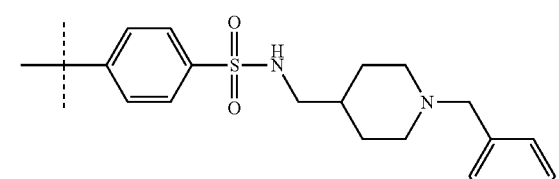
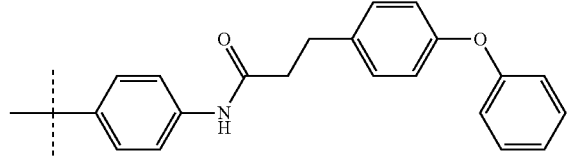
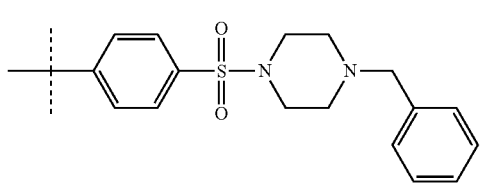
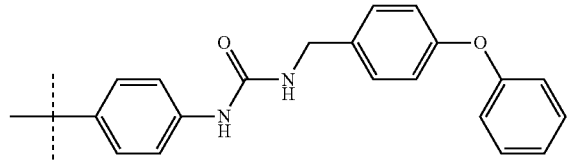
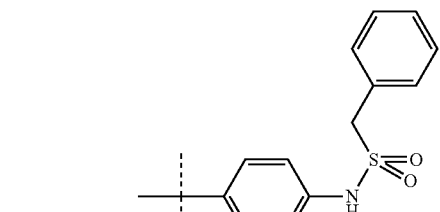
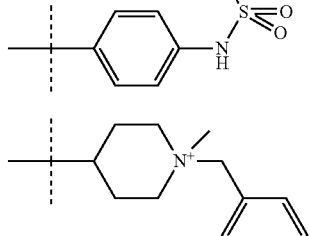
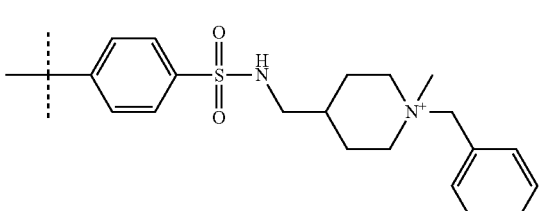

or

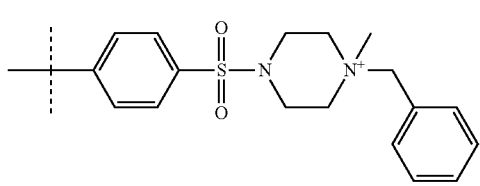

or wherein $R^b$ and $R^w$ together with the nitrogen atom to which they are linked form one of the following groups:

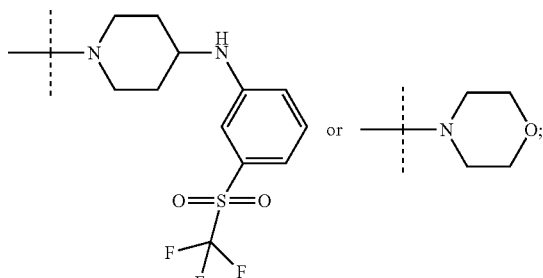

$R^b$ denotes H or a linear or branched alkyl, or alternatively, $R^b$ and $R^w$ together with the nitrogen atom to which they are linked form a Het group;

$R^c$ denotes H, Ar, or alkyl;

$R^a$ denotes H and a group selected from the following groups:

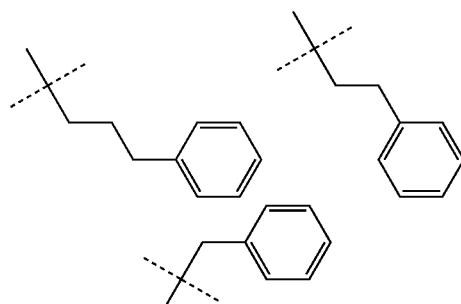
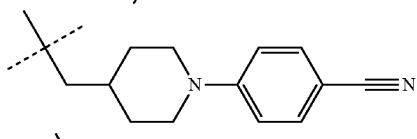
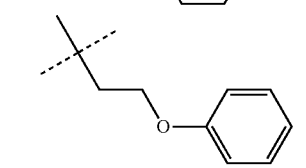
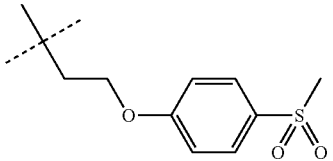
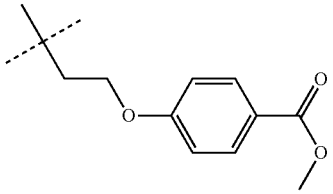

-continued

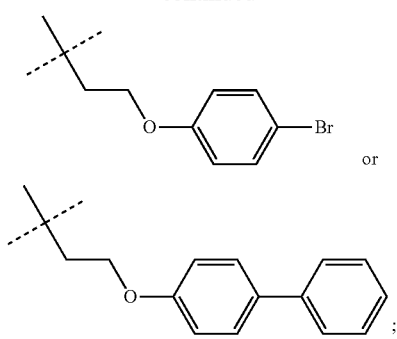

Ar denotes one of the following groups

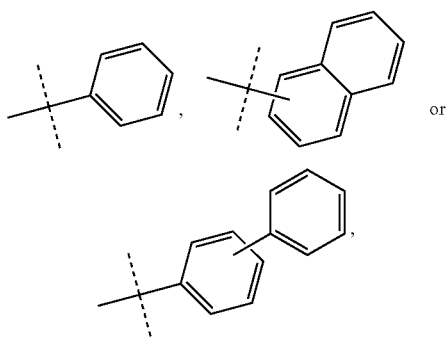

optionally substituted with from 1 to 5 groups independently selected from Hal, CN, —CF$_3$, —OCF$_3$, O-alkyl, SO$_2$-alkyl, COOR$^b$, —CO-alkyl, O-phenyl, SO$_2$-phenyl, SO$_2$—Het, O-Het, Het, —(CH$_2$)$_n$—Het, SO$_2$—CF$_3$, O—(CH$_2$)$_n$-Het, O—(CH$_2$)$_n$-alkyl, and A;

Het denotes a monocyclic 5-8-membered ring being saturated, unsaturated or aromatic, containing 1 to 3 heteroatoms independently selected from N, O and S, or a group CO, and optionally substituted with from 1 to 5 groups independently selected from Hal, CN, —CF$_3$, —OCF$_3$, O-alkyl, SO$_2$-alkyl, COOR$^b$, —CO-alkyl, O-phenyl, SO$_2$-phenyl, SO$_2$—CF$_3$, O—(CH$_2$)$_n$-alkyl, SO$_2$Ar, Ar, and A;

A is branched or linear alkyl having 1 to 12 C-atoms, wherein one or more H atoms may be replaced by Ar, Het, Hal, OR$^b$, COOR$^b$, CN or N(R$^b$)$_2$ and wherein one or more CH$_2$-groups may be replaced by O, CO, NR$^b$, S, SO, SO$_2$, phenyl, —CH=CH— or —C≡C— and/or by one of the following groups:

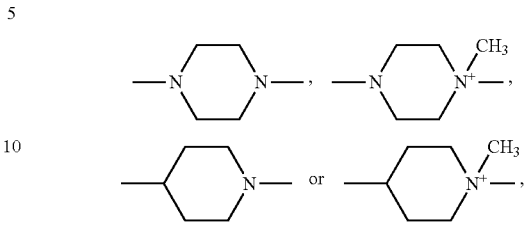

having Hal or mesylate as counter ion;
Hal denotes F, Cl, Br, or I;
n is 1, 2 or 3;
and pharmaceutically usable solvates, salts and stereoisomers thereof, including mixtures thereof in all ratios.

2. A kit consisting of separate packs of:
(a) an effective amount of a compound according to claim 1 and/or pharmaceutically usable solvates, salts, hydrates and stereoisomers thereof, including mixtures thereof in all ratios, and
(b) an effective amount of a further medicament active ingredient.

3. A pharmaceutical composition comprising a compound according to claim 1.

4. A method of treating an inflammatory disease comprising administering a compound according to claim 1 to an individual having an inflammatory disease.

5. The method according claim 4, wherein the inflammatory disease is inflammatory bowel disease.

6. The method according to claim 4, wherein the inflammatory bowel disease is ulcerative colitis.

7. The method according to claim 4, wherein the inflammatory disease is selected from the group consisting of rheumatoid arthritis, juvenile rheumatoid arthritis, psoriatic arthritis, systemic lupus erythematosus, lupus nephritis, ankylosing spondylitis, psoriasis, amyloidosis, systemic sclerosis, sarcoidosis, osteoarthritis, osteoporosis/bone resorption, septic shock, atherosclerosis, ischemia-reperfusion injury, coronary heart disease, vasculitis, multiple sclerosis, sepsis, uveitis, endometriosis, Behcet's disease, Wegener's granulomatosis, idiopathic thrombocytopenic purpura, immune deficiencies, chronic graft-versus-host disease, transplant rejection, adult respiratory distress syndrome, pulmonary fibrosis, chronic obstructive pulmonary disease, cancer, lymphoproliferative disease, myeloproliferative disorder, diabetes, meningitis, skin delayed type hypersensitivity disorders, and allergic asthma.

8. A compound selected from:

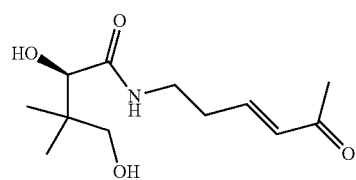

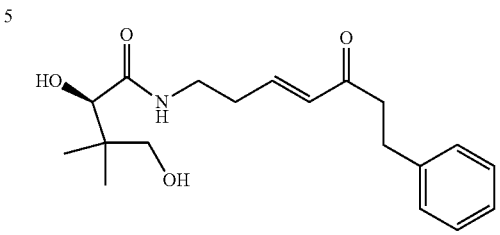

127
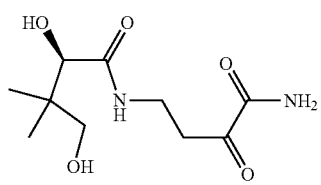
1
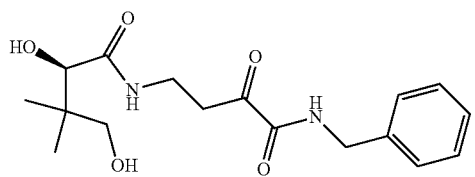
3
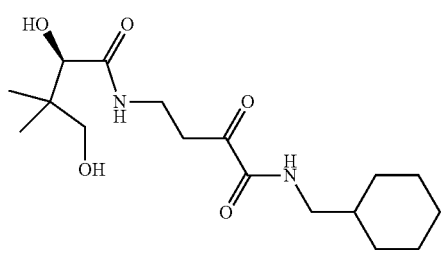
5
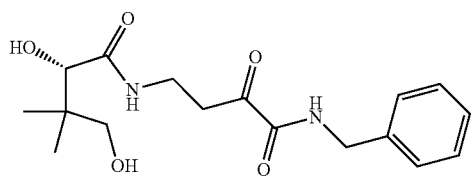
13
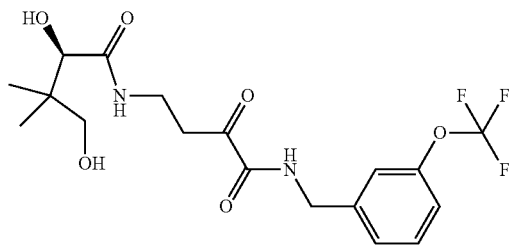
15
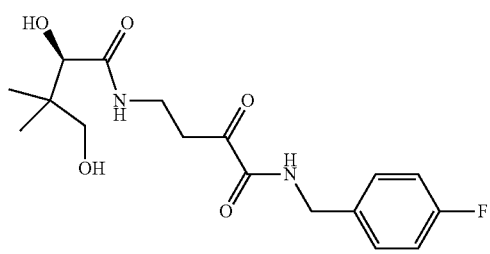
17
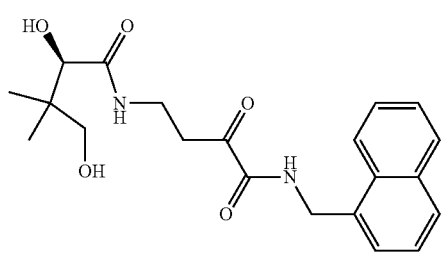
19
128
-continued
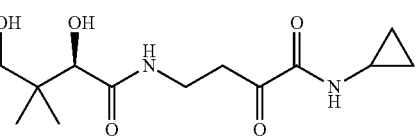
7
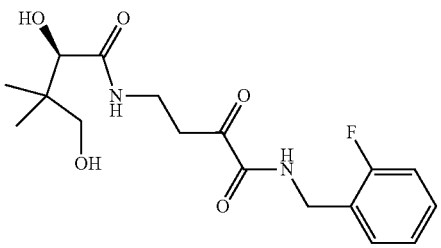
9
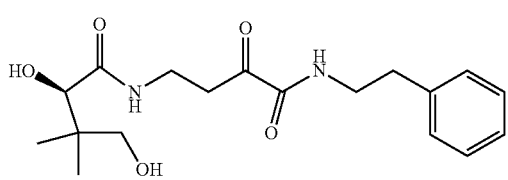
11
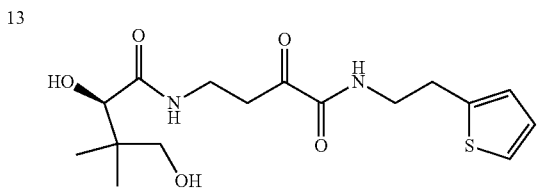
13
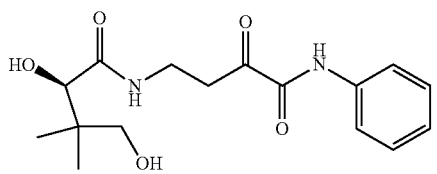
15
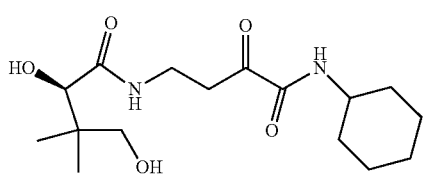
17
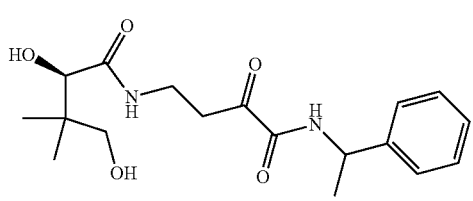
19
8
10
12
14
16
18
20

-continued
21
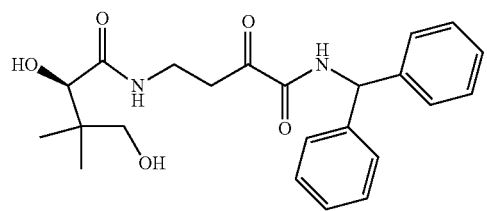
22
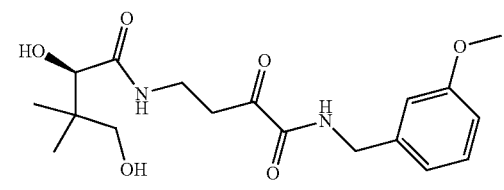
23
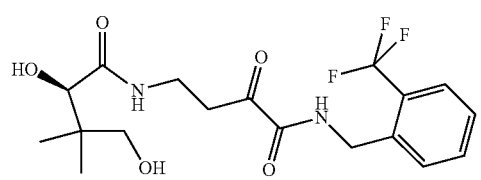
24
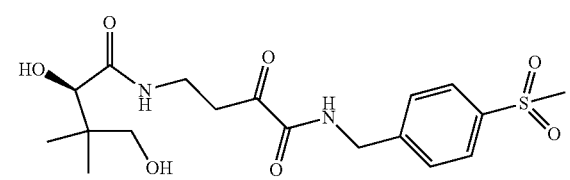
25
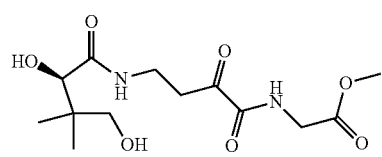
26
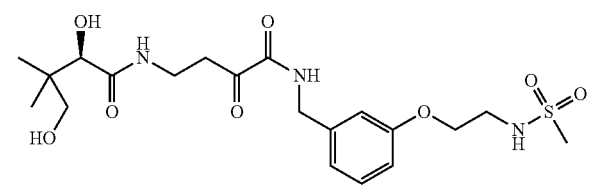
27
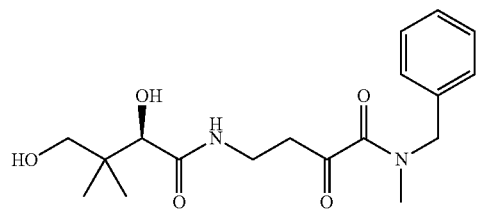
28
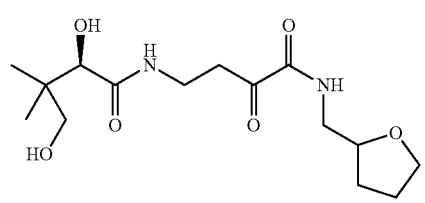
29
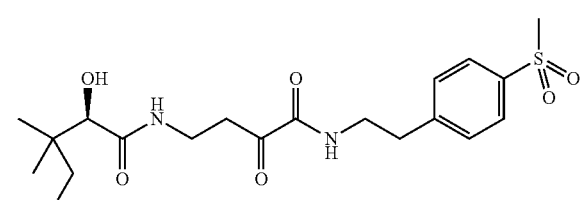
30
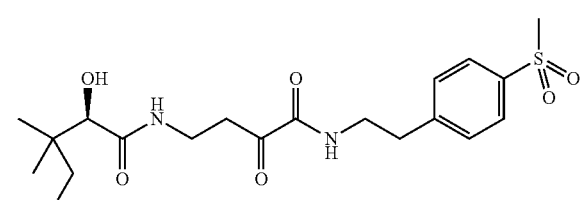
31
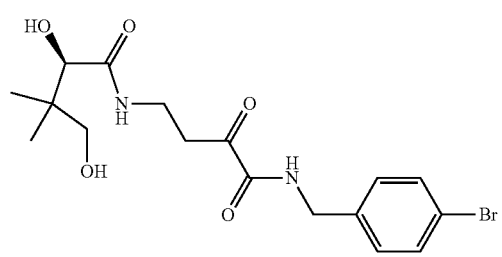
32
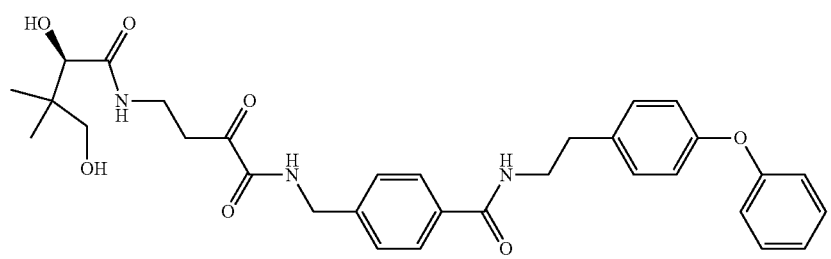

-continued
33
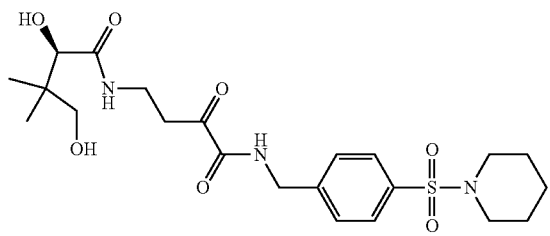
34
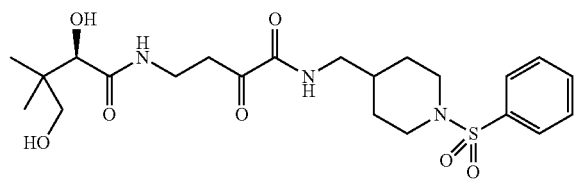
35
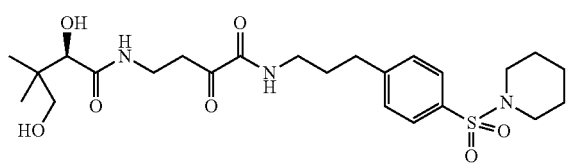
36
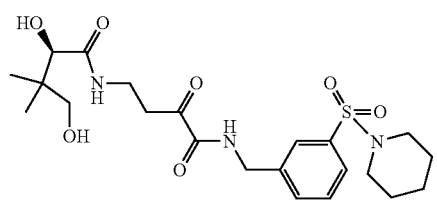
37
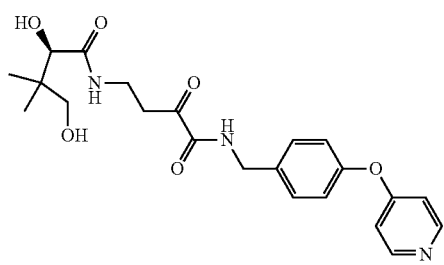
38
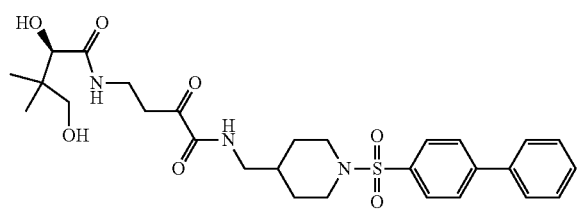
39
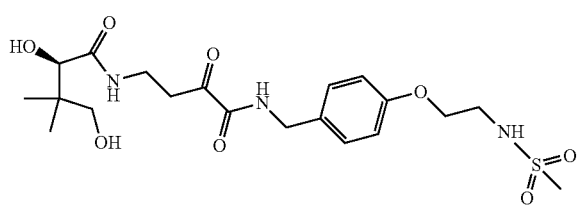
40
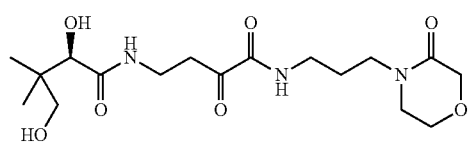
41
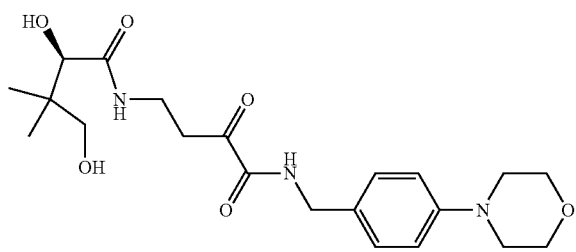
42
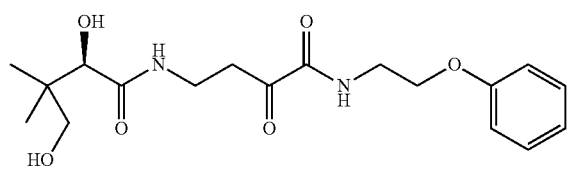
43
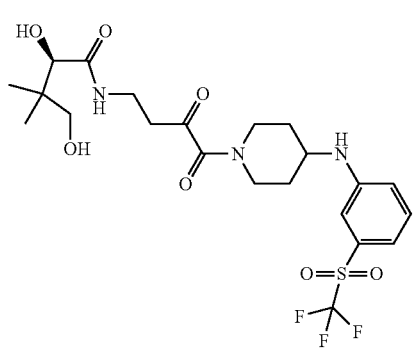
44
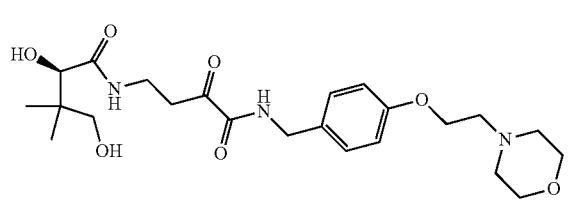

-continued
45
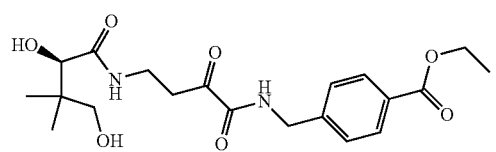
46
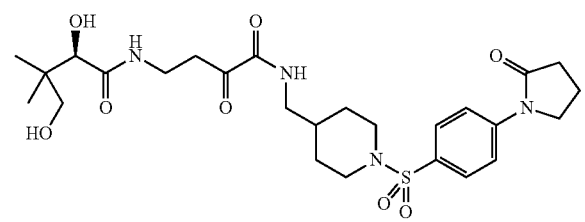
47
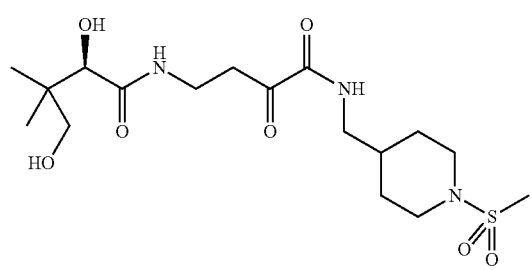
48
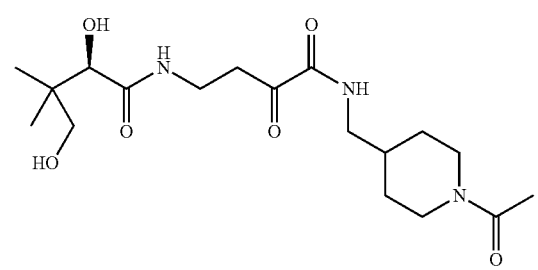
49
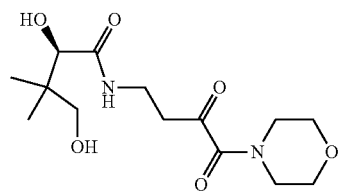
50
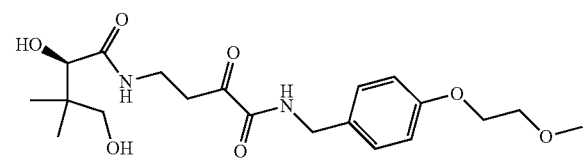
51
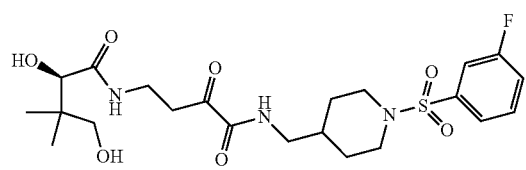
52
53
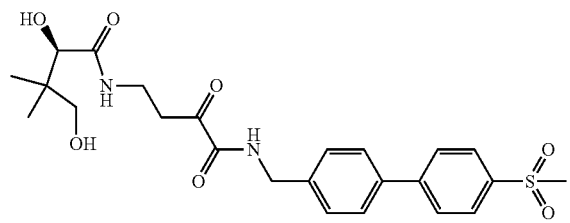
54
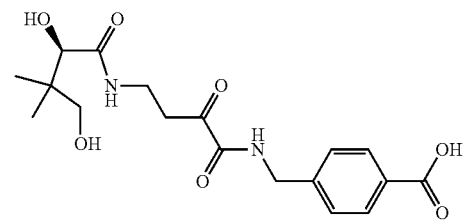
55
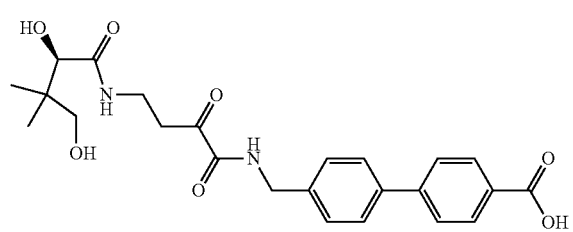
56
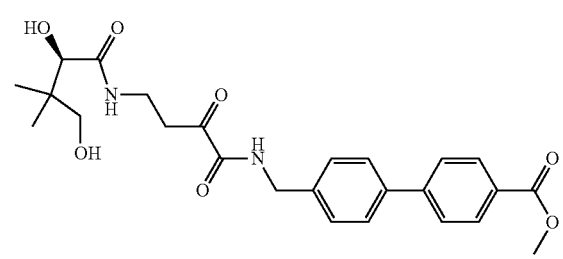
57
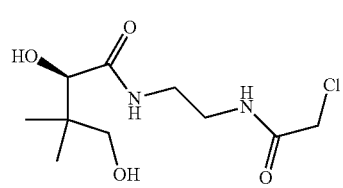
58
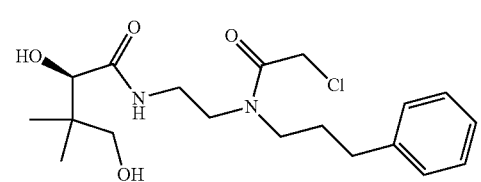

-continued
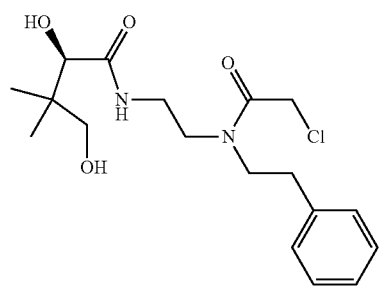
59
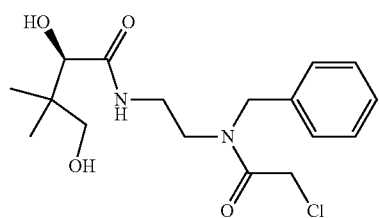
60
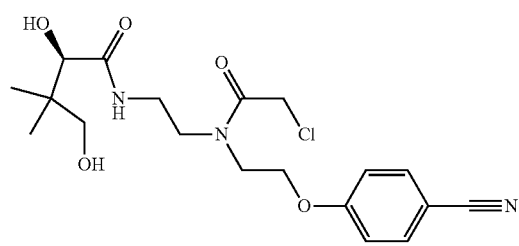
61
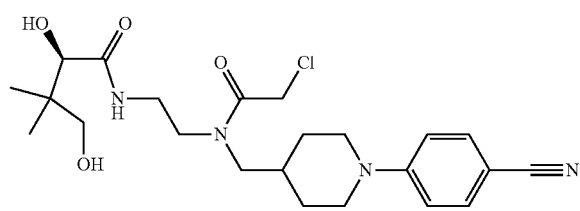
62
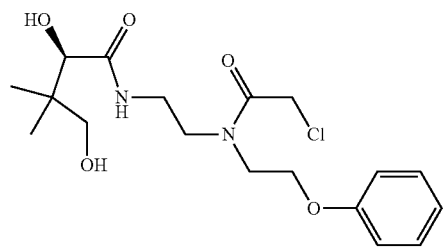
63
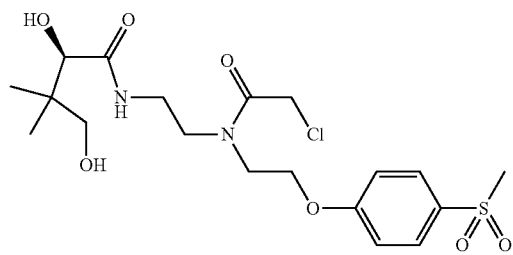
64
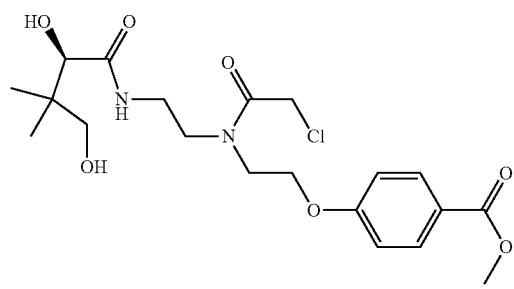
65
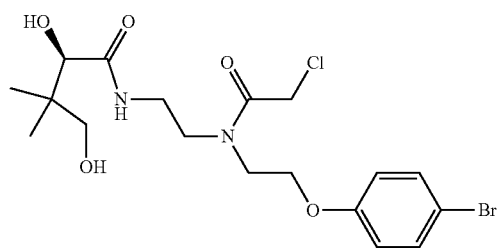
66
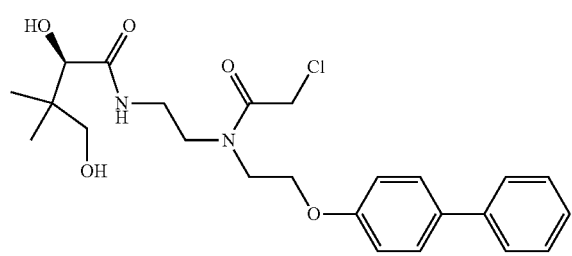
67
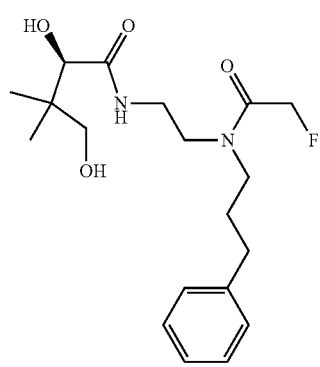
68

69
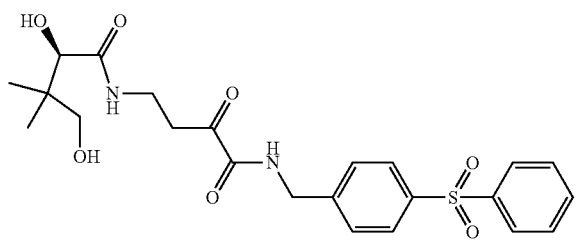
70
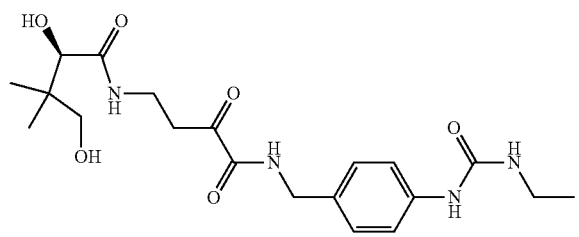
71
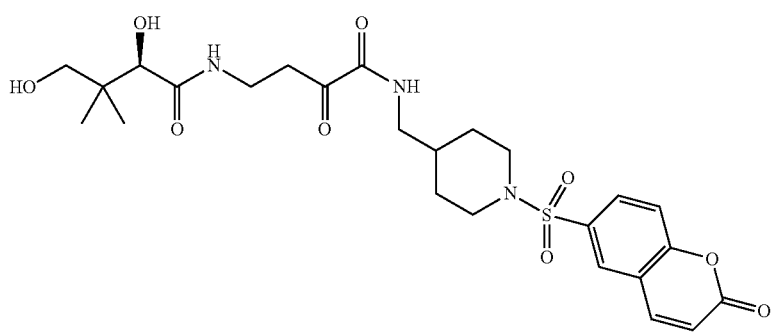
72
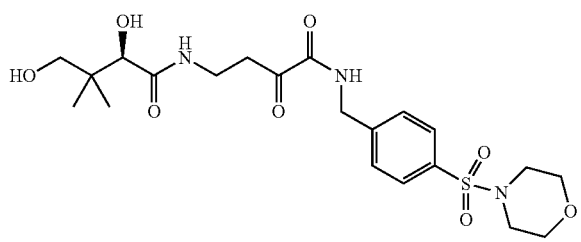
73
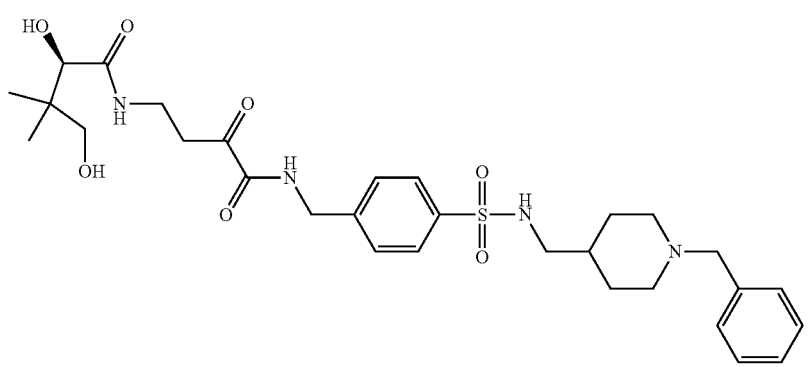
74
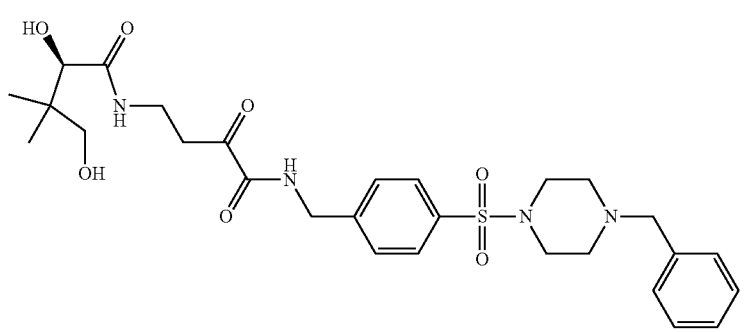
75

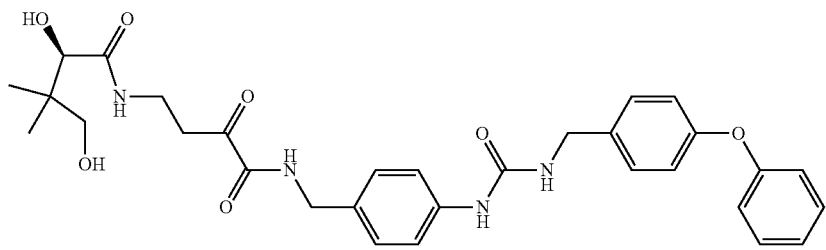
76
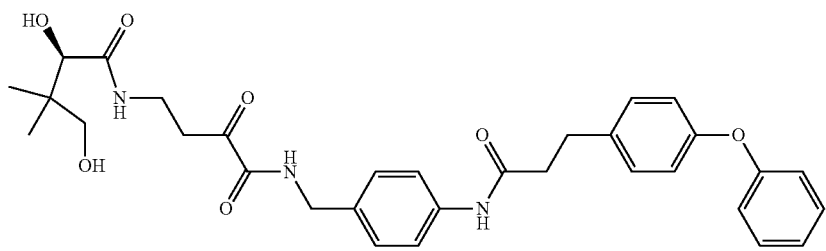
77
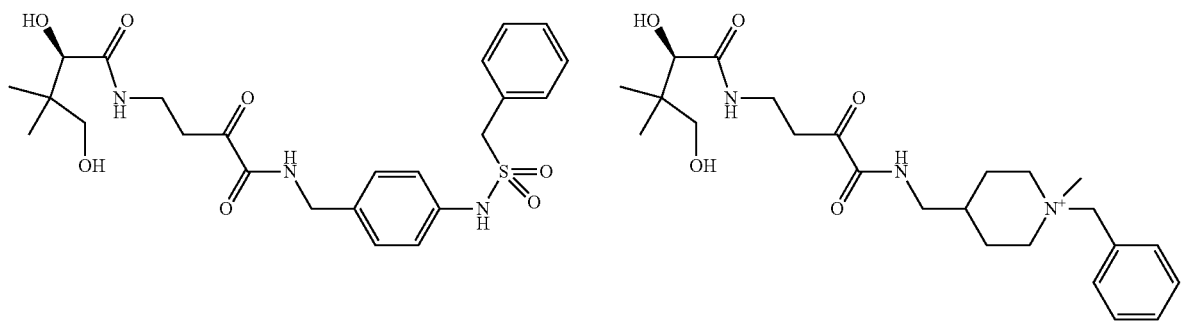
78
79
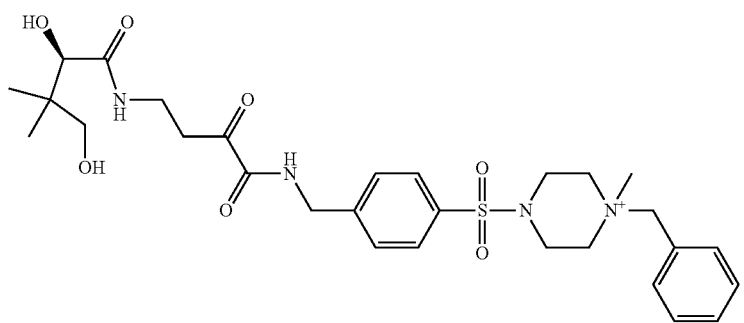
80
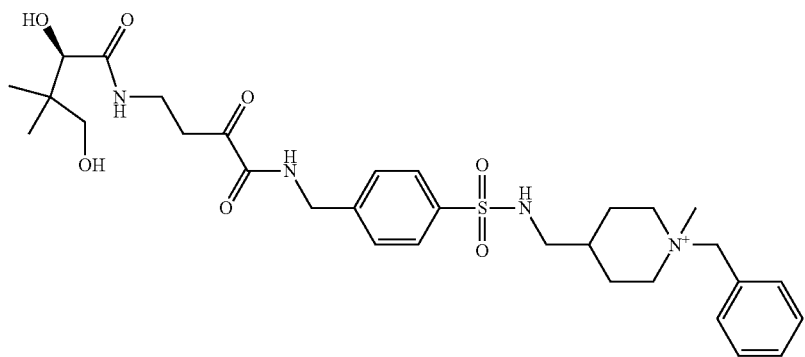
81

-continued

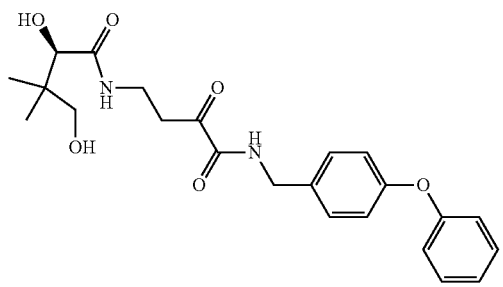
82

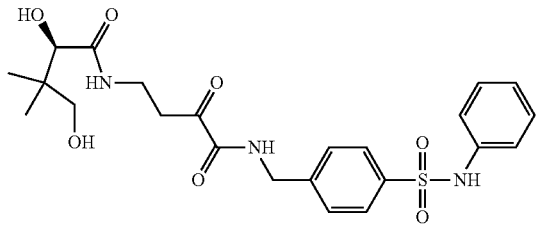
83 and

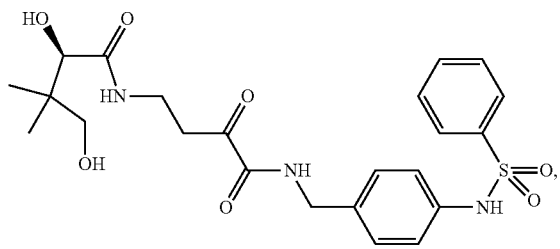
84 and pharmaceutically usable solvates, salts, hydrates and stereoisomers thereof, including mixtures thereof in all ratios.

9. A kit consisting of separate packs of:
(a) an effective amount of a compound according to claim 8 and/or pharmaceutically usable solvates, salts, hydrates and stereoisomers thereof, including mixtures thereof in all ratios, and
(b) an effective amount of a further medicament active ingredient.

10. A pharmaceutical composition comprising a compound according to claim 8.

11. A method of treating an inflammatory disease comprising administering a compound according to claim 8 to an individual having an inflammatory disease.

12. The method according claim 11, wherein the inflammatory disease is inflammatory bowel disease.

13. The method according to claim 11, wherein the inflammatory bowel disease is ulcerative colitis.

\* \* \* \* \*

UNITED STATES PATENT AND TRADEMARK OFFICE
CERTIFICATE OF CORRECTION

PATENT NO.         : 9,585,891 B2                                                                    Page 1 of 3
APPLICATION NO.    : 14/430953
DATED              : March 7, 2017
INVENTOR(S)        : Mathilde Muzerelle, Dominique Swinnen and Jeyaprakashnarayanan Seenisamy It is certified that error appears in the above-identified patent and that said Letters Patent is hereby corrected as shown below:

In the Specification

Column 1,
Line 48, "from $-CHIR^c-$ and" should read --from $-CHR^c-$ and--.

Column 11,
Lines 7-13,

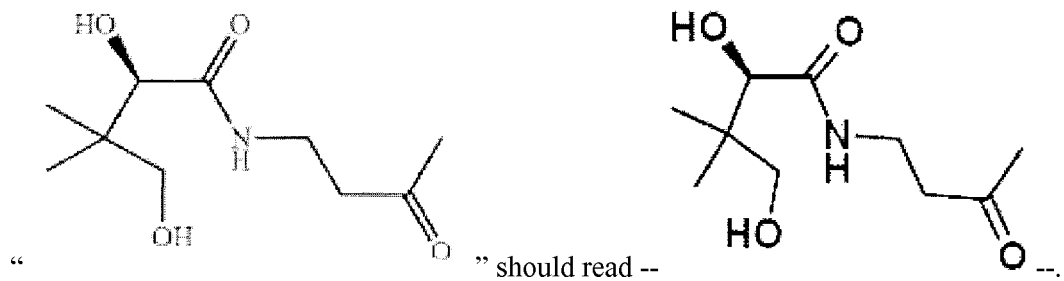

Column 69,
Lines 10-20,

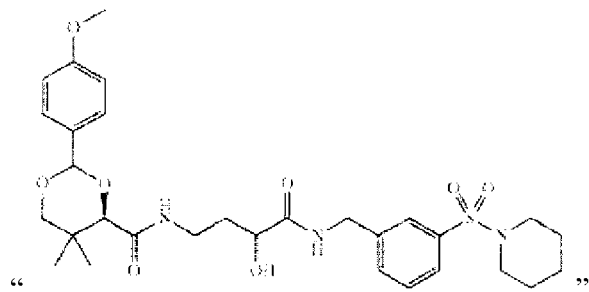

Signed and Sealed this
Seventh Day of November, 2017

Joseph Matal
*Performing the Functions and Duties of the
Under Secretary of Commerce for Intellectual Property and
Director of the United States Patent and Trademark Office* should read -- 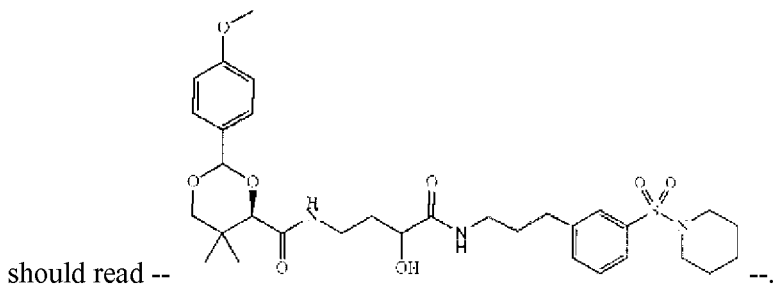 --.

Column 69,
Lines 37-38, "-benzylcarbamoyl}-propyl)-amide" should read -- -benzylcarbamoyl]-propyl}-amide--.

Column 73,
Line 2, "acid }3-" should read --acid {3- --.
Lines 38-39, "-benzylcarbamoyl}-propyl)-amide" should read -- -benzylcarbamoyl]-propyl}-amide--.

Column 84,
Line 27, "dimethyl-butrylamino)-" should read --dimethyl-butyrylamino)- --.
Line 49, "(R)—N-(2-[2-(4-Bromo-" should read --(R)-N-{2-[2-(4-Bromo- --.
Line 50, "ethyl)-2" should read --ethyl}-2--.

Column 97,
Lines 57-58, "{2-hydroxy-4-R(R)" should read --{2-hydroxy-4-[((R)--.

Column 99,
Line 40, "-propyl)-" should read -- -propyl}- --.

Column 102,
Line 20, "(R)—N-(3-" should read --(R)-N-{3- --.
Line 21, "propyl)-" should read --propyl}- --.

Column 103,
Line 18, "benzylcarbamoyl}-propyl)-" should read --benzylcarbamoyl]-propyl}- --.

Column 104,
Line 47, "-N-(3-" should read -- -N-{3- --.
Line 48, "-propyl)-" should read -- -propyl}- --.

Column 105,
Lines 13-14, "propylcarbamoyl}-propyl)butyramide" should read --propylcarbamoyl]-propyl}-butyramide--.

Column 107,
Line 3, "-N-(3-" should read -- -N-{3- --.
Lines 4-5, "-propyl)-" should read -- -propyl}- --.

Column 108,
Lines 38-39, "N-(3-[(1-methanesulfonyl-piperidin-4-ylmethyl)-carbamoyl]-3-oxo-propyl)" should read --N-{3-[(1-methanesulfonyl-piperidin-4-ylmethyl)-carbamoyl]-3-oxo-propyl}--.

Column 109,
Lines 4-5, "N-(3-[(1-Acetyl-piperidin-4-ylmethyl)-carbamoyl]-3-oxo-propyl)" should read --N-{3-[(1-Acetyl-piperidin-4-ylmethyl)-carbamoyl]-3-oxo-propyl}--.

Column 110,
Lines 4-5, "N-(3-[4-(2-methoxy-ethoxy)-benzylcarbamoyl]-3-oxo-propyl)" should read --N-{3-[4-(2-methoxy-ethoxy)-benzylcarbamoyl]-3-oxo-propyl}--.